(12) United States Patent
Tenda et al.

(10) Patent No.: US 11,897,954 B2
(45) Date of Patent: Feb. 13, 2024

(54) ANTI-TSPAN8/ANTI-CD3 BISPECIFIC ANTIBODY AND ANTI-TSPAN8 ANTIBODY

(71) Applicants: Astellas Pharma Inc., Tokyo (JP); National Cancer Center, Tokyo (JP)

(72) Inventors: Yoshiyuki Tenda, Tokyo (JP); Masatoshi Yuri, Tokyo (JP); Daisuke Yamajuku, Tokyo (JP); Takeshi Tsutsumi, Tokyo (JP); Yuko Kusuzaki, Tokyo (JP); Hiroki Sasaki, Chuo-ku (JP); Fumiko Chiwaki, Chuo-ku (JP); Masayuki Komatsu, Chuo-ku (JP)

(73) Assignees: Astellas Pharma Inc., Tokyo (JP); National Cancer Center, Tokyo (JP)

( * ) Notice: Subject to any disclaimer, the term of this patent is extended or adjusted under 35 U.S.C. 154(b) by 148 days.

(21) Appl. No.: 17/639,783

(22) PCT Filed: Nov. 15, 2021

(86) PCT No.: PCT/JP2021/041839
§ 371 (c)(1),
(2) Date: Mar. 2, 2022

(87) PCT Pub. No.: WO2022/102768
PCT Pub. Date: May 19, 2022

(65) Prior Publication Data
US 2023/0348587 A1   Nov. 2, 2023

(30) Foreign Application Priority Data

Nov. 16, 2020  (JP) .............................. 2020-189988

(51) Int. Cl.
*C07K 16/28* (2006.01)
*A61P 35/00* (2006.01)
*A61K 39/00* (2006.01)

(52) U.S. Cl.
CPC .............. *C07K 16/28* (2013.01); *A61P 35/00* (2018.01); *C07K 16/2809* (2013.01); *A61K 2039/505* (2013.01); *C07K 2317/21* (2013.01); *C07K 2317/24* (2013.01); *C07K 2317/31* (2013.01); *C07K 2317/40* (2013.01); *C07K 2317/52* (2013.01); *C07K 2317/55* (2013.01); *C07K 2317/622* (2013.01); *C07K 2317/732* (2013.01); *C07K 2317/76* (2013.01)

(58) Field of Classification Search
CPC ...................................................... C07K 16/28
USPC ...................................................... 424/135.1
See application file for complete search history.

(56) References Cited

U.S. PATENT DOCUMENTS

| 2016/0039931 A1 | 2/2016 | Azorsa |
| 2017/0267783 A1 | 9/2017 | Nezu et al. |

FOREIGN PATENT DOCUMENTS

| JP | 2016-513713 A | 5/2016 |
| JP | 2016-166174 A | 9/2016 |
| JP | 2019-104699 A | 6/2019 |
| WO | WO-2012/010696 A1 | 1/2012 |
| WO | WO-2015/130115 A1 | 9/2015 |

OTHER PUBLICATIONS

Bonnet et al., "Targeting the Tetraspanins with Monoclonal Antibodies in Oncology: Focus on Tspan8/Co-029," Cancers, Feb. 4, 2019, 11(2):179, 1-14.
Brinkmann et al., "The making of bispecific antibodies," MABS, 2017, 9(2):182-212.
Heo et al., "TSPAN8 as a Novel Emerging Therapeutic Target in Cancer for Monoclonal Antibody Therapy," Biomolecules, Mar. 3, 2020, 10(3):388, 1-13.
International Search Report dated Dec. 28, 2021 in PCT/JP2021/041839, with English translation.
Oliveira Rosso et al., "Photobiomodulation Therapy Associated with Heterologous Fibrin Biopolymer and Bovine Bone Matrix Helps to Reconstruct Long Bones," Biomolecules, Mar. 2, 2020, 10(3):383, 1-17.
Wu et al., "T cell engaging bispecific antibody (T-BsAb): from technology to therapeutics," Pharmacol. Ther., Feb. 2018, 182:161-175.

*Primary Examiner* — Sean E Aeder
(74) *Attorney, Agent, or Firm* — Foley & Lardner LLP

(57) ABSTRACT

An objective of the present invention is to provide an anti-TSPAN8/anti-CD3 bispecific antibody and an anti-TSPAN8 antibody usable in treatment or prevention in human. A human monoclonal antibody producing mouse was immunized with a peritoneal disseminated cancer cell isolated from a patient, to obtain an antibody 16B11 and an antibody 16B12 that selectively bind to a peritoneal disseminated cancer cell. These antibodies were anti-TSPAN8 antibodies that bind to the region from amino acid positions 126 to 155 of TSPAN8 and exhibited strong binding activity to TSPAN8 expressed in the peritoneal disseminated cancer cell. Further, an anti-TSPAN8(16B11)-anti-CD3 bispecific antibody produced based on the sequence of 16B11 exhibited a cytotoxic activity against the TSPAN8-expressing cancer cell in vitro, exerted an anti-tumor action on TSPAN8-expressing cancer cell-bearing mice in vivo, and extended the lifetime of peritoneal dissemination model mice.

20 Claims, 21 Drawing Sheets
Specification includes a Sequence Listing.

Fluorescence Intensity

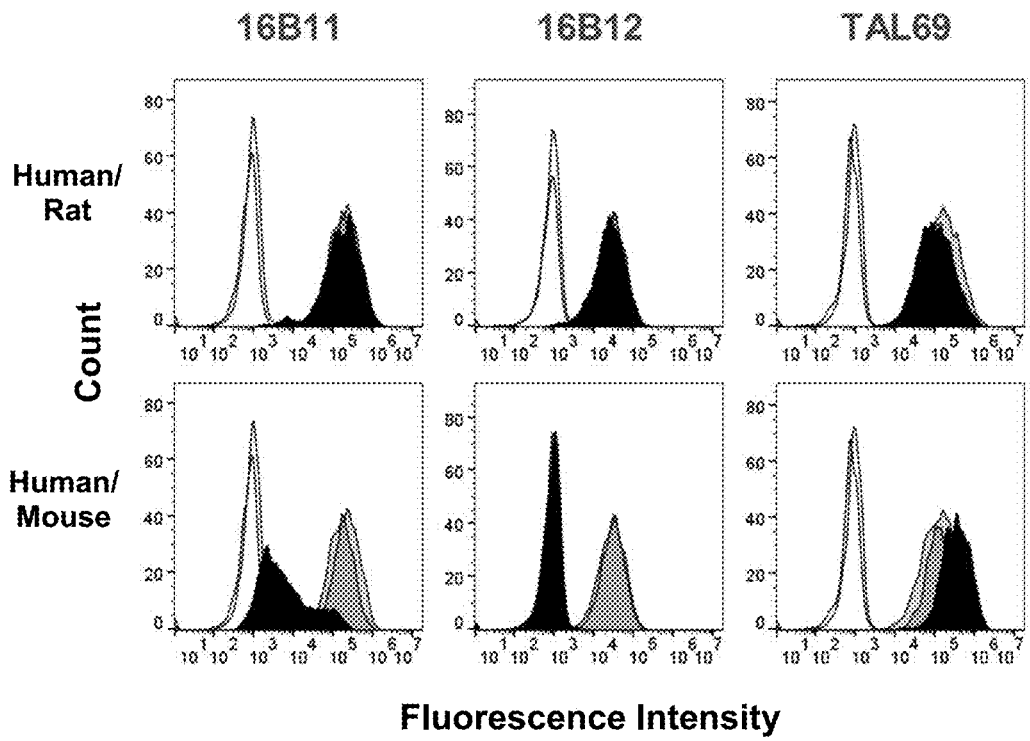

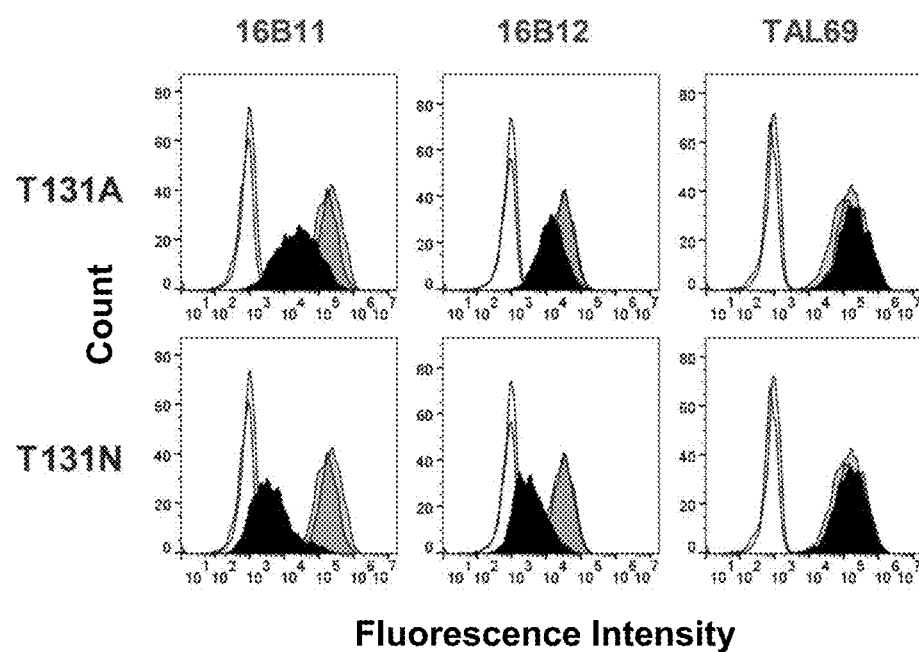

ANTI-TSPAN8/ANTI-CD3 BISPECIFIC ANTIBODY AND ANTI-TSPAN8 ANTIBODY

CROSS-REFERENCE TO RELATED APPLICATIONS

This application is the U.S. National Stage of PCT/JP2021/041839, filed Nov. 15, 2022, which claims priority to JP 2020-189988, filed Nov. 16, 2020.

The instant application contains a Sequence Listing which has been submitted in ASCII format via EFS-WEB and is hereby incorporated by reference in its entirety. Said ASCII copy, created on Feb. 11, 2022, is named sequence.txt and is 72,113 bytes.

TECHNICAL FIELD

The present invention relates to an anti-TSPAN8/anti-CD3 bispecific antibody and an anti-TSPAN8 antibody useful as an active ingredient of a pharmaceutical composition to be used for treatment in a human.

BACKGROUND ART

Metastatic gastric cancer refers to a state where primary gastric cancer has infiltrated deeper beyond a muscular layer, and broken the serosa covering the stomach wall to metastasize to the lymph nodes or the abdominal cavity, and further to various organs via blood or lymph, and more than half of patients suffering from metastatic gastric cancer have dissemination to the abdominal cavity. It is known that terminal patients have symptoms of swelling of the abdomen due to accumulation of ascites fluid caused by the peritoneal dissemination, continuous distension, pain, nausea, dyspnea, insomnia and fatigue (World J. Gastroenterol., 2016, Vol.22, p. 6829-6840, and Int. J. Cancer, 2010, Vol.127, p.2209-2221). It is, however, difficult to completely cure a patient suffering from gastric cancer peritoneal dissemination by surgery, and chemotherapy, that is, standard therapy for gastric cancer peritoneal dissemination, does not have sufficient effectiveness. Therefore, the prognosis is so poor that the five-year survival rate of such a patient is as low as about 2%, and effective therapy for gastric cancer peritoneal dissemination is desired. Besides, peritoneal dissemination is found to occur in many cancer patients with primary cancer of ovarian cancer, colorectal cancer, pancreatic cancer and the like (Int. J. Adv. Res., 2016, Vol. 4, p. 735-748), and a therapeutic method for these patients has not been established yet.

In development of antibodies for treating cancer, attempts have been made for identifying a tumor associated antigen (TAA) selectively expressed in a cancer cell by various methods. As one of these methods, a method in which an antibody is produced by immunizing an animal with a cancer cell to obtain an antibody that binds to a TAA expressed in the cancer cell has been reported (Biochem. Biophys. Res. Commun., 2018, Vol. 505, p. 181e-186, and FEBS Open Bio, 2017, Vol. 7, p. 627-635).

Tetraspanin-8 (TSPAN8) is a four pass transmembrane protein belonging to the tetraspanin family, has two extracellular loop regions of a small extracellular loop (SEL) and a large extracellular loop (LEL) and three cytoplasmic domains, and forms a molecular cluster having, as scaffold proteins, a variety of transmembrane proteins and cytoplasmic proteins. TSPAN8 is known to be involved in cell adhesion, cell motility, and cell activation and growth and the like, and is expressed at a high level in gastric cancer, pancreatic cancer, colorectal cancer, liver cancer and the like. It has been reported that there is a relationship or the like between increased expression of TSPAN8 and progression or metastasis of cancer (NON PATENT LITERATURE 1). Studies are being made to aim at diagnosis or treatment of cancer using an anti-TSPAN8 antibody (PATENT LITERATUREs 1-2 and NON PATENT LITERATUREs 1-2).

Cluster of differentiation 3 (CD3) is a protein that transmits an activation signal to a T cell by forming, on the surface of the T cell, a complex together with a T cell receptor (TCR). CD3 is a complex consisting of five subunits of gamma (γ), delta (δ), epsilon (ε), zeta (ζ) and eta (η) chains, and the subunits form three dimers, εγ, εδ and ζζ. CD3 is expressed in both a normal T cell and a tumor T cell, and hence is used as a T cell marker. Besides, various reports have been made on application, as a pharmaceutical, of bispecific antibodies including various anti-TAA antibodies and anti-CD3 antibodies for cancer treatment (NON PATENT LITERATURE 3).

As an innovative method by which cancer cell-selective cytotoxic activity can be obtained at a low antibody concentration, bispecific T cell recruiting antibodies having various antibody formats have been reported, and the effects of these antibodies on T cell mediated immunotherapy are under examination (NON PATENT LITERATURE 4). A bispecific T cell recruiting antibody is a bispecific antibody including an antibody to a TAA expressed on a cancer cell surface, and an antibody that binds to a T cell. As the antibody that binds to a T cell, anti-CD3 antibodies are used in many cases. A bispecific T cell recruiting antibody including anti-TAA and anti-CD3 antibodies makes small a physical distance between a target cancer cell and a cytotoxic T lymphocyte (CTL) to activate the CTL by the anti-CD3 antibody for killing the cancer cell with cytotoxic activity of the CTL (redirected T cell cytotoxicity; RTCC). Catumaxomab, that is, an anti-CD3/anti-epithelial cell adhesion molecule (EpCAM) bispecific antibody, and blinatumomab, that is, an anti-CD3/anti-CD19 (Cluster of Differentiation 19) bispecific antibody, have already been confirmed to have clinical effects (Int. J. Cancer, 2010, Vol. 127, p.2209-2221, and N. Engl. J. Med., 2017, Vol. 376, p. 836-847). Also at present, various bispecific T cell recruiting antibodies to TAA are being studied and developed. Up to the present, however, no anti-TSPAN8/anti-CD3 bispecific antibody has been known.

CITATION LIST

Patent Literature

PATENT LITERATURE 1: International Publication No. 2012/010696
PATENT LITERATURE 2: International Publication No. 2015/130115

Non Patent Literature

NON PATENT LITERATURE 1: Biomolecules (Switzerland), 2020; 10 (3) p.383
NON PATENT LITERATURE 2: Cancers (Switzerland), 2019; 11 (2) p.179
NON PATENT LITERATURE 3: Pharmacology and Therapeutics (Great Britain), 2018; 182: p. 161-175
NON PATENT LITERATURE 4: mAbs, 2017: 9(2): p. 182-212

SUMMARY OF INVENTION

Technical Problem

An objective of the present invention is to provide an anti-TSPAN8/anti-CD3 bispecific antibody and an anti-TSPAN8 antibody usable in treatment in human.

Means to Solve the Problem

For the purposes of creating a therapeutic agent selectively acting on a cancer cell, the present inventors obtained 16B11 and 16B12 which are anti-TSPAN8 antibodies by employing a method for obtaining an antibody by immunizing a human monoclonal antibody producing mouse with a peritoneal disseminated cancer cell isolated from a patient (Example 1). The antibodies bound to TSPAN8 expressed on a peritoneal disseminated cancer cell more strongly than to TSPAN8 expressed on a normal cell (Examples 1 to 5). It was found from the epitope analysis of 16B11 and 16B12 that the antibodies recognize a region consisting of an amino acid sequence of amino acid positions 126 to 155 of human TSPAN8 as an epitope, and the threonine at position 131 of human TSPAN8 is essential for binding of the antibodies (Example 4). Further, a fully human antibody, 16B11.1, formed by converting the Fc region of 16B11 into a human sequence was produced (Example 3), and it was found that the fully human antibody exhibited cytotoxic activity against a 60As6-Luc/GFP cell (Example 6).

Besides, in order to increase antigen-selective anti-tumor activity of a T cell, an anti-TSPAN8/anti-CD3 bispecific antibody comprising: a heavy chain variable region of an anti-TSPAN8 antibody consisting of an amino acid sequence from amino acid positions 1 to 121 of SEQ ID NO: 6, and a light chain variable region of an anti-TSPAN8 antibody consisting of an amino acid sequence from amino acid positions 1 to 107 of SEQ ID NO: 8; and an anti-CD3-scFv region comprising a heavy chain variable region of an anti-CD3 antibody consisting of an amino acid sequence from amino acid positions 1 to 125 of SEQ ID NO: 14 and a light chain variable region of an anti-CD3 antibody consisting of an amino acid sequence from amino acid positions 146 to 254 of SEQ ID NO: 14 was produced (Example 7). It was confirmed that this bispecific antibody bound to TSPAN8 and CD3 (Example 8), exhibited cytotoxic activity against a cancer cell expressing TSPAN8 on the cell surface (Examples 9, 10, 12-1, and 12-2), and elongated the lifetime of mice in vivo to exert anti-tumor effects (Examples 11 and 12-3).

Specifically, the present invention relates to the following [1] to [55]:

[1] A bispecific antibody that binds to TSPAN8 and CD3, comprising:
 (a) a Fab region of an anti-TSPAN8 antibody consisting of: a heavy chain fragment comprising a heavy chain variable region of the anti-TSPAN8 antibody; and a light chain comprising a light chain variable region of the anti-TSPAN8 antibody;
 (b) an anti-CD3-scFv region comprising a heavy chain variable region and a light chain variable region of an anti-CD3 antibody; and
 (c) a Fc region consisting of a first Fc polypeptide linked to the heavy chain fragment of the Fab region (a) and a second Fc polypeptide linked to the anti-CD3-scFv region (b).

[2] The bispecific antibody according to [1], wherein
 the heavy chain variable region of the anti-TSPAN8 antibody comprises a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6, and the light chain variable region of the anti-TSPAN8 antibody comprises a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; or
 the heavy chain variable region of the anti-TSPAN8 antibody comprises a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10, and the light chain variable region of the anti-TSPAN8 antibody comprises a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12.

[3] The bispecific antibody according to [1], wherein
 the heavy chain variable region of the anti-TSPAN8 antibody consists of an amino acid sequence from amino acid positions 1 to 121 of SEQ ID NO: 6, and the light chain variable region of the anti-TSPAN8 antibody consists of an amino acid sequence from amino acid positions 1 to 107 of SEQ ID NO: 8; or
 the heavy chain variable region of the anti-TSPAN8 antibody consists of an amino acid sequence from amino acid positions 1 to 121 of SEQ ID NO: 10, and the light chain variable region of the anti-TSPAN8 antibody consists of an amino acid sequence from amino acid positions 1 to 107 of SEQ ID NO: 12.

[4] The bispecific antibody according to [1], wherein
 the Fab region of the anti-TSPAN8 antibody consists of a heavy chain fragment consisting of an amino acid sequence from amino acid positions 1 to 219 of SEQ ID NO: 6 and a light chain consisting of an amino acid sequence of SEQ ID NO: 8, or
 the Fab region of the anti-TSPAN8 antibody consists of a heavy chain fragment consisting of an amino acid sequence from amino acid positions 1 to 219 of SEQ ID NO: 10 and a light chain consisting of an amino acid sequence of SEQ ID NO: 12.

[5] The bispecific antibody according to any one of [1] to [4],
 wherein the heavy chain variable region of the anti-CD3 antibody comprises a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and the light chain variable region of the anti-CD3 antibody comprises a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14.

[6] The bispecific antibody according to any one of [1] to [4],
wherein the heavy chain variable region of the anti-CD3 antibody consists of an amino acid sequence from amino acid positions 1 to 125 of SEQ ID NO: 14, and the light chain variable region of the anti-CD3 antibody consists of an amino acid sequence from amino acid positions 146 to 254 of SEQ ID NO: 14.

[7] The bispecific antibody according to any one of [1] to [4], wherein the anti-CD3-scFv region consists of an amino acid sequence from amino acid positions 1 to 254 of SEQ ID NO: 14.

[8] The bispecific antibody according to [1], wherein
the bispecific antibody comprises: a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; and a polypeptide in which an anti-CD3-scFv region comprising a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide, or
the bispecific antibody comprises: a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12; and a polypeptide in which an anti-CD3-scFv region comprising a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide.

[9] The bispecific antibody according to [1], wherein
the bispecific antibody comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide, a light chain of an anti-TSPAN8 antibody comprising a light chain variable region consisting of an amino acid sequence from amino acid positions 1 to 107 of SEQ ID NO: 8, and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of an anti-CD3 antibody consisting of an amino acid sequence from amino acid positions 146 to 254 of SEQ ID NO: 14 is linked to a second Fc polypeptide, or
the bispecific antibody comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide, a light chain of the anti-TSPAN8 antibody comprising a light chain variable region consisting of an amino acid sequence from amino acid positions 1 to 107 of SEQ ID NO: 12, and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of an anti-CD3 antibody consisting of an amino acid sequence from amino acid positions 146 to 254 of SEQ ID NO: 14 is linked to a second Fc polypeptide.

[10] The bispecific antibody according to any one of [1] to [9], comprising a Fc region containing LALA mutation (L234A and L235A (wherein positions of mutation are amino acid positions in human Igγ1 constant region according to EU index)).

[11] The bispecific antibody according to any one of [1] to [10], comprising a Fc region containing N297G mutation (wherein a position of mutation is an amino acid position in human Igγ1 constant region according to EU index).

[12] The bispecific antibody according to any one of [1] to [11], comprising a Fc region containing knobs-into-holes mutation.

[13] The bispecific antibody according to any one of [1] to [12], comprising a Fc region containing LALA mutation, N297G mutation and knobs-into-holes mutation.
[14] The bispecific antibody according to [12] or [13], wherein the knobs-into-holes mutation is T366W mutation in one Fc polypeptide included in the Fc region, and T366S, L368A and Y407V mutation in another Fc polypeptide included in the Fc region (wherein positions of mutation are amino acid positions in human Igyl constant region according to EU index).
[15] The bispecific antibody according to any one of [1] to [14], comprising a Fc region in which the first Fc polypeptide consists of an amino acid sequence from amino acids 235 to 451 of SEQ ID NO: 6 and the second Fc polypeptide consists of an amino acid sequence from amino acids 270 to 486 of SEQ ID NO: 14.
[16] The bispecific antibody according to any one of [1] to [15],
wherein the heavy chain fragment of the anti-TSPAN8 antibody and the first Fc polypeptide are linked through a hinge region, and the anti-CD3-scFv region and the second Fc polypeptide are linked through a hinge region.
[17] The bispecific antibody according to [1], comprising: a heavy chain of the anti-TSPAN8 antibody consisting of an amino acid sequence of SEQ ID NO: 6 in which the heavy chain fragment of the anti-TSPAN8 antibody is linked to the first Fc polypeptide; a light chain of the anti-TSPAN8 antibody consisting of an amino acid sequence of SEQ ID NO: 8; and a polypeptide consisting of an amino acid sequence of SEQ ID NO: 14 in which the anti-CD3-scFv region is linked to the second Fc polypeptide.
[18] The bispecific antibody according to any one of [2] to [17], post-translationally modified.
[19] The bispecific antibody according to [18], wherein the post-translational modification is pyroglutamylation at a N-terminal of the heavy chain variable region and/or lysine deletion at a heavy chain C-terminal.
[20] A polynucleotide selected from the group consisting of the following (a) to (e):
  (a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide;
  (b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8;
  (c) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide;
  (d) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12;
  (e) a polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.
[21] A polynucleotide selected from the group consisting of the following (a) to (c):
  (a) a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide;
  (b) a polynucleotide comprising a nucleotide sequence encoding a light chain of an anti-TSPAN8 antibody consisting of an amino acid sequence of SEQ ID NO: 8; and
  (c) a polynucleotide comprising a nucleotide sequence encoding a polypeptide consisting of an amino acid sequence of SEQ ID NO: 14 in which the anti-CD3-scFv region is linked to a second Fc polypeptide.
[22] An expression vector comprising the polynucleotide according to [20] or [21].
[23] A host cell transformed with the expression vector according to [22].
[24] A host cell comprising: a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; a polynucleotide comprising a nucleotide sequence encoding a light chain of an anti-TSPAN8 antibody comprising a light chain variable region consisting of an amino acid sequence from amino acid positions 1 to 107 of SEQ ID NO: 8; and a polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.
[25] A host cell comprising: a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide; a polynucleotide comprising a nucleotide sequence encoding a light chain of an anti-TSPAN8 antibody consisting of an amino acid sequence of SEQ ID NO: 8; and a polynucleotide comprising a nucleotide sequence encoding a polypeptide consisting of an amino acid sequence of SEQ ID NO: 14 in which an anti-CD3-scFv region is linked to a second Fc polypeptide.
[26] A method for producing a bispecific antibody that binds to TSPAN8 and CD3, comprising a step of culturing the host cell according to any one of [23] to [25].
[27] A pharmaceutical composition comprising the bispecific antibody according to any one of [1] to [19], and a pharmaceutically acceptable excipient.
[28] The bispecific antibody according to any one of [1] to [19], for use in treating cancer.
[29] The pharmaceutical composition according to [27], for treating cancer.

[30] A method for treating cancer, comprising a step of administering, to a subject, a therapeutically effective amount of the bispecific antibody according to any one of [1] to [19].

[31] Use of the bispecific antibody according to any one of [1] to [19], in production of a pharmaceutical composition for treating cancer.

[32] An anti-TSPAN8 antibody or an antigen-binding fragment thereof that selectively binds to a human TSPAN8 expressing cancer cell.

[33] An anti-TSPAN8 antibody or an antigen-binding fragment thereof that binds to at least one amino acid present in the human TSPAN8 region from amino acid positions 126 to 155 of SEQ ID NO: 2.

[34] The anti-TSPAN8 antibody or the antigen-binding fragment thereof according to [33], which binds to at least the amino acid at amino acid position 131 of SEQ ID NO: 2 present in the human TSPAN8 region.

[35] An anti-TSPAN8 antibody or an antigen-binding fragment thereof selected from the following (a) and (b):
(a) an anti-TSPAN8 antibody or an antigen-binding fragment thereof, comprising a heavy chain variable region comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4, and a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
(b) an anti-TSPAN8 antibody or an antigen-binding fragment thereof, comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10, and a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO. 12.

[36] The anti-TSPAN8 antibody or the antigen-binding fragment thereof according to [35], selected from the following (a) and (b):
(a) an anti-TSPAN8 antibody or an antigen-binding fragment thereof comprising a heavy chain variable region consisting of an amino acid sequence from amino acid positions 1 to 121 of SEQ ID NO: 4, and a light chain variable region consisting of an amino acid sequence from amino acid positions 1 to 107 of SEQ ID NO: 8; and
(b) an anti-TSPAN8 antibody or an antigen-binding fragment thereof comprising a heavy chain variable region consisting of an amino acid sequence from amino acid positions 1 to 121 of SEQ ID NO: 10, and a light chain variable region consisting of an amino acid sequence from amino acid positions 1 to 107 of SEQ ID NO: 12.

[37] The anti-TSPAN8 antibody according to [35], selected from the following (a) and (b):
(a) an anti-TSPAN8 antibody comprising a heavy chain consisting of an amino acid sequence of SEQ ID NO: 4 and a light chain consisting of an amino acid sequence of SEQ ID NO: 8; and
(b) an anti-TSPAN8 antibody comprising a heavy chain consisting of an amino acid sequence of SEQ ID NO: 10 and a light chain consisting of an amino acid sequence of SEQ ID NO: 12.

[38] An anti-TSPAN8 antibody or an antigen-binding fragment thereof that competes with the anti-TSPAN8 antibody or the antigen-binding fragment thereof according to any one of [33] to [37] in binding to the human TSPAN8 expressing cancer cell.

[39] The anti-TSPAN8 antibody or the antigen-binding fragment thereof according to any one of [32] to [38], linked to an antibody to a surface antigen of T cell or NK cell, or an antigen-binding fragment thereof

[40] The anti-TSPAN8 antibody or the antigen-binding fragment thereof according to [39], wherein the surface antigen of T cell is CD3.

[41] The anti-TSPAN8 antibody or the antigen-binding fragment thereof according to [40], wherein the antigen-binding fragment to the surface antigen of T cell is scFv of an anti-CD3 antibody.

[42] The anti-TSPAN8 antibody or the antigen-binding fragment thereof according to any one of [32] to [41], post-translationally modified.

[43] The anti-TSPAN8 antibody or the antigen-binding fragment thereof according to [42], wherein the post-translational modification is pyroglutamylation at a N-terminal of a heavy chain variable region and/or lysine deletion at a heavy chain C-terminal.

[44] A fusion or complex of the anti-TSPAN8 antibody or the antigen-binding fragment thereof according to any one of [32] to [43], or a cell on a surface of which the anti-TSPAN8 or the antigen-binding fragment thereof according to any one of [32] to [43] is expressed.

[45] A polynucleotide selected from the group consisting of the following (a) to (d):
(a) a polynucleotide comprising a nucleotide sequence encoding a heavy chain variable region of an anti-TSPAN8 antibody consisting of an amino acid sequence from amino acid positions 1 to 121 of SEQ ID NO: 4;
(b) a polynucleotide comprising a nucleotide sequence encoding a light chain variable region of an anti-TSPAN8 antibody consisting of an amino acid sequence from amino acid positions 1 to 107 of SEQ ID NO: 8;
(c) a polynucleotide comprising a nucleotide sequence encoding a heavy chain variable region of an anti-TSPAN8 antibody consisting of an amino acid sequence from amino acid positions 1 to 121 of SEQ ID NO: 10; and
(d) a polynucleotide comprising a nucleotide sequence encoding a light chain variable region of an anti-TSPAN8 antibody consisting of an amino acid sequence from amino acid positions 1 to 107 of SEQ ID NO: 12.

[46] A polynucleotide selected from the group consisting of the following (a) to (d):
(a) a polynucleotide comprising a nucleotide sequence encoding a heavy chain of an anti-TSPAN8 antibody consisting of an amino acid sequence of SEQ ID NO: 4;

(b) a polynucleotide comprising a nucleotide sequence encoding a light chain of an anti-TSPAN8 antibody consisting of an amino acid sequence of SEQ ID NO: 8;

(c) a polynucleotide comprising a nucleotide sequence encoding a heavy chain of an anti-TSPAN8 antibody consisting of an amino acid sequence of SEQ ID NO: 10; and (d) a polynucleotide comprising a nucleotide sequence encoding a light chain of an anti-TSPAN8 antibody consisting of an amino acid sequence of SEQ ID NO: 12.

[47] An expression vector, comprising the polynucleotide according to [45] or [46].

[48] A host cell transformed with the expression vector according to [47].

[49] A host cell selected from the following (a) and (b):
(a) a host cell comprising the polynucleotide comprising a nucleotide sequence encoding a heavy chain variable region of an anti-TSPAN8 antibody according to [45], and the polynucleotide comprising a nucleotide sequence encoding a light chain variable region of an anti-TSPAN8 antibody according to [45]; and
(b) a host cell comprising the polynucleotide comprising a nucleotide sequence encoding a heavy chain of an anti-TSPAN8 antibody according to [46], and the polynucleotide comprising a nucleotide sequence encoding a light chain of an anti-TSPAN8 antibody according to [46].

[50] A method for producing an anti-TSPAN8 antibody or an antigen-binding fragment thereof, comprising a step of culturing the host cell according to [48] or [49].

[51] The anti-TSPAN8 antibody or the antigen-binding fragment thereof according to any one of [32] to [43], or the fusion, the complex, or the cell according to [44], for use in treating cancer.

[52] A pharmaceutical composition comprising the anti-TSPAN8 antibody or the antigen-binding fragment thereof according to any one of [32] to [43], or the fusion, the complex, or the cell according to [44], and a pharmaceutically acceptable excipient.

[53] The pharmaceutical composition according to [52], for treating cancer.

[54] A method for treating cancer, comprising a step of administering, to a subject, a therapeutically effective amount of the anti-TSPAN8 antibody or the antigen-binding fragment thereof according to any one of [32] to [43], or a step of administering, to a subject, a therapeutically effective amount of the fusion, the complex, or the cell according to [44].

[55] Use of the anti-TSPAN8 antibody or the antigen-binding fragment thereof according to any one of [32] to [43], or use of the fusion, the complex, or the cell according to [44], in production of a pharmaceutical composition for treating cancer.

Advantageous Effects of Invention

An anti-TSPAN8/anti-CD3 bispecific antibody of the present invention binds to both TSPAN8, a cancer antigen, and CD3, a T cell surface molecule, and enhances cancer cell killing action of a T cell by making small a physical distance between a cancer cell and the T cell. Besides, an anti-TSPAN8 antibody of the present invention exhibits cancer cell killing effect by binding to TSPAN8. The anti-TSPAN8/anti-CD3 bispecific antibody and the anti-TSPAN8 antibody of the present invention or a pharmaceutical composition containing the antibody can be used for treating cancer.

BRIEF DESCRIPTION OF DRAWINGS

FIG. 1-2 illustrates results of measurement with flow cytometry of a binding of anti-TSPAN8 antibodies (16B11, 9F6 and 18C10) to KM-555-As. In the drawing, 16B11, 9F6 and 18C10 indicate the names of the antibodies. The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 1-3 illustrates results of measurement with flow cytometry of a binding of anti-TSPAN8 antibodies (16B11, 9F6 and 18C10) to KM-556-As. In the drawing, 16B11, 9F6 and 18C10 indicate the names of the antibodies. The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 2-1 illustrates results of measurement with flow cytometry of a binding, to a cultured human peritoneal mesothelial cell, of anti-TSPAN8 antibodies (16B11, 16B12 9F6, 5B7, 12C12, 13A9, 15D1 and TAL69). The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 2-2 illustrates results of measurement with flow cytometry of a binding, to a cultured human peritoneal mesothelial cell, of anti-TSPAN8 antibodies (18C10, 19E4, 21F7 and TAL69). The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 3-1 illustrates results of measurement with flow cytometry of a binding, to KM-501-As, of anti-TSPAN8 antibodies (16B11, 16B12, 9F6, 18C10 and TAL69). The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 3-2 illustrates results of measurement with flow cytometry of a binding, to KM-503-As, of anti-TSPAN8 antibodies (16B11, 16B12, 9F6, 18C10 and TAL69). The abscissa of the drawing indicates fluorescence intensity, and the ordinate indicates the cell count. In the drawing, a white area indicates the binding of a negative control antibody, and a dark gray area indicates the binding of the anti-TSPAN 8 antibody.

FIG. 5-1 illustrates results of measurement with flow cytometry of a binding of anti-TSPAN8 antibodies (16B11, 16B12, and TAL69) to a CHO-K1 cell (chimeric protein expressing CHO-K1 cell) expressing human mouse TSPAN8-GFP chimeric protein or human rat TSPAN8-GFP chimeric protein. The abscissa of the drawing indicates fluorescence intensity, and the ordinate indicates the cell count. In the drawing, a gray area indicates a wild-type human TSPAN8 expressing CHO-K1 cell, a black area indicates a chimeric protein expressing CHO-K1 cell, and a white area indicates the binding of the anti-TSPAN8 antibody to a mock cell. The experiment was carried out in duplicate.

FIG. 5-2 illustrates the homology of sequences consisting of amino acid positions 126 to 155 of four TSPAN8 proteins of human, mouse, rat, and cynomolgus monkey. An asterisk indicates that their amino acids perfectly match, and a dot indicates that three of the four proteins have the same amino acids. Space indicates that two or more of them have different amino acids.

FIG. 5-3 illustrates results of measurement with flow cytometry of a binding of anti-TSPAN8 antibodies (16B11, 16B12, and TAL69) to T131A mutant or T131N mutant of the human TSPAN8 proteins. The abscissa of the drawing indicates fluorescence intensity, and the ordinate indicates the cell count. In the drawing, a gray area indicates a wild-type human TSPAN8 expressing CHO-K1 cell, a black area indicates a mutant expressing CHO-K1 cell, a white area indicates the binding of the anti-TSPAN8 antibody to a mock cell. The experiment was carried out in duplicate.

FIG. 6-1 illustrates results of measurement with flow cytometry of a competitive action of other anti-TSPAN8 antibodies (Competitors (CPTR): 16B11, 9F6, 18C10, and TAL69) on the binding of 16B11 to NSC-15CF. The abscissa of the drawing indicates fluorescence intensity, and the ordinate indicates the cell count. In the drawing, a gray area indicates the binding of the fluorescently labeled 16B11 in the presence of a negative control antibody, a black area indicates the binding of the fluorescently labeled 16B11 in the presence of each CPTR, and a white area indicates the histogram of the fluorescently labeled 16B11 unstained.

FIG. 6-2 illustrates results of measurement with flow cytometry of a competitive action of 16B12 on the binding of fluorescently labeled anti-TSPAN8 antibodies (16B11, 9F6, and 18C10) to NSC-15CF. The abscissa of the drawing indicates fluorescence intensity, and the ordinate indicates the cell count. In the drawing, a gray area indicates the binding of the fluorescently labeled anti-TSPAN8 antibody in the presence of a negative control antibody, a black area indicates the binding of the fluorescently labeled anti-TSPAN8 antibody in the presence of 16B12, and a white area indicates the histogram of the fluorescently labeled antibody unstained.

FIG. 6-3 illustrates results of measurement with flow cytometry of a competitive action of other anti-TSPAN8 antibodies (CPTRs: 16B12, 16B11, 9F6, 18C10, and TAL69) on the binding of 16B12 to NSC-15CF. The abscissa of the drawing indicates fluorescence intensity, and the ordinate indicates the cell count. In the drawing, a gray area indicates the binding of the fluorescently labeled 16B12 in the presence of a negative control antibody, a black area indicates the binding of the fluorescently labeled 16B12 in the presence of another anti-TSPAN8 antibody (CPTR), and a white area indicates the histogram of the fluorescently labeled antibody unstained.

FIG. 8-1 and FIG. 8-2 respectively illustrate average values of amounts of the anti-TSPAN8(16B11)-anti-CD3 bispecific antibody bound to the LEL region peptide of TSPAN8 and the CD3εδ complex protein. An error bar indicates a standard deviation.

FIG. 10-1 illustrates cytotoxic activity of the anti-TSPAN8(16B11)-anti-CD3 bispecific antibody against a gastric cancer cell in an ascites cell of a human gastric cancer patient. The abscissa indicates an antibody concentration, and the ordinate indicates a viable cell count (%) obtained 3 days after adding the antibody when the viable cell count with no antibody added is 100%. ● and ■ respectively indicate average values of the viable cell count (%) at each concentration of a control antibody and the anti-TSPAN8 (16B11)-anti-CD3 bispecific antibody. An error bar indicates a standard deviation.

FIG. 10-2 is a diagram illustrating, with induced expression of CD25, activation of CD4-positive T cell caused with the anti-TSPAN8(16B11)-anti-CD3 bispecific antibody in an ascites cell of a human gastric cancer patient. The abscissa indicates an antibody concentration. The ordinate indicates fold changes in expression level of CD25 3 days after adding the antibody to the CD4-positive T cells in ascites. ● and ■ respectively indicate average values of fold changes in expression level of CD25 at each concentration of a control antibody and the anti-TSPAN8(16B11)-anti-CD3 bispecific antibody. An error bar indicates a standard deviation.

FIG. 10-3 is a diagram illustrating, with induced expression of CD25, activation of CD8-positive T cell caused with the anti-TSPAN8(16B11)-anti-CD3 bispecific antibody in an ascites cell of a human gastric cancer patient. The abscissa indicates an antibody concentration. The ordinate indicates fold changes in expression level of CD25 obtained 3 days after adding the antibody to the CD8-positive T cell in ascites. ● and ■ respectively indicate average values of fold changes in expression level of CD25 at each concentration of a control antibody and the anti-TSPAN8(16B11)-anti-CD3 bispecific antibody. An error bar indicates a standard deviation.

FIG. 11-1 illustrates an anti-tumor effect of the anti-TSPAN8(16B11)-anti-CD3 bispecific antibody in a gastric cancer peritoneal dissemination model. The ordinate indicates an average value of amounts of light emission from luciferin caused by luciferase expressed in 60As6-Luc/GFP cell in the abdominal cavity. An error bar indicates a standard error. The abscissa indicates an antibody dose. A significance probability, p-value, was obtained by comparing an amount of light emission in a control group with an amount of light emission in an anti-TSPAN8(16B11)-anti-CD3 bispecific antibody administration group by Dunnett's multiple comparison test. In the drawing, ** indicates a group having a p-value smaller than a significance level of 0.01.

FIG. 11-2 illustrates an effect of the anti-TSPAN8 (16B11)-anti-CD3 bispecific antibody on the number of survival days in a gastric cancer peritoneal dissemination model. The ordinate indicates a survival rate. The abscissa indicates the number of days elapsed after cancer cell transplantation. The anti-TSPAN8(16B11)-anti-CD3 bispecific antibody and expanded pan T cell were administered on day 7 and 10 after 60As6-Luc/GFP transplantation indicated with ▲.

FIG. 13-1 illustrates cytotoxic activity against various cancer cell lines in a co-culture of human peripheral blood mononuclear cell with the anti-TSPAN8(16B11)-anti-CD3 bispecific antibody. The abscissa indicates an antibody concentration, and the ordinate indicates a viable cell count (%) obtained 3 days after adding the antibody of each cancer cell line when the viable cell count with no antibody added is 100% number. Each symbol indicates an average value (quadruplicate) of the viable cell count (%) of each cancer cell line at each concentration of the anti-TSPAN8(16B11)-anti-CD3 bispecific antibody.

FIG. 13-2 is a figure illustrating the induced expression of CD25, which reflects the activation of CD4-positive T cell caused with the anti-TSPAN8(16B11)-anti-CD3 bispecific antibody in a co-culture of human peripheral blood mononuclear cell and various cancer cell lines. The abscissa indicates an antibody concentration. The ordinate indicates fold changes in expression level of CD25 in the CD4-positive T cell obtained 3 days after adding the antibody. Each symbol indicates an average value (quadruplicate) of fold changes in expression level of CD25 at each concentration of the anti-TSPAN8(16B11)-anti-CD3 bispecific antibody.

FIG. 13-3 is a figure illustrating the induced expression of CD25, which reflects the activation of CD8-positive T cell caused with the anti-TSPAN8(16B11)-anti-CD3 bispecific antibody in a co-culture of human peripheral blood mononuclear cell and various cancer cell lines. The abscissa indicates an antibody concentration. The ordinate indicates fold changes in expression level of CD25 in the CD8-positive T cell obtained 3 days after adding the antibody. Each symbol indicates an average value (quadruplicate) of fold changes in expression level of CD25 at each concentration of the anti-TSPAN8(16B11)-anti-CD3 bispecific antibody.

FIG. 14-1 indicates an average value of tumor volume at each number of days after the start of administration of the antibody, and an error bar indicates a standard error. FIG. 14-2 indicates the value of tumor volume of each individual 11 days after the start of administration, the horizontal line indicates an average value and a standard error, and the abscissa indicates an antibody dose. A significant probability, p-value, was obtained by comparing a tumor volume in a PBS administration group with a tumor volume in an anti-TSPAN8(16B11)-anti-CD3 bispecific antibody administration group by Dunnett's multiple comparison test. In the drawing, ** indicates a group having a p-value smaller than a significance level of 0.01.

DESCRIPTION OF EMBODIMENTS

Figure 1:
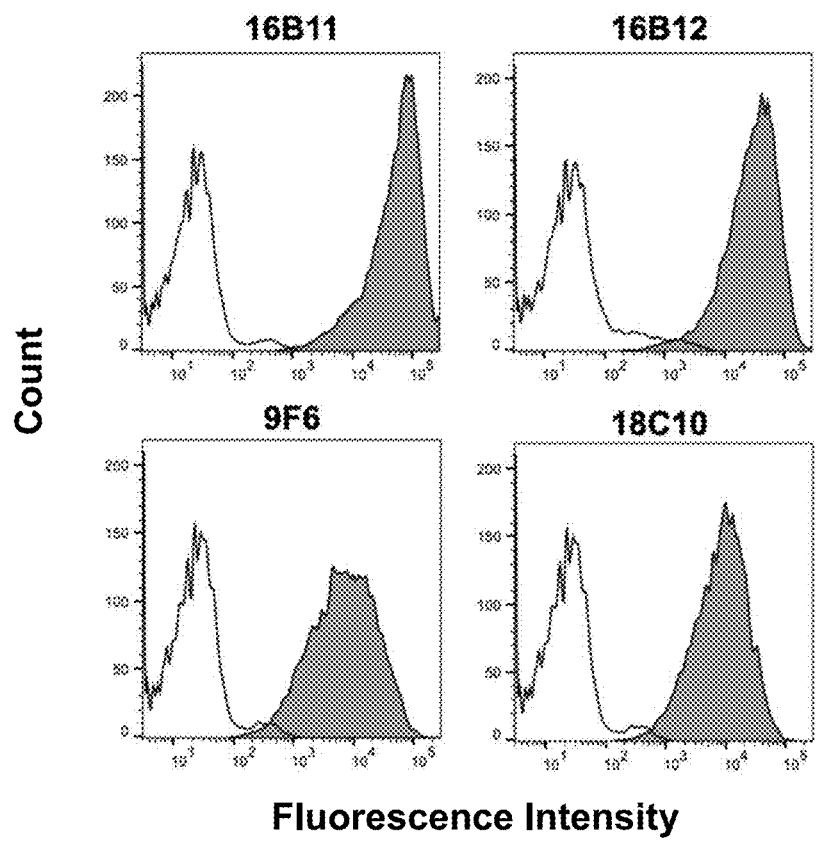
FIG. 1-1 illustrates results of measurement with flow cytometry of a binding of anti-TSPAN8 antibodies (16B11, 16B12, 9F6 and 18C10) to KM-291-As. In the drawing, 16B11, 16B12, 9F6 and 18C10 indicate the names of the antibodies. The abscissa of the drawing indicates fluorescence intensity, and the ordinate indicates the cell count. In the drawing, a white area indicates the binding of a negative control antibody, and a dark gray area indicates the binding of the anti-TSPAN8 antibody.

The present invention will be described in detail below.
<Definitions>
Terms used herein have the meaning commonly used by those skilled in the art in this technical field unless particularly specified below.

An antibody (or immunoglobulin) refers to a glycoprotein having a four-chain structure of a symmetric Y-shaped structure consisting of two heavy chains having a single sequence and two light chains having a single sequence. An antibody is divided into five classes IgG, IgM, IgA, IgD and IgE. The basic structure of an antibody molecule is common among the classes, and two heavy chains having a molecular weight of 50,000 to 70,000 and two light chains having a molecular weight of 20,000 to 30,000 are bonded through a disulfide bond or a noncovalent bond to form an antibody molecule having the Y-shaped four chain structure having a molecular weight of 150,000 to 190,000. A heavy chain consists of a polypeptide chain usually comprising about 440 amino acids, has a structure characteristic to each class, and is designated as Igγ, Igμ, Igα, Igδ and Igε respectively corresponding to IgG, IgM, IgA, IgD and IgE. Besides, IgG is further divided into subclasses IgG1, IgG2, IgG3 and IgG4, and heavy chains corresponding to these subclasses are respectively designated as Igγ1, Igγ2, Igγ3 and Igγ4. A light chain consists of a polypeptide chain usually comprising about 220 amino acids, is known to be divided into L light chain and K light chain, which are respectively designated as Igλ, and Igκ. The two types of light chains can pair with any type of heavy chains.

A heavy chain has four (five in Igμ and Igε) intrachain disulfide bonds of an antibody molecule, and a light chain has two intrachain disulfide bonds, and one loop is formed with every 100 to 110 amino acid residues. The three-dimensional structure is similar among loops, and a constituent unit is designated as a domain. In both a heavy chain and a light chain, a domain positioned at the N-terminal is designated as a variable region, which is known to have a variety of amino acid sequences even when the antibody is produced from the same class (or subclass) of animals of the same species, and to be involved in binding specific to an antibody-antigen bond. An amino acid sequence of a domain on the C-terminal side downstream from the variable region is substantially constant in each class or subclass, and this domain is designated as a constant region. A heavy chain has, from the N-terminal toward the C-terminal, a heavy chain variable region (VH) and a heavy chain constant region (CH). The CH is further divided into three domains of CH1 domain, CH2 domain and CH3 domain disposed in the stated order from the N-terminal side. A light chain has, from the N-terminal toward the C-terminal, a light chain variable region (VL) and a light chain constant region (CL).

Three complementarity determining regions (CDRs) present in each of the VH and VL are very largely varied in an amino acid sequence, and makes contribution to variability of the variable regions. The CDRs are regions present at the N-terminal of each of the heavy chain and the light chain in the order of CDR1, CDR2 and CDR3 and consisting of about 5 to 10 amino acid residues, and form an antigen-binding site. On the other hand, a portion excluding the CDRs in the variable region is designated as a frame work region (FR), which includes FR1 to FR4, and change of the amino acid sequence is comparatively small among these.

Treatment of the antibody with the proteolytic enzyme papain gives three antibody fragments. The two fragments on the N-terminal side are designated as Fab (antigen-binding fragments; fragment, antigen binding) regions. Herein, a "Fab region" refers to a region consisting of the VH and the CH1 domain of the heavy chain and the light chain (including the VL and the CL), which binds to an antigen at a tip portion in an antigen-binding site formed by the Fab region. Herein, the term "heavy chain fragment" refers to a fragment consisting of the VH and the CH1 domain of the heavy chain included in the Fab region.

Further, the fragment at the C-terminal side is designated as a Fc (crystallizable fragment; fragment, crystallizable) region. Herein, the term "Fc polypeptide" refers to a polypeptide consisting of the CH2 domain and the CH3 domain of the heavy chain, and the term "Fc region" refers to a complex consisting of two Fc polypeptides.

The heavy chain fragment and the Fc polypeptide are linked to each other through a portion designated as a hinge region. Besides, the two heavy chains of the antibody are disulfide bonded to each other in the hinge region.

Herein, the term "antigen" is used in a commonly used sense and is particularly used as a term for a molecule or a part of a molecule to which an antigen-binding protein such as an antibody or an antigen-binding fragment can specifically bind. The antigen can be a molecule such as proteins and nucleic acids. One antigen may have one or more epitopes capable of interacting with different antibodies and the like.

Herein, the "epitope" or "antigen determinant" means a specific structural unit of an antigen that an antigen-binding protein recognizes and binds to, and includes any determinant that can be bound by an antigen-binding protein such as antibodies or T-cell receptors. Epitope determinants can include chemically active surface groups of molecules such as amino acids, sugar side chains, phosphoryl groups, or sulfonyl groups and can have specific three-dimensional structural features and/or specific charge features. When the antigen is a protein, it contains a specific amino acid that directly contacts with an antibody or the like. In general, antibodies specific to a particular target antigen preferentially recognize epitopes on the target antigen in a complex mixture of proteins and/or macromolecules. Epitopes often consist of surface-contactable amino acid residues and/or sugar side chains, usually consisting of a sequence of 6 to 10 amino acids or 5 to 8 monosaccharides. Epitopes may have unique three-dimensional structural characteristics and unique charge characteristics. Epitopes may include amino acid residues that are directly involved in binding and other amino acid residues that are not directly involved in binding. An epitope that an antigen-binding protein binds to can be identified using methods well known to those skilled in the art, such as mass spectrometry (e.g., hydrogen/deuterium exchange mass spectrometry (HDX-MS)), alanine scanning mutagenesis, crystal analysis, and peptide competition.

Herein, the term "competition" or "compete" means that, when two or more antibodies are added to a reaction solution simultaneously or continuously, one antibody prevents the other antibody from binding to an antigen, resulting in a reduction in binding ability of the other antibody to the antigen.

Herein, the term "antigen-binding fragment" refers to a molecule having antigen binding activity derived from an antibody, and including at least one polypeptide chain. Representative examples of the antigen-binding fragment include a single-chain variable region fragment (scFv), a Fab fragment, a Fab' fragment and a F(ab')2 fragment. The scFv is a monovalent antigen-binding fragment including the VH and the VL linked through a linker. The Fab fragment is a monovalent antigen-binding fragment constituted by a fragment including the light chain and the VH and the CH1 domain of the heavy chain. The Fab' fragment is a monovalent antigen-binding fragment constituted by a fragment containing the light chain, the VH and the CH1 domain of the heavy chain and a part of the hinge region, and in this part of the hinge region, a cysteine residue constituting a S-S bond between the heavy chains is included. The F(ab')2 fragment is a bivalent molecule in which the Fab' fragments are linked to each other through a disulfide bond. Monovalence means that one antigen binding site is included, and bivalence means that two antigen binding sites are included.

Herein, the term "scFv region" refers to a region including a monovalent antigen-binding fragment including the VH and the VL linked to each other through a linker.

A one-armed antibody is also a kind of antigen-binding fragment. The one-armed antibody includes one Fab region and one Fc region and has a structure in which the heavy chain fragment of the Fab region is linked to one of the two Fc polypeptides of the Fc region. In one aspect, the one-armed antibody includes one heavy chain (the VH, the CH1 domain, the hinge region, and the Fc polypeptides (the CH2 domain and the CH3 domain)), one light chain (the VL and the CL), and Fc polypeptides.

Herein, the term "multispecific antibody" refers to an antibody capable of specifically binding to two or more different antigens and is, for example, called a bispecific antibody or a trispecific antibody, depending on the number of antigens to be bound. Multispecific antibodies include a complex of two or more antibodies and/or antigen-binding fragments each capable of binding to a different antigen. The "antibodies" used herein includes multispecific antibodies, unless otherwise specified in the context.

Herein, the term "bispecific antibody" refers to an antibody capable of specifically binding to two different antigens. The term "anti-TSPAN8/anti-CD3 bispecific antibody" means a bispecific antibody having binding activity to TSPAN8 and binding activity to CD3.

Herein, the term "human antibody" refers to an antibody having a human immunoglobulin amino acid sequence. Herein, the term "humanized antibody" refers to an antibody in which a part of, most of, or all of amino acid residues excluding the CDRs have been replaced with amino acid residues derived from a human immunoglobulin molecule. A humanizing method is not especially limited, and a humanized antibody can be produced, for example, referring to U.S. Pat. Nos. 5,225,539, 6,180,370, and the like.

An amino acid residue number of the antibody used herein can be prescribed by specifying Kabat numbering or EU index (Kabat et al., Sequences of Proteins of Immunological Interest, 5th Ed., 1991, NIH Publication No. 91-3242) in accordance with these numbering systems.

Herein, the term "first" or "second" is used for conveniently distinguishing two or more types of portions. Use of such a term does not intend to impart a specific order or meaning unless clearly mentioned.

Herein, the term "link" or "linked" means that a plurality of components (such as a Fab region and a Fc polypeptide) are linked to one another directly or through a plurality of intermediaries (such as a peptide linker). Herein, the term "peptide linker" means one or more arbitrary amino acid residues that can be introduced by genetic engineering for linking variable regions to each other. A length of the peptide linker used in the present invention is not especially limited, and can be appropriately selected depending on purpose by those skilled in the art.

Herein, the term "identity" means a value of identity obtained using EMBOSS Needle (Nucleic Acids Res., 2015, Vol. 43, p. W580-W584) with parameters prepared as default. The parameters are:
Gap Open Penalty=10
Gap Extend Penalty=0.5
Matrix=EBLOSUM62
End Gap Penalty=false.

Herein, the "subject" means a human or other animals in need of prevention or treatment. In some embodiments, it is a human in need of prevention or treatment.

<Anti-TSPAN8/anti-CD3 Bispecific Antibody of Invention>

The present invention provides a bispecific antibody that binds to TSPAN8 and CD3 (referred to also as the "anti-TSPAN8/anti-CD3 bispecific antibody") as follows:

A bispecific antibody that binds to TSPAN8 and CD3, comprising:
  (a) a Fab region of an anti-TSPAN8 antibody consisting of: a heavy chain fragment comprising a heavy chain variable region of the anti-TSPAN8 antibody; and a light chain comprising a light chain variable region of the anti-TSPAN8 antibody;
  (b) an anti-CD3-scFv region comprising a heavy chain variable region and a light chain variable region of an anti-CD3 antibody; and
  (c) a Fc region consisting of a first Fc polypeptide linked to the heavy chain fragment of the Fab region (a) and a second Fc polypeptide linked to the anti-CD3-scFv region (b).

The anti-TSPAN8/anti-CD3 bispecific antibody of the present invention has a structure including one Fab region of a first antibody, a scFv region of a second antibody, and one Fc region. An antibody having such a structure is designated as a "bottle-opener antibody" (International Publication No. 2014/110601). In one aspect, the anti-TSPAN8/anti-CD3 bispecific antibody of the present invention is a human antibody or a humanized antibody.

The anti-TSPAN8/anti-CD3 bispecific antibody of the present invention comprises, as the Fab region, an anti-TSPAN8 antibody Fab region comprising a heavy chain fragment comprising a heavy chain variable region of an anti-TSPAN8 antibody, and a light chain comprising a light chain variable region of the anti-TSPAN8 antibody.

In one aspect, the heavy chain variable region of the anti-TSPAN8 antibody comprises a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6. The light chain variable region of the anti-TSPAN8 antibody comprises a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8.

In one aspect, the heavy chain variable region of the anti-TSPAN8 antibody comprises a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10. The light chain variable region of the anti-TSPAN8 antibody comprises a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12.

In one aspect, the heavy chain variable region of the anti-TSPAN8 antibody consists of an amino acid sequence from amino acid positions 1 to 121 of SEQ ID NO: 6, and the light chain variable region of the anti-TSPAN8 antibody consists of an amino acid sequence from amino acid positions 1 to 107 of SEQ ID NO: 8.

In one aspect, the heavy chain variable region of the anti-TSPAN8 antibody consists of an amino acid sequence from amino acid positions 1 to 121 of SEQ ID NO: 10, and the light chain variable region of the anti-TSPAN8 antibody consists of an amino acid sequence from amino acid positions 1 to 107 of SEQ ID NO: 12.

As a heavy chain constant region used as the origin of the CH1 domain of the heavy chain fragment of the Fab region of the anti-TSPAN8 antibody, any one of the constant regions Igγ, Igμ, Igα, Igδ and Igε can be selected. The Igγ can be selected from, for example, Igγ1, Igγ2, Igγ3 and Igγ4. In one aspect, the heavy chain fragment of the Fab region of the anti-TSPAN8 antibody comprises a CH1 domain derived from human Igγ1 constant region.

As the CL of the light chain of the Fab region of the anti-TSPAN8 antibody, either of the constant regions Igλ, and Igκ can be selected. In one aspect, the Fab region of the anti-TSPAN8 antibody comprises a CL that is an Igκ constant region. In one aspect, the light chain of the anti-TSPAN8 antibody comprises a CL that is an Igκ constant region.

In one aspect, the Fab region of the anti-TSPAN8 antibody consists of a heavy chain fragment consisting of an amino acid sequence from amino acid positions 1 to 219 of SEQ ID NO: 6, and a light chain consisting of an amino acid sequence of SEQ ID NO: 8. In one aspect, the Fab region of the anti-TSPAN8 antibody consists of a heavy chain fragment consisting of an amino acid sequence from amino acid positions 1 to 219 of SEQ ID NO: 10, and a light chain consisting of an amino acid sequence of SEQ ID NO: 12.

The anti-TSPAN8/anti-CD3 bispecific antibody of the present invention comprises, as the scFv region, an anti-CD3-scFv region comprising a heavy chain variable region and a light chain variable region of an anti-CD3 antibody. In the anti-TSPAN8/anti-CD3 bispecific antibody of the present invention, a scFv region of an anti-CD3 antibody known in this technical field, or a scFv region of an anti-CD3 antibody produced based on sequence information on a heavy chain variable region and a light chain variable region of an anti-CD3 antibody known in this technical field may be used. As the known anti-CD3 antibody, clones OKT3, UTCH1, L2K, TR66 and the like are known, and sequences of these are used as bispecific antibodies (Pharmacol. Ther., 2018, Vol. 182, p. 161-175).

In one aspect, the heavy chain variable region of the anti-CD3 antibody comprises a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14. The light chain variable region of the anti-CD3 antibody comprises a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14.

In one aspect, the heavy chain variable region of the anti-CD3 antibody consists of an amino acid sequence from amino acid positions 1 to 125 of SEQ ID NO: 14, and the light chain variable region of the anti-CD3 antibody consists of an amino acid sequence from amino acid positions 146 to 254 of SEQ ID NO: 14.

In the anti-CD3-scFv region, the type and the length of a peptide linker linking the heavy chain variable region and the light chain variable region of the anti-CD3 antibody are not especially limited but can be appropriately selected by those skilled in the art. The length is preferably 5 or more amino acids (and an upper limit is not especially limited but is usually 30 or less amino acids, and preferably 20 or less amino acids), and particularly preferably 15 amino acids. As the peptide linker, for example, a glycine-serine linker (GS linker) or a glycine-lysine-proline-glycine-serine linker (GKPGS linker) can be used. Examples of such a linker include the following:
 Ser;
 Gly-Ser;
 Gly-Gly-Ser;
 Ser-Gly-Gly;
 Gly-Gly-Gly-Ser (SEQ ID NO: 15);
 Ser-Gly-Gly-Gly (SEQ ID NO: 16);
 Gly-Gly-Gly-Gly-Ser (SEQ ID NO: 17);
 Ser-Gly-Gly-Gly-Gly (SEQ ID NO: 18);
 Gly-Gly-Gly-Gly-Gly-Ser (SEQ ID NO: 19);
 Ser-Gly-Gly-Gly-Gly-Gly (SEQ ID NO: 20);
 Gly-Gly-Gly-Gly-Gly-Gly-Ser (SEQ ID NO: 21);
 Ser-Gly-Gly-Gly-Gly-Gly-Gly (SEQ ID NO: 22);
 (Gly-Gly-Gly-Gly-Ser)n;
 (Ser-Gly-Gly-Gly-Gly)n;
 Gly-Lys-Pro-Gly-Ser (SEQ ID NO: 23); and
 (Gly-Lys-Pro-Gly-Ser)n.

In the above, n indicates an integer of 1 or more. The length and the sequence of the peptide linker can be appropriately selected depending on purpose by those skilled in the art.

In one aspect, the anti-CD3-scFv region consists of an amino acid sequence from amino acid positions 1 to 254 of SEQ ID NO: 14.

In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and a polypeptide in which an anti-CD3-scFv region comprising a heavy chain variable region of an anti-CD3-antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID No: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide. In one aspect, the anti-TSPAN8/anti-CD3 bispecific antibody of the present invention comprises: a heavy chain of an anti-TSPAN8 antibody in which a heavy chain fragment of the anti-TSPAN8 antibody of a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12; and a polypeptide in which an anti-CD3-scFv region comprising a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide.

In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; a light chain of an anti-TSPAN8 antibody comprising a light chain variable region consisting of an amino acid sequence from amino acid positions 1 to 107 of SEQ ID NO: 8; and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of an anti-CD3 antibody consisting of an amino acid sequence from amino acid positions 146 to 254 of SEQ ID NO: 14 is linked to a second Fc polypeptide. In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide; a light chain of an anti-TSPAN8 antibody comprising a light chain variable region consisting of an amino acid sequence from amino acid positions 1 to 107 of SEQ ID NO: 12; and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of the anti-CD3 antibody consisting of an amino acid sequence from amino acid positions 146 to 254 of SEQ ID NO: 14 is linked to a second Fc polypeptide.

In the anti-TSPAN8/anti-CD3 bispecific antibody of the present invention, as a heavy chain constant region used as the origin of the first Fc polypeptide and the second Fc polypeptide contained in the Fc region, any one of the constant regions Igγ, Igμ, Igα, Igδ and Igε can be selected. The Igγ can be selected from, for example, Igγ1, Igγ2, Igγ3 and Igγ4. In one aspect, the first Fc polypeptide and the second Fc polypeptide are a Fc polypeptide derived from human Igγ1 constant region.

The Fc region of the anti-TSPAN8/anti-CD3 bispecific antibody of the present invention may contain mutation that deteriorates antibody-dependent cytotoxicity (ADCC) or complement-dependent cytotoxicity (CDC). L234A is replacement of leucine with alanine at amino acid position 234 in human Igγ1 constant region according to EU index. L235A is replacement of leucine with alanine at amino acid position 235 in human Igγ1 constant region according to EU index. The amino acid mutation of L234A and L235A of human Igγ1 constant region is designated as "LALA mutation". This mutation is known to deteriorate antibody-dependent cytotoxicity and complement-dependent cytotoxicity of an antibody (Mol. Immunol., 1992, Vol. 29, p. 633-639; and J. Immunol., 2000, Vol. 164, p. 4178-4184).

The Fc region of the anti-TSPAN8/anti-CD3 bispecific antibody of the present invention may further contain mutation based on another known technique. For example, the Fc region may contain N297G mutation (Protein cell, 2018, Vol. 9, p. 63-73) or mutation based on knobs-into-holes technique (hereinafter also referred to as "knobs-into-holes mutation"). According to knobs-into-holes technique, an amino acid side chain present in the CH3 region of one heavy chain is replaced with a larger side chain (knob), and an amino acid side chain present in the CH3 region of another heavy chain is replaced with a smaller side chain (hole), and thus, heterodimerization of the heavy chains is accelerated with the knob disposed within the hole, and in this manner, a heterodimerized antibody molecule of interest can be efficiently obtained (Nature, 1994, Vol. 372, p. 379-383; Nature Biotech, 1998, Vol. 16, p. 677-681; J. Mol. Biol., 1997, Vol. 270, p. 26-35; and Proc. Natl. Acad. Sci. USA, 2013, Vol. 110, p. E2987-E2996).

In one aspect, the anti-TSPAN8/anti-CD3 bispecific antibody of the present invention comprises a FC region containing amino acid mutation L234A and L235A (LALA mutation). In one aspect, the anti-TSPAN8/anti-CD3 bispecific antibody of the present invention comprises a Fc region containing N297G mutation. In one aspect, the anti-TSPAN8/anti-CD3 bispecific antibody of the present invention comprises a Fc region containing knobs-into-holes mutation. In one aspect, the anti-TSPAN8/anti-CD3 bispecific antibody of the present invention comprises a FC region containing one or more mutations of amino acid mutation L234A and L235A (LALA mutation), N297G mutation, and knobs-into-holes mutation. In one aspect, the anti-TSPAN8/anti-CD3 bispecific antibody of the present invention comprises a FC region containing amino acid mutation L234A and L235A (LALA mutation), N297G mutation, and Knobs-into-holes mutation. In one aspect, the knobs-into-holes mutation contained in the anti-TSPAN8/anti-CD3 bispecific antibody of the present invention is T366W mutation in one Fc polypeptide included in the Fc region, and T366S, L368A and Y407V mutations (see International Publication No. 1998/050431) in another Fc polypeptide included in the Fc region.

In one aspect, the anti-TSPAN8/anti-CD3 bispecific antibody of the present invention comprises a Fc region consisting of a first Fc polypeptide consisting of an amino acid sequence from amino acid positions 235 to 451 of SEQ ID NO: 6 and a second Fc polypeptide consisting of an amino acid sequence from amino acid positions 270 to 486 of SEQ ID NO: 14.

Herein, the amino acid mutations such as LALA mutation, N297G mutation and knobs-into-holes mutation are described based on amino acid positions in human Igγ1 constant region according to EU index. For example, as described above, L234A is replacement of leucine with alanine at amino acid position 234 in human Igγ1 constant region according to EU index.

In the anti-TSPAN8/anti-CD3 bispecific antibody of the present invention, the heavy chain fragment comprising the heavy chain variable region of the anti-TSPAN8 antibody may be linked to the Fc polypeptide (the first Fc polypeptide) through a hinge region to form the heavy chain of the anti-TSPAN8 antibody.

Besides, in the anti-TSPAN8/anti-CD3 bispecific antibody of the present invention, the anti-CD3-scFv region may be linked to the Fc polypeptide (the second Fc polypeptide) through a hinge region.

In one aspect, the anti-TSPAN8/anti-CD3 bispecific antibody of the present invention comprises a heavy chain of an anti-TSPAN8 antibody in which a heavy chain fragment comprising a heavy chain variable region of the anti-TSPAN8 antibody is linked to a first Fc polypeptide through a hinge region. In one aspect, the anti-TSPAN8/anti-CD3 bispecific antibody of the present invention comprises a polypeptide in which an anti-CD3-scFv region is linked to a second Fc polypeptide through a hinge region. In one aspect, the anti-TSPAN8/anti-CD3 bispecific antibody of the present invention comprises a heavy chain of an anti-TSPAN8 antibody in which a heavy chain fragment comprising a heavy chain variable region of the anti-TSPAN8 antibody is linked to a first Fc polypeptide through a hinge region, and a polypeptide in which an anti-CD3-scFv region is linked to a second Fc polypeptide through a hinge region.

In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide through a hinge region; a light chain of an anti-TSPAN8 antibody comprising a light chain variable region comprising a CDR1 consisting of an amino acid sequence from amino acid positions 24 to 34 of SEQ ID NO: 8, CDR2 consisting of an amino acid sequence from amino acid positions 50 to 56 of SEQ ID NO: 8, and a CDR3 consisting of an amino acid sequence from amino acid positions 89 to 96 of SEQ ID NO: 3; and a polypeptide in which an anti-CD3-scFv region comprising a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide through a hinge region. In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide through a hinge region; a light chain of an anti-TSPAN8 antibody comprising a light chain variable region comprising a CDR1 consisting of an amino acid sequence from amino acid positions 24 to 34 of SEQ ID NO: 12, CDR2 consisting of an amino acid sequence from amino acid positions 50 to 56 of SEQ ID NO: 12, and a CDR3 consisting of an amino acid sequence from amino acid positions 89 to 96 of SEQ ID NO: 12; and a polypeptide in which an anti-CD3-scFv region comprising a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14 is linked to a second Fc polypeptide through a hinge region.

In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide through a hinge region; a light chain of an anti-TSPAN8 antibody comprising a light chain variable region consisting of an amino acid sequence from amino acid positions 1 to 107 of SEQ ID NO: 8; and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of an anti-CD3 antibody consisting of an amino acid sequence from amino acid positions 146 to 254 of SEQ ID NO: 14 is linked to a second Fc polypeptide through a hinge region. In one aspect, the anti-TSPAN8/anti-CD3 bispecific antibody of the present invention comprises: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide through a hinge region; a light chain of an anti-TSPAN8 antibody comprising a light chain variable region consisting of an amino acid sequence from amino acid positions 1 to 107 of SEQ ID NO: 12; and a polypeptide in which an anti-CD3-scFv region comprising a heavy chain variable region of an anti-CD3 antibody consisting of an amino acid sequence from amino acid positions 1 to 125 of SEQ ID NO: 14 and a light chain variable region of the anti-CD3 antibody consisting of an amino acid sequence from amino acid positions 146 to 254 of SEQ ID NO: 14 is linked to a second Fc polypeptide through a hinge region.

In one aspect, a heavy chain of an anti-TSPAN8 antibody in which a heavy chain fragment of the anti-TSPAN8 antibody including a heavy chain variable region of the anti-TSPAN8 antibody is linked to a first Fc polypeptide through a hinge region has an amino acid sequence of SEQ ID NO: 6 or 10. In one aspect, a heavy chain of an anti-TSPAN8 antibody in which a heavy chain fragment of the anti-TSPAN8 antibody including a heavy chain variable region of the anti-TSPAN8 antibody is linked to a first Fc polypeptide through a hinge region has an amino acid sequence of SEQ ID NO: 6. In one aspect, a light chain of an anti-TSPAN8 antibody consists of an amino acid sequence of SEQ ID NO: 8 or 12. In one aspect, a light chain of an anti-TSPAN8 antibody consists of an amino acid sequence of SEQ ID NO: 8. In one aspect, a polypeptide in which an anti-CD3-scFv region is linked to a second Fc polypeptide through a hinge region has an amino acid sequence of SEQ ID NO: 14. In one aspect, the anti-TSPAN8/anti-CD3 bispecific antibody of the present invention comprises a heavy chain of an anti-TSPAN8 antibody, consisting of an amino acid sequence of SEQ ID NO: 6 or 10, in which a heavy chain fragment of the anti-TSPAN8 antibody including a heavy chain variable region of the anti-TSPAN8 antibody and a light chain of an anti-TSPAN8 antibody consisting of the amino acid sequence of SEQ ID NO: 8 or 12 are linked to a first polypeptide, and a polypeptide, consisting of an amino acid sequence of SEQ ID NO: 14, in which an anti-CD3-scFv region is linked to a second Fc polypeptide. In one aspect, the anti-TSPAN8/anti-CD3 bispecific antibody of the present invention comprises a heavy chain of an anti-TSPAN8 antibody, consisting of an amino acid sequence of SEQ ID NO: 6, in which a heavy chain fragment of a heavy chain variable region of the anti-TSPAN8 antibody is linked to a first Fc polypeptide, and a polypeptide, consisting of an amino acid sequence of SEQ ID NO: 14, in which an anti-CD3-scFv region is linked to a second Fc polypeptide.

In one aspect, the anti-TSPAN8/anti-CD3 bispecific antibody of the present invention is a bispecific antibody comprising a heavy chain of an anti-TSPAN8 antibody in which a heavy chain fragment of the anti-TSPAN8 antibody consisting of an amino acid sequence of SEQ ID NO: 6 is linked to a first Fc polypeptide, a light chain of an anti-TSPAN8 antibody consisting of an amino acid sequence of SEQ ID NO: 8, and a polypeptide in which an anti-CD3-scFv region consisting of an amino acid sequence of SEQ ID NO: 14 is linked to a second Fc polypeptide.

Here, the term "post-translational modification" refers to that an antibody expressed in a cell is modified after translation. Examples of the post-translational modification include modification such as pyroglutamylation, glycosylation, oxidation, deamidation or glycation of glutamine or glutamic acid at a heavy chain N-terminal, and lysine deletion by cutting lysine at a heavy chain C-terminal with carboxypeptidase. It is known that such post-translational modification is caused in various antibodies (J. Pharm. Sci., 2008, Vol. 97, p. 2426-2447).

In one aspect, the anti-TSPAN8/anti-CD3 bispecific antibody of the present invention may be post-translationally modified. In one aspect, the post-translational modification is pyroglutamylation at the N-terminal of the heavy chain variable region and/or lysine deletion at the heavy chain C-terminal. It is known in this technical field that the post-translational modification by pyroglutamylation at the N-terminal or lysine deletion at the C-terminal does not affect the activity of the antibody (Analytical Biochemistry, 2006, Vol. 348, p. 24-39).

The anti-TSPAN8/anti-CD3 bispecific antibody of the present invention binds to human TSPAN8 (GENBANK Accession No. NM 004616.2) and human CD3εδ complex protein (CD3ε: GENBANK Accession No. NM 000733.3, CD3δ: GENBANK Accession No. NM 000732.4 or NM 001040651.1). It can be checked by a known binding activity measurement method whether the antibody binds to human TSPAN8 and human CD3εδ complex protein. Examples of a method for measuring binding activity include Enzyme-Linked ImmunoSorbent Assay (ELISA) and flow cytometry. When ELISA is employed, for example, a method described in Example 8 can be employed, and when flow cytometry is employed, for example, a method described in Example 1 can be employed.

The anti-TSPAN8/anti-CD3 bispecific antibody of the present invention can be produced by those skilled in the art by a method known in this technical field on the basis of sequence information and the like on an anti-TSPAN8 antibody, and the heavy chain variable region and the light chain variable region of the anti-CD3-scFv region disclosed herein. Besides, the anti-CD3-scFv region of the anti-TSPAN8/anti-CD3 bispecific antibody of the present invention can be produced by those skilled in the art by a method known in this technical field based on sequence information and the like on the heavy chain variable region and the light chain variable region of a known anti-CD3 antibody. In one aspect, the anti-TSPAN8/anti-CD3 bispecific antibody of the present invention is a humanized antibody or a human antibody. In production of a humanized antibody, a back mutation may be appropriately introduced by employing a method well known to those skilled in the art (Bioinformatics, 2015, Vol. 31, p. 434-435). The anti-TSPAN8/anti-CD3 bispecific antibody of the present invention can be produced by, but not especially limited to, for example, a method described later in <Method for Producing Bispecific Antibody of Invention and Bispecific Antibody of Invention produced by the Method>.

<Polynucleotide of Bispecific Antibody of Invention>

The present invention also provides polynucleotides described below that can be used for producing the anti-TSPAN8/anti-CD3 bispecific antibody of the present invention (also referred to as the "polynucleotide of the bispecific antibody of the present invention).

(1) A polynucleotide comprising a nucleotide sequence encoding a heavy chain of an anti-TSPAN8 antibody comprising a heavy chain fragment of the anti-TSPAN8 antibody and a first Fc polypeptide;

(2) a polynucleotide comprising a nucleotide sequence encoding a light chain of an anti-TSPAN8 antibody; and (3) a polynucleotide comprising a nucleotide sequence encoding a polypeptide comprising an anti-CD3-scFv region and a polypeptide comprising a second Fc polypeptide.

In one aspect of the polynucleotide (1) described above, the polynucleotide of the bispecific antibody of the present invention is a polynucleotide selected from the following (a) and (b):

(a) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO. 6 is linked to a first Fc polypeptide; and (b) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10 is linked to a first Fc polypeptide.

In one aspect of the polynucleotide (1) described above, the polynucleotide of the bispecific antibody of the present invention is a polynucleotide selected from the following (a) and (b):

(a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; and (b) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide.

In one aspect of the polynucleotide (1) described above, the polynucleotide of the bispecific antibody of the present invention is a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide.

In one aspect of the polynucleotide (2) described above, the polynucleotide of the bispecific antibody of the present invention is a polynucleotide selected from the following (a) and (b):

(a) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; and (b) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 12.

In one aspect of the polynucleotide (2) described above, the polynucleotide of the bispecific antibody of the present invention is a polynucleotide selected from the following (a) and (b):

(a) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8; and (b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12.

In one aspect of the polynucleotide (2) described above, the polynucleotide of the bispecific antibody of the present invention is a polynucleotide comprising a nucleotide sequence encoding a light chain of an anti-TSPAN8 antibody consisting of an amino acid sequence of SEQ ID NO: 8.

In one aspect of the polynucleotide (3) described above, the polynucleotide of the bispecific antibody of the present invention is a polynucleotide as follows:

A polynucleotide comprising a nucleotide sequence encoding a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect of the polynucleotide (3) described above, the polynucleotide of the bispecific antibody of the present invention is a polynucleotide as follows:

A polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.

In one aspect of the polynucleotide (3) described above, the polynucleotide of the bispecific antibody of the present invention is a polynucleotide comprising a nucleotide sequence encoding a polypeptide in which an anti-CD3-scFv region consisting of an amino acid sequence of SEQ ID NO: 14 is linked to a second Fc polypeptide.

The polynucleotide of the bispecific antibody of the present invention can be produced by those skilled in the art based on the nucleotide sequence thereof by employing a method known in this technical field. For example, the polynucleotide of the bispecific antibody of the present invention can be synthesized by employing a gene synthesis method known in this technical field. As the gene synthesis method, any of various methods known to those skilled in the art such as a synthesis method for an antibody gene described in International Publication No. 90/07861 can be employed.

<Expression Vector for Bispecific Antibody of Invention>

The present invention also provides an expression vector comprising polynucleotides described in the following (1) to (3) for the bispecific antibody of the present invention (referred to also as the "expression vector for the bispecific antibody of the present invention"). These polynucleotides may be contained respectively in different vectors, or a plurality of the polynucleotides may be contained in one vector.

(1) A polynucleotide comprising a nucleotide sequence encoding a heavy chain of an anti-TSPAN8 antibody in which a heavy chain fragment of the anti-TSPAN8 antibody is linked to a first Fc polypeptide;

(2) a polynucleotide comprising a nucleotide sequence encoding a light chain of an anti-TSPAN8 antibody; and (3) a polynucleotide comprising a nucleotide sequence encoding a polypeptide in which an anti-CD3-scFv region is linked to a polypeptide comprising a second Fc polypeptide.

In one aspect of the expression vector for the bispecific antibody of the present invention comprising the polynucleotide (1) described above, the expression vector comprises a polynucleotide selected from the following (a) and (b):

(a) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide; and (b) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide.

In one aspect of the expression vector for the bispecific antibody of the present invention comprising the polynucleotide (1) described above, the expression vector comprises a polynucleotide selected from the following (a) and (b):
(a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; and
(b) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide.

In one aspect of the expression vector for the bispecific antibody of the present invention comprising the polynucleotide (1) described above, the expression vector comprises a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide.

In one aspect of the expression vector for the bispecific antibody of the present invention comprising the polynucleotide (2) described above, the expression vector comprises a polynucleotide selected from the following (a) and (b):
(a) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; and
(b) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 12.

In one aspect of the expression vector for the bispecific antibody of the present invention comprising the polynucleotide (2) described above, the expression vector comprises a polynucleotide selected from the following (a) and (b):
(a) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8; and
(b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12.

In one aspect of the expression vector for the bispecific antibody of the present invention comprising the polynucleotide (2) described above, the expression vector comprises a polynucleotide comprising a nucleotide sequence encoding a light chain of an anti-TSPAN8 antibody consisting of an amino acid sequence of SEQ ID NO: 8.

In one aspect of the expression vector for the bispecific antibody of the present invention comprising the polynucleotide (3) described above, the expression vector comprises a polynucleotide as follows:
A polynucleotide comprising a nucleotide sequence encoding a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect of the expression vector for the bispecific antibody of the present invention comprising the polynucleotide (3) described above, the expression vector comprises a polynucleotide as follows:
A polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.

In one aspect of the expression vector for the bispecific antibody of the present invention comprising the polynucleotide (3) described above, the expression vector comprises a polynucleotide comprising a nucleotide sequence encoding a polypeptide in which an anti-CD3-scFv region consisting of an amino acid sequence of SEQ ID NO: 14 is linked to a second Fc polypeptide.

In one aspect, the expression vector for the bispecific antibody of the present invention is an expression vector comprising one or more polynucleotides selected from the following (a) to (e):
(a) a polynucleotide having a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide;
(b) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8;
(c) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide;

(d) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 12; and (e) a polynucleotide comprising a nucleotide sequence encoding a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect, the expression vector for the bispecific antibody of the present invention is an expression vector comprising one or more polynucleotides selected from the following (a) to (e):

(a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide;

(b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8;

(c) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide;

(d) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12; and (e) a polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.

In one aspect, the expression vector for the bispecific antibody of the present invention is an expression vector comprising one or more polynucleotides selected from the following (a) to (c):

(a) a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide;

(b) a polynucleotide comprising a nucleotide sequence encoding a light chain of an anti-TSPAN8 antibody consisting of an amino acid sequence of SEQ ID NO: 8; and (c) a polynucleotide comprising a nucleotide sequence encoding a polypeptide consisting of an amino acid sequence of SEQ ID NO: 14 in which an anti-CD3-scFv region is linked to a second Fc polypeptide.

The expression vector for the bispecific antibody of the present invention is not especially limited as long as it can produce the polynucleotide of the present invention in various host cells such as a eukaryotic cell (such as an animal cell, an insect cell, a plant cell or a yeast) and/or a prokaryotic cell (such as *E. coli*). Examples of the expression vector include a plasmid vector and a virus vector. As the plasmid vector, for example, pcDNA series (Thermo Fisher Scientific), pALTER(R)-MAX (Promega Corporation), pHEK293 Ultra Expression Vector (Takara Bio Inc.), pEE 6.4 or pEE 12.4 (Lonza Biologics) or the like can be used. As the virus vector, for example, a lentivirus, an adenovirus, a retrovirus, or an adeno-associated virus can be used. For example, when a lentivirus is used for introducing the polynucleotide of the present invention into a cell, pLVSIN-CMV/EF1α vector (Takara Bio Inc.), pLenti vector (Thermo Fisher Scientific) or the like can be used as the lentivirus. In one aspect, a vector used in the expression vector for the bispecific antibody of the present invention is pcDNA™ 3.4-TOPO(R) (Thermo Fisher Scientific) or pcDNA™ 3.1 (Thermo Fisher Scientific).

The expression vector for the bispecific antibody of the present invention can include a promoter operably linked to the polynucleotide of the bispecific antibody of the present invention. Examples of the promoter for expressing the polynucleotide of the bispecific antibody of the present invention in an animal cell include virus-derived promoters such as CMV, RSV and SV40, an actin promoter, an EF (elongation factor) 1α promoter, and a heat shock promoter. Examples of the promoter for expressing the polynucleotide of the bispecific antibody of the present invention in a bacterium (such as one belonging to the genus *Escherichia*) include a trp promoter, a lac promoter, a λPL promoter, and a tac promoter. Examples of the promoter for expressing the polynucleotide of the bispecific antibody of the present invention in a yeast include a GAL1 promoter, a GAL10 promoter, a PHO5 promoter, a PGK promoter, a GAP promoter, and an ADH promoter.

When an animal cell, an insect cell or a yeast is used as the host cell, the expression vector for the bispecific antibody of the present invention can include a start codon and a stop codon. In this case, an enhancer sequence, the 5'- and 3'-untranslated regions of a gene encoding the antibody of the present invention, or the heavy chain or light chain thereof, a secretory signal sequence, a splice joint, a polyadenylation site, a replicable unit or the like may be included. When *E. coli* is used as the host cell, the expression vector of the present invention can include a start codon, a stop codon, a terminator region, and a replicable unit. The expression vector of the present invention may include a drug selection marker gene usually used depending on purpose (such as a tetracycline resistance gene, an ampicillin resistance gene, a kanamycin resistance gene, a neomycin resistance gene, or a dihydrofolate reductase gene).

<Transformed Host Cell of Invention>

The present invention also provides a host cell transformed by the expression vector for the bispecific antibody of the present invention (also referred to as the "transformed host cell of the present invention"). The transformed host cell of the present invention may include one of or a plurality of polynucleotides for the bispecific antibody of the present invention described in the following (1) to (3) through transformation by the expression vector for the bispecific antibody of the present invention, and in one aspect, the transformed host cell of the present invention includes all of the polynucleotides described in the following (1) to (3):

(1) A polynucleotide comprising a nucleotide sequence encoding a heavy chain of an anti-TSPAN8 antibody in which a heavy chain fragment of the anti-TSPAN8 antibody is linked to a first Fc polypeptide;

(2) a polynucleotide comprising a nucleotide sequence encoding a light chain of an anti-TSPAN8 antibody; and (3) a polynucleotide comprising a nucleotide sequence encoding a polypeptide in which an anti-CD3-scFv region is linked to a polypeptide comprising a second Fc polypeptide.

A host cell to be transformed is not especially limited as long as it is suitable for the expression vector to be used, and can express an antibody or a fusion through transformation with the expression vector. Examples of the host cell to be transformed include various cells including conventional cells usually used in this technical field and artificially established cells (for example, animal cells (such as a CHO-K1 cell, an ExpiCHO-S(R) cell, a CHOK1SV cell, a CHO-DG44 cell, a HEK293 cell, and a NS0 cell), insect cells (such as Sf9), bacteria (such as those belonging to the genus *Escherichia*), and yeasts (such as those belonging to the genus *Saccharomyces* and the genus *Pichia*). In one aspect, the host cell of the present invention is a CHO-K1 cell or an ExpiCHO-S cell.

A method for transforming the host cell is not especially limited, and for example, a method usually employed by those skilled in the art such as the calcium phosphate method, the electroporation method or the lipofection method can be employed.

Selection of a transformed host cell can be performed by a method usually employed by those skilled in the art. As the selection method, for example, a drug selection method using a drug selection marker gene and a drug such as tetracycline, ampicillin, neomycin or hygromycin, or a cell isolation method such as a limiting dilution method, a single cell sorting method or a colony pick-up method can be employed.

In one aspect of the transformed host cell of the present invention comprising the polynucleotide (1) described above, the host cell comprises a polynucleotide selected from the following (a) and (b):

(a) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide; and (b) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide.

In one aspect of the transformed host cell of the present invention comprising the polynucleotide (1) described above, the host cell comprises a polynucleotide selected from the following (a) and (b):

(a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; and (b) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide.

In one aspect of the transformed host cell of the present invention comprising the polynucleotide (1) described above, the host cell comprises a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide.

In one aspect of the transformed host cell of the present invention comprising the polynucleotide (2) described above, the host cell comprises a polynucleotide selected from the following (a) and (b):

(a) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; and (b) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO:8, and a CDR3 consisting of an amino acid sequence from amino acid positions 89 to 96 of SEQ ID NO: 12.

In one aspect of the transformed host cell of the present invention comprising the polynucleotide (2) described above, the host cell comprises a polynucleotide selected from the following (a) and (b):
  (a) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8; and
  (b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12.

In one aspect of the transformed host cell of the present invention comprising the polynucleotide (2) described above, the host cell comprises a polynucleotide comprising a nucleotide sequence encoding a light chain of an anti-TSPAN8 antibody consisting of an amino acid sequence of SEQ ID NO: 8.

In one aspect of the transformed host cell of the present invention comprising the polynucleotide (3) described above, the host cell comprises a polynucleotide as follows:

A polynucleotide comprising a nucleotide sequence encoding a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect of the transformed host cell of the present invention comprising the polynucleotide (3) described above, the host cell comprises a polynucleotide as follows:

A polynucleotide comprising a nucleotide sequence encoding a polypeptide in which an anti-CD3-scFv region comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.

In one aspect of the transformed host cell of the present invention comprising the polynucleotide (3) described above, the host cell comprises a polynucleotide comprising a nucleotide sequence encoding a polypeptide in which an anti-CD3-scFv consisting of an amino acid sequence of SEQ ID NO: 14 is linked to a second Fc polypeptide.

In one aspect, the transformed host cell of the present invention is a host cell comprising one or more polynucleotides selected from the following (a) to (e):
  (a) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide;
  (b) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8;
  (c) a polynucleotide comprising a nucleotide sequence encoding a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide;
  (d) a polynucleotide comprising a nucleotide sequence encoding a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO:8, and a CDR3 consisting of an amino acid sequence from amino acid positions 89 to 96 of SEQ ID NO: 12; and
  (e) a polynucleotide comprising a nucleotide sequence encoding a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect, the transformed host cell of the present invention is a host cell comprising one or more polynucleotides selected from the following (a) to (e):
  (a) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide;
  (b) a polynucleotide comprising a nucleotide sequence encoding a light chain of an anti-TSPAN8 antibody comprising a light chain variable region consisting of an amino acid sequence from amino acid positions 1 to 107 of SEQ ID NO: 8;
(c) a polynucleotide comprising a nucleotide sequence encoding a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide;
(d) a polynucleotide comprising a nucleotide sequence encoding a light chain of an anti-TSPAN8 antibody comprising a light chain variable region consisting of an amino acid sequence from amino acid positions 1 to 107 of SEQ ID NO: 12; and
(e) a polynucleotide comprising a nucleotide sequence encoding a polypeptide in which an anti-CD3-scFv comprising a heavy chain variable region of an anti-CD3 antibody consisting of an amino acid sequence from amino acid positions 1 to 125 of SEQ ID NO: 14, and a light chain variable region of an anti-CD3 antibody consisting of an amino acid sequence from amino acid positions 146 to 254 of SEQ ID NO: 14 is linked to a second Fc polypeptide.

In one aspect, the transformed host cell of the present invention is a host cell comprising polynucleotides selected from the following (a) to (c):
(a) a polynucleotide comprising a nucleotide sequence encoding a heavy chain of an anti-TSPAN8 antibody consisting of an amino acid sequence of SEQ ID NO: 6 in which a heavy chain fragment of the anti-TSPAN8 antibody is linked to a first Fc polypeptide;
(b) a polynucleotide comprising a nucleotide sequence encoding a light chain of an anti-TSPAN8 antibody consisting of an amino acid sequence of SEQ ID NO: 8; and
(c) a polynucleotide comprising a nucleotide sequence encoding a polypeptide in which an anti-CD3-scFv consisting of an amino acid sequence of SEQ ID NO: 14 is linked to a second Fc polypeptide.

In one aspect, the transformed host cell of the present invention comprises a polynucleotide comprising a nucleotide sequence encoding a heavy chain of an anti-TSPAN8 antibody consisting of an amino acid sequence of SEQ ID NO: 6, a polynucleotide comprising a nucleotide sequence encoding a light chain of an anti-TSPAN8 antibody consisting of an amino acid sequence of SEQ ID NO: 8, and a polynucleotide comprising a nucleotide sequence encoding a polypeptide consisting of an amino acid sequence of SEQ ID NO: 14.

<Method for Producing Bispecific Antibody of Invention>

The present invention also provides a method for producing the anti-TSPAN8/anti-CD3 bispecific antibody of the present invention (referred to also as the "production method of the present invention"). The production method of the present invention can include a step of culturing the transformed host cell described in <Transformed Host Cell of Invention> to express the antibody in the cell or a culture supernatant, a method for collecting, isolating and purifying the antibody, and the like, but is not limited to such a method as long as the anti-TSPAN8/anti-CD3 bispecific antibody of the present invention can be produced.

The transformed host cell of the present invention can be cultured by a known method. Culture conditions such as a temperature, pH of a medium and a culture time can be appropriately selected by those skilled in the art. When the host cell is an animal cell, for example, MEM medium (Science, 1959, Vol. 130, p. 432-437) containing about 5 to 20% of fetal bovine serum, DMEM medium (Virol., 1959, Vol. 8, p. 396), RPMI-1640 medium (J. Am. Med. Assoc., 1967, Vol. 199, p. 519), 199 medium (Exp. Biol. Med., 1950, Vol. 73, p. 1-8) or the like can be used as the medium. The pH of the medium is, for example, about 6 to 8, and the culture is performed usually at about 30 to 40° C. for about 15 to 336 hours with aeration or stirring if necessary. When the host cell is an insect cell, for example, Grace's medium (Proc. Natl. Acad. Sci. USA., 1985, Vol. 82, p. 8404) containing fetal bovine serum or the like can be used as the medium. The pH of the medium is, for example, about 5 to 8, and the culture is performed usually at about 20 to 40° C. for about 15 to 100 hours with aeration or stirring if necessary. When the host cell is $E.$ $coli$ or a yeast, for example, a liquid medium containing a nutrition source is suitably used as the medium. A nutrient medium contains, for example, a carbon source, an inorganic nitrogen source, or an organic nitrogen source necessary for growth of the transformed host cell. Examples of the carbon source include glucose, dextran, soluble starch, and sucrose, examples of the inorganic nitrogen source or organic nitrogen source include ammonium salts, nitric acid salts, amino acids, a corn steep liquor, peptone, casein, a meat extract, a soybean cake, and a potato extract. Other nutrients (for example, inorganic salts (such as calcium chloride, sodium dihydrogen phosphate, and magnesium chloride) or vitamins), an antibiotic (such as tetracycline, neomycin, ampicillin, or kanamycin), or the like may be contained if desired. The pH of the medium is, for example, about 5 to 8. When the host cell is $E.$ $coli$, for example, LB medium, M9 medium (Molecular Cloning, Cold Spring Harbor Laboratory, Vol. 3, A2.2) or the like can be used as the medium. The culture is performed usually at about 14 to 43° C. for about 3 to 24 hours with aeration or stirring if necessary. When the host cell is a yeast, for example, Burkholder minimum medium (Proce. Natl. Acad. Sci. USA., 1980, Vol. 77, p. 4505) or the like can be used as the medium. The culture is performed usually at about 20 to 35° C. for about 14 to 144 hours with aeration or stirring if necessary. Through such culture, the anti-TSPAN8/anti-CD3 bispecific antibody of the present invention can be expressed.

The production method of the present invention can include, in addition to the step of culturing the transformed host cell of the present invention to express the anti-TSPAN8/anti-CD3 bispecific antibody, a step of collecting, isolating or purifying the anti-TSPAN8/anti-CD3 bispecific antibody from the transformed host cell. Examples of an isolating or purifying method include a method utilizing solubility such as salting-out or a solvent precipitation method, a method utilizing a difference in a molecular weight such as dialysis, ultrafiltration and gel filtration, a method utilizing charge such as ion exchange chromatography or hydroxyapatite chromatography, a method utilizing specific affinity such as affinity chromatography, a method utilizing a difference in hydrophobicity such as reverse phase high performance liquid chromatography, and a method utilizing a difference in an isoelectric point such as isoelectric focusing. In one aspect, the antibody secreted into a culture supernatant can be purified by various chromatographies such as column chromatography using a protein A column or a protein G column.

The anti-TSPAN8/anti-CD3 bispecific antibody of the present invention embraces an anti-TSPAN8/anti-CD3 bispecific antibody produced by the production method of the present invention.

<Pharmaceutical Composition or the like of Bispecific Antibody of Invention>

A pharmaceutical composition of the present invention embraces a pharmaceutical composition containing the anti-TSPAN8/anti-CD3 bispecific antibody of the present invention and a pharmaceutically acceptable excipient. The pharmaceutical composition of the present invention can be prepared by a method usually employed with an excipient usually used in this technical field, namely, a pharmaceutical excipient, a pharmaceutical carrier or the like. Examples of a dosage form of such a pharmaceutical composition include parenteral agents such as an injection and a drop, and administration can be performed by intravenous administration, subcutaneous administration, intraperitoneal administration or the like. In formulation, an excipient, a carrier, an additive or the like suitable to the dosage form can be used in a pharmaceutically acceptable range.

The pharmaceutical composition of the present invention can comprise a post-translationally modified product of the anti-TSPAN8/anti-CD3 bispecific antibody of the present invention. For example, a pharmaceutical composition comprising an antibody or the like containing both of or one of lysine deletion at a C-terminal and pyroglutamylation at a N-terminal can be embraced in the present invention.

In one aspect, the pharmaceutical composition of the present invention is a pharmaceutical composition comprising an anti-TSPAN8/anti-CD3 bispecific antibody of the present invention selected from the following (a) and (b) and/or a post-translationally modified product of the antibody:

(a) A bispecific antibody comprising a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 6, a CDR2 consisting of an amino acid sequence from amino acid positions 50 to 66 of SEQ ID NO: 6, and a CDR3 consisting of an amino acid sequence from amino acid positions 99 to 110 of SEQ ID NO: 6 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and a polypeptide in which an anti-CD3-scFv region, which comprises a heavy chain variable region of an anti-CD3-antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region of an anti-CD3 antibody comprising a CDR1 consisting of an amino acid sequence from amino acid positions 168 to 181 of SEQ ID No: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide; and (b) a bispecific antibody comprising a heavy chain of an anti-TSPAN8 antibody in which a heavy chain fragment of the anti-TSPAN8 antibody comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10 is linked to a first Fc polypeptide; a light chain of an anti-TSPAN8 antibody comprising a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12; and a polypeptide in which an anti-CD3-scFv region, which comprises a heavy chain variable region of an anti-CD3 antibody comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and light chain variable region of an anti-CD3 antibody comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14, is linked to a second Fc polypeptide.

In one aspect, the pharmaceutical composition of the present invention is a pharmaceutical composition comprising an anti-TSPAN8/anti-CD3 bispecific antibody of the present invention selected from the following (a) and (b) and/or a post-translationally modified product of the antibody:

(a) A bispecific antibody comprising: a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 6 is linked to a first Fc polypeptide; a light chain of an anti-TSPAN8 antibody comprising a light chain variable region consisting of an amino acid sequence from amino acid positions 1 to 107 of SEQ ID NO: 8; and a polypeptide in which an anti-CD3-scFv region comprising a heavy chain variable region consisting of an amino acid sequence from amino acid positions 1 to 125 of SEQ ID NO: 14 and a light chain variable region consisting of an amino acid sequence from amino acid positions 146 to 254 of SEQ ID NO: 14 is linked to a second Fc polypeptide; and (b) a bispecific antibody comprising a heavy chain of an anti-TSPAN8 antibody in which a heavy chain fragment of the anti-TSPAN8 antibody comprising a heavy chain variable region consisting of an amino acid sequence from amino acid positions 1 to 121 of SEQ ID NO: 10 is linked to a first Fc polypeptide; a light chain of an anti-TSPAN8 antibody comprising a light chain variable region consisting of an amino acid sequence from amino acid positions 1 to 107 of SEQ ID NO: 12; and a polypeptide in which an anti-CD3-scFv region comprising a heavy chain variable region consisting of an amino acid sequence from amino acid positions 1 to 125 of SEQ ID NO: 14 and a light chain variable region consisting of an amino acid sequence from amino acid positions 146 to 254 of SEQ ID NO: 14 is linked to a second Fc polypeptide.

In one aspect, the pharmaceutical composition of the present invention is a pharmaceutical composition containing an anti-TSPAN8/anti-CD3 bispecific antibody comprising a heavy chain of an anti-TSPAN8 antibody consisting of an amino acid sequence of SEQ ID NO: 6 in which a heavy chain fragment of the anti-TSPAN8 antibody is linked to a first Fc polypeptide, a light chain of an anti-TSPAN8 antibody consisting of an amino acid sequence of SEQ ID NO: 8, and a polypeptide consisting of an amino acid sequence of SEQ ID NO: 14 in which an anti-CD3-scFv region is linked to a second Fc polypeptide, and/or a post-translationally modified product of the antibody.

The amounts of the anti-TSPAN8/anti-CD3 bispecific antibody and the anti-TSPAN8 antibody of the present invention added in formulation are varied depending on the degree of symptom and the age of a patient, a dosage form of the formulation to be used, a binding titer of the antibody, or the like, and for example, can be about 0.001 mg/kg to 100 mg/kg.

<Pharmaceutical Use of Anti-TSPAN8/anti-CD3 Bispecific Antibody of Invention>

The anti-TSPAN8/anti-CD3 bispecific antibody of the present invention and a pharmaceutical composition containing the same can be used for treating cancer. Besides, the present invention embraces a method for treating cancer comprising a step of administering, to a subject, a therapeutically effective amount of the anti-TSPAN8/anti-CD3 bispecific antibody of the present invention. Furthermore, the present invention embraces the anti-TSPAN8/anti-CD3 bispecific antibody of the present invention for use in treating cancer. In addition, the present invention embraces use of the anti-TSPAN8/anti-CD3 bispecific antibody of the present invention, in production of a pharmaceutical composition for treating cancer. Cancer to be treated by the present invention is not especially limited, and examples include peritoneal dissemination of various cancer cells, gastric cancer, lung cancer, blood cancers such as acute lymphocytic leukemia (ALL), acute myelogenous leukemia (AML), Hodgkin's lymphoma, non-Hodgkin's lymphoma, B cell lymphoma, multiple myeloma and T cell lymphoma, solid cancers such as myelodysplastic syndromes, adenocarcinoma, squamous cell carcinoma, adenosquamous carcinoma, undifferentiated carcinoma, large cell carcinoma, non-small cell lung cancer, small cell lung cancer, mesothelioma, skin cancer, skin T cell lymphoma, breast cancer, prostate cancer, bladder cancer, vaginal cancer, cervix cancer, head and neck cancer, uterine cancer, cervical cancer, liver cancer, gallbladder cancer, bile duct cancer, kidney cancer, pancreatic cancer, colon cancer, colorectal cancer, rectal cancer, small intestine cancer, gastric cancer, esophageal cancer, testicular cancer, ovarian cancer and brain tumor, cancers of bone tissues, cartilage tissues, adipose tissues, muscle tissues, vascular tissues and blood-forming tissues, sarcomas such as chondrosarcoma, Ewing's sarcoma, malignant hemangioendothelioma, malignant schwannoma, osteosarcoma and soft tissue sarcoma, and blastomas such as glioblastoma, glioblastoma multiforme, hepatoblastoma, medulloblastoma, nephroblastoma, neuroblastoma, pancreatoblastoma, pleuropulmonary blastoma and retinoblastoma.

<Anti-TSPAN8 Antibody of Invention>

The present invention also provides a novel anti-TSPAN8 antibody against human TSPAN8 described below or a binding fragment thereof. The anti-TSPAN8 antibody or the antigen-binding fragment thereof provided by the present invention may be collectively referred to as "the anti-TSPAN8 antibody or the antigen-binding fragment thereof of the present invention".

The present invention provides an anti-TSPAN8 antibody that selectively binds to a human TSPAN8 expressing cancer cell or a binding fragment thereof.

Herein, the phrase "selectively binding to a human TSPAN8 expressing cancer cell" means that, when the binding activity of anti-TSPAN8 antibody is compared to a commercially available anti-TSPAN8 antibody (such as TAL69 and REA443) or an anti-TSPAN8 antibody exhibiting the same binding profile as in the commercially available anti-TSPAN8 antibody (such as 9F6 and 18C10), the binding intensity to TSPAN8 expressed in a human TSPAN8 expressing cancer cell is 3 times or more, preferably 5 times or more, further preferably 10 times or more, and the binding intensity to TSPAN8 expressed in a normal cell is ⅓ or less, preferably ⅕ or less, further preferably 1/10 or less, as compared with the commercially available antibodies or the like. The binding intensity to a cell of an antibody can be calculated, for example, using an MFI (mean fluorescence intensity) value obtained by flow cytometry described in Example 1, or a ΔMFI value obtained by subtracting each isotype MFI from the MFI of each antibody. Alternatively, the binding intensity to a cell of an antibody can be measured and calculated also by a method usually usable by those skilled in the art, such as ELISA using a cancer cell and a normal cell.

Here, a human TSPAN8 expressing cancer cell refers to a human TSPAN8 expressing cell isolated from a cancer patient, and not only a patient-derived peritoneal disseminated cancer cell described in Example 1-1 but also cancer cell lines available from a cell bank such as American Type Culture Collection (ATCC) can be used. As a cancer cell line, for example, not only a cell line established from the ascites fluid of a patient by a method described in Example 1-1 but also cell lines expressing TSPAN8 such as AGS, KATOIII, SNU5, SNU16, SNU520, ANU719, NCI-N87, HT-29, LoVo, GP2d, AsPC-1, 0E19, Li-7Hs746, NUGC-4, OCUM1, and MNK45 can be used. Besides, a normal cell refers to a cell derived from a normal tissue, and not only a patient-derived peritoneal mesothelial cell used in Example 1-5 but also commercially available primary cultured cells or cell lines such as a human peripheral blood mononuclear cell used in Example 1-3 and a cultured peritoneal mesothelial cell used in Example 1-3 can be used. In one aspect, a normal cell expresses TSPAN8. In one aspect, a normal cell expressing TSPAN8 is a patient-derived peritoneal mesothelial cell or a cultured peritoneal mesothelial cell used in Example 1-3. In one aspect, a normal cell is a cell not expressing TSPAN8. In one aspect, a normal cell not expressing TSPAN8 is a human peripheral blood mononuclear cell used in Example 1-3.

The present invention also provides an anti-TSPAN8 antibody that recognizes a part of a TSPAN8 protein as an epitope or an antigen-binding fragment thereof. In one aspect, the epitope is a structural unit consisting of an amino acid sequence contained in the LEL region of TSPAN8. In one aspect, the epitope is a structural unit consisting of a part of the TSPAN8 protein region represented by an amino acid sequence from 126 to 155 of SEQ ID NO: 2. In one aspect, the epitope is a structural unit consisting of one or more amino acid sequences contained in a part of the TSPAN8 protein region represented by an amino acid sequence from 126 to 155 of SEQ ID NO: 2. In one aspect, the epitope is a structural unit at least containing amino acid position 131 of SEQ ID NO: 2.

In one aspect, the anti-TSPAN8 antibody of the present invention or an antigen-binding fragment thereof binds to at least one amino acid present in the human TSPAN8 region from amino acid positions 126 to 155 of SEQ ID NO: 2. In one aspect, the anti-TSPAN8 antibody of the present invention or an antigen-binding fragment thereof binds to at least one amino acid present in the human TSPAN8 region from amino acid positions 126 to 155 of SEQ ID NO: 2 and selectively binds to a human TSPAN8 expressing cancer cell.

In one aspect, the anti-TSPAN8 antibody of the present invention or an antigen-binding fragment thereof at least binds to an amino acid at amino acid position 131 of SEQ ID NO: 2 present in the human TSPAN8 region from amino acid positions 126 to 155 of SEQ ID NO: 2. In one aspect, the anti-TSPAN8 antibody of the present invention or an antigen-binding fragment thereof at least binds to an amino acid at amino acid position 131 of SEQ ID NO: 2 present in the human TSPAN8 region from amino acid positions 126 to 155 of SEQ ID NO: 2 and selectively binds to a human TSPAN8 expressing cancer cell.

Whether or not the anti-TSPAN8 antibody or an antigen-binding fragment thereof binds to an amino acid present in the human TSPAN8 region from amino acid positions 126 to 155 of SEQ ID NO: 2 (e.g., an amino acid at amino acid position 131 of SEQ ID NO: 2) can be checked using the epitope identification method described in Examples 4-1 and 4-2 of this application.

The present invention further provides an anti-TSPAN8 antibody or an antigen-binding fragment thereof shown in (a) and (b) below:
  (a) an anti-TSPAN8 antibody or an antigen-binding fragment thereof, comprising a heavy chain variable region comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4, and a light chain variable region comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
  (b) an anti-TSPAN8 antibody or an antigen-binding fragment thereof, comprising a heavy chain variable region comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10, and a light chain variable region comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO. 12.

In one aspect, the anti-TSPAN8 antibody of the present invention or an antigen-binding fragment thereof is an anti-TSPAN8 antibody or an antigen-binding fragment thereof selected from the following (a) and (b):
  (a) An anti-TSPAN8 antibody or an antigen-binding fragment thereof comprising a heavy chain variable region consisting of an amino acid sequence from amino acid positions 1 to 121 of SEQ ID NO: 4, and a light chain variable region consisting of an amino acid sequence from amino acid positions 1 to 107 of SEQ ID NO: 8; and
  (b) an anti-TSPAN8 antibody or an antigen-binding fragment thereof comprising a heavy chain variable region consisting of an amino acid sequence from amino acid positions 1 to 121 of SEQ ID NO: 10, and a light chain variable region consisting of an amino acid sequence from amino acid positions 1 to 107 of SEQ ID NO: 12.

As a heavy chain constant region of the anti-TSPAN8 antibody of the present invention, any one of the constant regions Igγ, Igμ, Igα, Igδ and Igε can be selected. The Igγ can be selected from, for example, Igγ1, Igγ2, Igγ3 and Igγ4. In one aspect, the heavy chain constant region is Igγ1 constant region, and is, for example, human Igγ1 constant region. Besides, the heavy chain constant region of the anti-TSPAN8 antibody of the present invention may contain amino acid mutation such as LALA mutation for deteriorating ADCC or CDC. As a light chain constant region of the anti-TSPAN8 antibody of the present invention, either of the constant regions Igλ, and Igκ can be selected. In one aspect, the light chain constant region is Igκ constant region, and is, for example, human Igκ constant region.

In one aspect, an antigen-binding fragment of the anti-TSPAN8 antibody of the present invention is scFv, Fab, Fab', F(ab')$_2$ or a one-armed antibody.

In one aspect, the anti-TSPAN8 antibody of the present invention is an anti-TSPAN8 antibody selected from the following (a) and (b):
  (a) An anti-TSPAN8 antibody comprising a heavy chain consisting of an amino acid sequence of SEQ ID NO: 4 and a light chain consisting of an amino acid sequence of SEQ ID NO: 8; and
  (b) an anti-TSPAN8 antibody comprising a heavy chain consisting of an amino acid sequence of SEQ ID NO: 10 and a light chain consisting of an amino acid sequence of SEQ ID NO: 12.

The present invention provides an anti-TSPAN8 antibody or an antigen-binding fragment thereof (in particular, these are hereinafter referred to collectively as the "anti-TSPAN8 antibody of the present invention") described in the following (a) to (d):
  (a) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence from amino acid positions 1 to 121 of SEQ ID NO: 4, and a light chain variable region consisting of an amino acid sequence from amino acid positions 1 to 107 of SEQ ID NO: 8;
  (b) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence from amino acid positions 1 to 121 of SEQ ID NO: 10, and a light chain variable region consisting of an amino acid sequence from amino acid positions 1 to 107 of SEQ ID NO: 12;
  (c) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence of SEQ ID NO: 34, and a light chain variable region consisting of an amino acid sequence of SEQ ID NO: 36; and (d) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence of SEQ ID NO: 35, and a light chain variable region consisting of an amino acid sequence of SEQ ID NO: 37.

The competitive anti-TSPAN8 antibody of the present invention can be obtained, for example, by obtaining an antibody against human TSPAN8 using a human TSPAN8 expressing cell as an antigen using a known technique for producing antibodies and conducting a competition test on the antibody obtained for binding of the competing anti-TSPAN8 antibody to a human TSPAN8 expressing cell. For the competition test, methods known to those skilled in the art such as flow cytometry can be used. For example, the competition test using a human TSPAN8 expressing cancer cell described in Example 4-3 can be used. As the human TSPAN8 expressing cancer cell used in the competition test, various cells described above can be used.

In one aspect, the anti-TSPAN8 antibody of the present invention or an antigen-binding fragment thereof is an anti-TSPAN8 antibody or an antigen-binding fragment thereof selected from the following (a) and (b):

(a) an anti-TSPAN8 antibody or an antigen-binding fragment thereof competing in binding to the human TSPAN8 expressing cancer cell with an anti-TSPAN8 antibody comprising a heavy chain consisting of an amino acid sequence of SEQ ID NO: 4 and a light chain consisting of an amino acid sequence of SEQ ID NO: 8; and (b) an anti-TSPAN8 antibody or an antigen-binding fragment thereof competing in binding to the human TSPAN8 expressing cancer cell with an anti-TSPAN8 antibody comprising a heavy chain consisting of an amino acid sequence of SEQ ID NO: 10 and a light chain consisting of an amino acid sequence of SEQ ID NO: 12.

In one aspect, the anti-TSPAN8 antibody of the present invention or an antigen-binding fragment thereof is an anti-TSPAN8 antibody or an antigen-binding fragment thereof selected from the following (c) and (d):

(c) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence of SEQ ID NO: 34, and a light chain variable region consisting of an amino acid sequence of SEQ ID NO: 36; and (d) an anti-TSPAN8 antibody or an antigen-binding fragment thereof competing in binding to the human TSPAN8 expressing cancer cell with an anti-TSPAN8 antibody comprising a heavy chain variable region consisting of an amino acid sequence of SEQ ID NO: 35, and a light chain variable region consisting of an amino acid sequence of SEQ ID NO: 37.

<Alternative Bispecific Antibody of Invention>

The present invention provides a bispecific antibody comprising the anti-TSPAN8 antibody of the present invention or an antigen-binding fragment thereof linked to an antibody to a surface antigen of a T cell or a natural killer (NK) cell, or an antigen-binding fragment thereof. The form of the bispecific antibody is not especially limited, and it can be in any form usually usable by those skilled in the art, such as antibodies in various forms described in NON PATENT LITERATUREs 3 or 4.

The present invention also provides a bispecific antibody as follows:

A bispecific antibody that binds to TSPAN8 and a surface antigen of a T cell or an NK cell, comprising:

(a) a Fab region of an anti-TSPAN8 antibody consisting of a heavy chain fragment comprising a heavy chain variable region of the anti-TSPAN8 antibody of the present invention, and a light chain comprising a light chain variable region of the anti-TSPAN8 antibody of the present invention;

(b) a scFv region of an antibody to a surface antigen of a T cell or an NK cell comprising a heavy chain variable region and a light chain variable region of the antibody to a surface antigen of a T cell or an NK cell; and (c) a Fc region consisting of a first Fc polypeptide linked to the heavy chain fragment of the Fab region (a) and a second Fc polypeptide linked to the scFv region (b).

The alternative bispecific antibodies of the present invention can be easily produced by those skilled in the art by employing a method described in NON PATENT LITERATURE 4 or a general method obtained referring to the description of <Anti-TSPAN8/anti-CD3 Bispecific Antibody of Invention>. As the antibody to a surface antigen of a T cell or an NK cell, many antibodies are known so far (Current Opinion in Biotechnology, 2020, Vol. 65, p. 9-16), and sequence information on these antibodies can be used. Other aspects of the alternative bispecific antibodies of the present invention are the same as those described in <Anti-TSPAN8/anti-CD3 Bispecific Antibody of Invention>except that an anti-CD3 antibody scFv region is used. The alternative bispecific antibodies of the present invention can be also used for treating cancer.

In one aspect, the antibody to a surface antigen of a T cell or an NK cell, or an antigen-binding fragment thereof of the alternative bispecific antibodies of the present invention is an antibody to a surface antigen of a T cell or an NK cell, or an antigen-binding fragment thereof. In one aspect, the antibody to a surface antigen of a T cell or an NK cell, or an antigen-binding fragment thereof is an anti-CD3 antibody, an anti-CD137 antibody, an anti-PD-1 (programmed cell death-1) antibody, an anti-PD-L1 (programmed cell death 1-ligand 1) antibody, an anti-TIGIT (T cell immunoreceptor with Ig and ITIM domains) antibody, an anti-CD16 antibody, an anti-NKG2D (natural killer group 2, member D) antibody, or an antigen-binding fragment of these. In one aspect, the antibody to a T cell or an antigen-binding fragment thereof is an anti-CD3 antibody or an antigen-binding fragment thereof. In one aspect, an antigen-binding fragment of the anti-CD3 antibody is scFv of an anti-CD3 antibody.

<Fusion and Complex of Invention, and Cell on Surface of Which Anti-TSPAN8 of Invention or Antigen-Binding Fragment Thereof is Expressed>

The present invention also provides an anti-TSPAN8 antibody of the present invention or an antigen-binding fragment thereof linked to another protein (including an antibody) excluding TSPAN8, or to a polypeptide (also referred to as the "fusion of the present invention"). A protein or a polypeptide used in the fusion of the present invention is not especially limited, and various antibodies, cytokine, chemokine, human serum albumin, various tag peptides, artificial helix motif peptide, maltose binding protein, glutathione S-transferase, and other peptides or proteins capable of accelerating multimerization can be used. In one aspect of the fusion of the present invention, a protein or polypeptide is linked to the anti-TSPAN8 antibody of the present invention or an antigen-binding fragment thereof. In one aspect, a protein or polypeptide used in the fusion of the present invention may be an antibody to a surface antigen of an immune cell such as a granulocyte or a natural killer T (NKT) cell, a blood cell such as a dendritic cell or a macrophage, or an antigen-binding fragment thereof, or a polypeptide activating an immune cell such as various interleukins (such as IL-2, IL-7, IL-12 and IL-15). In this case, the protein or polypeptide used in the fusion of the present invention may be directly linked to the anti-TSPAN8 antibody of the present invention or an antigen-binding fragment thereof, or may be linked through an arbitrary linker (such as a peptide linker).

The present invention also provides the anti-TSPAN8 antibody of the present invention or an antigen-binding fragment thereof (referred to also as the "complex of the present invention") linked to a sugar, a lipid, a metal (including a radioisotope), an organic compound (including a toxin, a near-infrared fluorescent dye and a chelating agent) (referred to also as "modifier"). Herein, the term "modifier" refers to a non-peptide substance that binds to the antibody or the antigen-binding fragment thereof directly or through a linker or the like. A modifier used for the complex of the present invention is not especially limited, and examples include polyethylene glycol, a sugar chain, a phospholipid, a radioisotope (such as zirconium-89 ($^{89}$Zr), yttrium 90 ($^{90}$Y), indium-111 ($^{111}$In), astatine-211 ($^{211}$At), actinium-225 (225Ac)), an organic compound, a toxin, a near-infrared fluorescent dye (such as IRDye(R)) and a chelating agent. The modifier used in the complex may be bonded to the anti-TSPAN8 antibody of the present invention or the antigen-binding fragment thereof directly or through an arbitrary linker. In one aspect, the complex of the present invention is an antibody drug conjugate (ADC) of the anti-TSPAN8 antibody or an antigen-binding fragment thereof. A drug and a linker usable in an ADC can be selected from drugs and linkers usually used by those skilled in the art. In one aspect, the complex of the present invention is a radioisotope-labeled antibody in which a radioisotope is bonded to the anti-TSPAN8 antibody or an antigen-binding fragment thereof.

The present invention also provides a cell (such as a chimeric antigen receptor-T cell; CAR-T cell) on a surface of which an anti-TSPAN8 antibody of the present invention or an antigen-binding fragment thereof is expressed. Such a cell can be produced by those skilled in the art by using a polynucleotide encoding the anti-TSPAN8 antibody of the present invention or an antigen-binding fragment thereof. As the cell in which the anti-TSPAN8 antibody of the present invention or an antigen-binding fragment thereof is expressed, various immune cells (such as a T cell, an NK cell and an NKT cell) can be used.

The anti-TSPAN8 antibody of the present invention or an antigen-binding fragment thereof, the fusion of the present invention, the complex of the present invention and the cell on a surface of which an anti-TSPAN8 antibody of the present invention or an antigen-binding fragment thereof is expressed bind to human TSPAN8 (GENBANK Accession No. NM 004616.2). The binding to human TSPAN8 can be checked by a known binding activity measurement method. Examples of a method for measuring binding activity include ELIA and flow cytometry. When ELISA is employed, for example, a method described in Example 8 can be employed, and when flow cytometry is employed, for example, a method described in Example 1 can be employed.

In one aspect, the part of the antibody or the antigen-binding fragment in the anti-TSPAN8 antibody of the present invention or the antigen-binding fragment thereof, the fusion and the complex of the present invention, and a cell on a surface of which the anti-TSPAN8 of the present invention or the antigen-binding fragment thereof is expressed may be post-translationally modified. In one aspect, the post-translational modification is pyroglutamylation at the N-terminal of the heavy chain variable region and/or lysine deletion at the heavy chain C-terminal.

The anti-TSPAN8 antibody of the present invention or the antigen-binding fragment thereof, the fusion of the present invention, the complex of the present invention, and the cell on a surface of which the anti-TSPAN8 of the present invention or the antigen-binding fragment thereof is expressed can be produced by those skilled in the art by employing a method known in this technical field based on sequence information on VH and VL of the anti-TSPAN8 antibody of the present invention or the antigen-binding fragment thereof disclosed herein, and information on other peptides or proteins (such as an antibody) used in the fusion of the present invention and modifiers used in the complex of the present invention. The anti-TSPAN8 antibody of the present invention or an antigen-binding fragment thereof can be produced, for example, by a method not especially limited but by a method described in <Method for Producing Bispecific Antibody of Invention>.

<Polynucleotide, Expression Vector, Host Cell and Production Method for Anti-TSPAN8 Antibody of Invention>

The present invention also provides polynucleotides described in the following (1) to (4):

(1) A polynucleotide comprising a nucleotide sequence encoding a heavy chain variable region of the anti-TSPAN8 antibody of the present invention or an antigen-binding fragment thereof;

(2) a polynucleotide comprising a nucleotide sequence encoding a light chain variable region of the anti-TSPAN8 antibody of the present invention or an antigen-binding fragment thereof;

(3) a polynucleotide comprising a nucleotide sequence encoding a heavy chain of the anti-TSPAN8 antibody of the present invention; and (4) a polynucleotide comprising a nucleotide sequence encoding a light chain of the anti-TSPAN8 antibody of the present invention.

In one aspect of the polynucleotide (1) described above, the polynucleotide comprising a nucleotide sequence encoding a heavy chain variable region of the anti-TSPAN8 antibody of the present invention or an antigen-binding fragment thereof is a polynucleotide selected from the following (a) and (b):

(a) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO: 4; and (b) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO: 10.

In one aspect of the polynucleotide (1) described above, the polynucleotide comprising a nucleotide sequence encoding a heavy chain variable region of the anti-TSPAN8 antibody of the present invention or an antigen-binding fragment thereof is a polynucleotide selected from the following (a) and (b):
(a) a polynucleotide comprising a nucleotide sequence encoding a heavy chain variable region of an anti-TSPAN8 antibody consisting of an amino acid sequence from amino acid positions 1 to 121 of SEQ ID NO: 4; and
(b) a polynucleotide comprising a nucleotide sequence encoding a heavy chain variable region of an anti-TSPAN8 antibody consisting of an amino acid sequence from amino acid positions 1 to 121 of SEQ ID NO: 10.

In one aspect of the polynucleotide (2) described above, the polynucleotide comprising a nucleotide sequence encoding a light chain variable region of the anti-TSPAN8 antibody of the present invention or an antigen-binding fragment thereof is a polynucleotide selected from the following (a) and (b):
(a) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO: 8; and
(b) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12.

In one aspect of the polynucleotide (2) described above, the polynucleotide comprising a nucleotide sequence encoding a light chain variable region of the anti-TSPAN8 antibody of the present invention or an antigen-binding fragment thereof is a polynucleotide selected from the following (a) and (b):
(a) a polynucleotide comprising a nucleotide sequence encoding a light chain variable region of an anti-TSPAN8 antibody consisting of an amino acid sequence from amino acid positions 1 to 107 of SEQ ID NO: 8; and
(b) a polynucleotide comprising a nucleotide sequence encoding a light chain variable region of an anti-TSPAN8 antibody consisting of an amino acid sequence from amino acid positions 1 to 107 of SEQ ID NO: 12.

In one aspect of the polynucleotide (3) described above, the polynucleotide comprising a nucleotide sequence encoding a heavy chain of the anti-TSPAN8 antibody of the present invention is a polynucleotide selected from the following (a) and (b):
(a) a polynucleotide comprising a nucleotide sequence encoding a heavy chain of an anti-TSPAN8 antibody consisting of an amino acid sequence of SEQ ID NO: 4; and
(b) a polynucleotide comprising a nucleotide sequence encoding a heavy chain of an anti-TSPAN8 antibody consisting of an amino acid sequence of SEQ ID NO: 10.

In one aspect of the polynucleotide (4) described above, the polynucleotide comprising a nucleotide sequence encoding a light chain of the anti-TSPAN8 antibody of the present invention is a polynucleotide selected from the following (a) and (b):
(a) a polynucleotide comprising a nucleotide sequence encoding a light chain of an anti-TSPAN8 antibody consisting of an amino acid sequence of SEQ ID NO: 8; and
(b) a polynucleotide comprising a nucleotide sequence encoding a light chain of an anti-TSPAN8 antibody consisting of an amino acid sequence of SEQ ID NO: 12.

The polynucleotides described herein can be produced by those skilled in the art by employing a method known in this technical field based on the nucleotide sequences thereof.

The present invention also provides an expression vector comprising one of or a plurality of polynucleotides described in the following (1) to (4) (also referred to as the "expression vector for the anti-TSPAN8 antibody of the present invention"). Each expression vector may comprise each of or a plurality of the polynucleotides.

(1) A polynucleotide comprising a nucleotide sequence encoding a heavy chain variable region of the anti-TSPAN8 antibody of the present invention or an antigen-binding fragment thereof;

(2) a polynucleotide comprising a nucleotide sequence encoding a light chain variable region of the anti-TSPAN8 antibody of the present invention or an antigen-binding fragment thereof;

(3) a polynucleotide comprising a nucleotide sequence encoding a heavy chain of the anti-TSPAN8 antibody of the present invention; and (4) a polynucleotide comprising a nucleotide sequence encoding a light chain of the anti-TSPAN8 antibody of the present invention.

In one aspect of the expression vector for the anti-TSPAN8 antibody of the present invention comprising the polynucleotide (1) described above, the expression vector comprises a polynucleotide selected from the following (a) and (b):
(a) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4; and
(b) a polynucleotide a heavy chain variable region of an anti-TSPAN8 antibody comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10.

In one aspect of the expression vector for the anti-TSPAN8 antibody of the present invention comprising the polynucleotide (1) described above, the expression vector comprises a polynucleotide selected from the following (a) and (b):
- (a) a polynucleotide comprising a nucleotide sequence encoding a heavy chain variable region of an anti-TSPAN8 antibody consisting of an amino acid sequence from amino acid positions 1 to 121 of SEQ ID NO: 4; and
- (b) a polynucleotide comprising a nucleotide sequence encoding a heavy chain variable region of an anti-TSPAN8 antibody consisting of an amino acid sequence from amino acid positions 1 to 121 of SEQ ID NO: 10.

In one aspect of the expression vector for the anti-TSPAN8 antibody of the present invention comprising the polynucleotide (2) described above, the expression vector comprises a polynucleotide selected from the following (a) and (b):
- (a) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
- (b) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12.

In one aspect of the expression vector for the anti-TSPAN8 antibody of the present invention comprising the polynucleotide (2) described above, the expression vector comprises a polynucleotide selected from the following (a) and (b):
- (a) a polynucleotide comprising a nucleotide sequence encoding a light chain variable region of an anti-TSPAN8 antibody consisting of an amino acid sequence from amino acid positions 1 to 107 of SEQ ID NO: 8; and
- (b) a polynucleotide comprising a nucleotide sequence encoding a light chain variable region of an anti-TSPAN8 antibody consisting of an amino acid sequence from amino acid positions 1 to 107 of SEQ ID NO: 12.

In one aspect of the expression vector for the anti-TSPAN8 antibody of the present invention comprising the polynucleotide (3) described above, the expression vector comprises a polynucleotide selected from the following (a) and (b):
- (a) a polynucleotide comprising a nucleotide sequence encoding a heavy chain of an anti-TSPAN8 antibody consisting of an amino acid sequence of SEQ ID NO: 4; and
- (b) a polynucleotide comprising a nucleotide sequence encoding a heavy chain of an anti-TSPAN8 antibody consisting of an amino acid sequence of SEQ ID NO: 10.

In one aspect of the expression vector for the anti-TSPAN8 antibody of the present invention comprising the polynucleotide (4) described above, the expression vector comprises a polynucleotide selected from the following (a) and (b):
- (a) a polynucleotide comprising a nucleotide sequence encoding a light chain of an anti-TSPAN8 antibody consisting of an amino acid sequence of SEQ ID NO: 8; and
- (b) a polynucleotide comprising a nucleotide sequence encoding a light chain of an anti-TSPAN8 antibody consisting of an amino acid sequence of SEQ ID NO: 12.

In one aspect, the expression vector for the anti-TSPAN8 antibody of the present invention is an expression vector comprising polynucleotides selected from the following (a) and (b):
- (a) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4, and a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
- (b) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10, and a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO: 12.

In one aspect, the expression vector for the anti-TSPAN8 antibody of the present invention is an expression vector comprising polynucleotides selected from the following (a) and (b):
- (a) a polynucleotide comprising a nucleotide sequence encoding a heavy chain variable region of an anti-TSPAN8 antibody consisting of an amino acid sequence from amino acid positions 1 to 121 of SEQ ID NO: 4, and a polynucleotide comprising a nucleotide sequence encoding a light chain variable region of an anti-TSPAN8 antibody consisting of an amino acid sequence from amino acid positions 1 to 107 of SEQ ID NO: 8; and
- (b) a polynucleotide comprising a nucleotide sequence encoding a heavy chain variable region of an anti-TSPAN8 antibody consisting of an amino acid sequence from amino acid positions 1 to 121 of SEQ ID NO: 10, and a polynucleotide comprising a nucleotide sequence encoding a light chain variable region of an anti-TSPAN8 antibody consisting of an amino acid sequence from amino acid positions 1 to 107 of SEQ ID NO: 12.

In one aspect, the expression vector for the anti-TSPAN8 antibody of the present invention is an expression vector comprising polynucleotides selected from the following (a) and (b):
  (a) a polynucleotide comprising a nucleotide sequence encoding a heavy chain of an anti-TSPAN8 antibody consisting of an amino acid sequence of SEQ ID NO: 4, and a polynucleotide comprising a nucleotide sequence encoding a light chain of an anti-TSPAN8 antibody consisting of an amino acid sequence of SEQ ID NO: 8; and
  (b) a polynucleotide comprising a nucleotide sequence encoding a heavy chain of an anti-TSPAN8 antibody consisting of an amino acid sequence of SEQ ID NO: 10, and a polynucleotide comprising a nucleotide sequence encoding a light chain of an anti-TSPAN8 antibody consisting of an amino acid sequence of SEQ ID NO: 12.

The expression vector described herein can be produced by those skilled in the art in accordance with the method described above in <Expression Vector for Bispecific Antibody of Invention>.

The present invention also provides a host cell transformed with an expression vector comprising polynucleotides described in the following (1) to (4) (referred to also as the "host cell for the anti-TSPAN8 antibody of the present invention"). The host cell for the anti-TSPAN8 antibody of the present invention may comprise one of or a plurality of the polynucleotides described in the following (1) to (4) through transformation with the expression vector for the anti-TSPAN8 antibody of the present invention.
  (1) A polynucleotide comprising a nucleotide sequence encoding a heavy chain variable region of the anti-TSPAN8 antibody of the present invention or an antigen-binding fragment thereof;
  (2) a polynucleotide comprising a nucleotide sequence encoding a light chain variable region of the anti-TSPAN8 antibody of the present invention or an antigen-binding fragment thereof;
  (3) a polynucleotide comprising a nucleotide sequence encoding a heavy chain of the anti-TSPAN8 antibody of the present invention; and
  (4) a polynucleotide comprising a nucleotide sequence encoding a light chain of the anti-TSPAN8 antibody of the present invention.

In one aspect of the host cell for the anti-TSPAN8 antibody of the present invention comprising the polynucleotide (1) described above, the host cell comprises a polynucleotide selected from the following (a) and (b):
  (a) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4; and
  (b) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10.

In one aspect of the host cell for the anti-TSPAN8 antibody of the present invention comprising the polynucleotide (1) described above, the host cell comprises a polynucleotide selected from the following (a) and (b):
  (a) a polynucleotide comprising a nucleotide sequence encoding a heavy chain variable region of an anti-TSPAN8 antibody consisting of an amino acid sequence from amino acid positions 1 to 121 of SEQ ID NO: 4; and
  (b) a polynucleotide comprising a nucleotide sequence encoding a heavy chain variable region of an anti-TSPAN8 antibody consisting of an amino acid sequence from amino acid positions 1 to 121 of SEQ ID NO: 10.

In one aspect of the host cell for the anti-TSPAN8 antibody of the present invention comprising the polynucleotide (2) described above, the host cell comprises a polynucleotide selected from the following (a) and (b):
  (a) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
  (b) a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO. 12.

In one aspect of the host cell for the anti-TSPAN8 antibody of the present invention comprising the polynucleotide (2) described above, the host cell comprises a polynucleotide selected from the following (a) and (b):
  (a) a polynucleotide comprising a nucleotide sequence encoding a light chain variable region of an anti-TSPAN8 antibody consisting of an amino acid sequence from amino acid positions 1 to 107 of SEQ ID NO: 8; and
  (b) a polynucleotide comprising a nucleotide sequence encoding a light chain variable region of an anti-TSPAN8 antibody consisting of an amino acid sequence from amino acid positions 1 to 107 of SEQ ID NO: 12.

In one aspect of the host cell for the anti-TSPAN8 antibody of the present invention comprising the polynucleotide (3) described above, the host cell comprises a polynucleotide selected from the following (a) and (b):
  (a) a polynucleotide comprising a nucleotide sequence encoding a heavy chain of an anti-TSPAN8 antibody consisting of an amino acid sequence of SEQ ID NO: 4; and (b) a polynucleotide comprising a nucleotide sequence encoding a heavy chain of an anti-TSPAN8 antibody consisting of an amino acid sequence of SEQ ID NO: 10.

In one aspect of the host cell for the anti-TSPAN8 antibody of the present invention comprising the polynucleotide (4) described above, the host cell comprises a polynucleotide selected from the following (a) and (b):
(a) a polynucleotide comprising a nucleotide sequence encoding a light chain of an anti-TSPAN8 antibody consisting of an amino acid sequence of SEQ ID NO: 8; and
(b) a polynucleotide comprising a nucleotide sequence encoding a light chain of an anti-TSPAN8 antibody consisting of an amino acid sequence of SEQ ID NO: 12.

In one aspect, the host cell for the anti-TSPAN8 antibody of the present invention comprises polynucleotides selected from the following (a) and (b):
(a) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 4, a CDR2 consisting of an amino acid sequence from amino acid positions 50 to 66 of SEQ ID NO: 4, and a CDR3 consisting of an amino acid sequence from amino acid positions 99 to 110 of SEQ ID NO. 4, and a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 8, a CDR2 consisting of an amino acid sequence from amino acid positions 50 to 56 of SEQ ID NO: 8, and a CDR3 consisting of an amino acid sequence from amino acid positions 89 to 96 of SEQ ID NO. 8; and
(b) a polynucleotide comprising a nucleotide sequence encoding a heavy chain variable region of an anti-TSPAN8 antibody comprising a CDR1 consisting of an amino acid sequence from amino acid positions 31 to 35 of SEQ ID NO: 10, a CDR2 consisting of an amino acid sequence from amino acid positions 50 to 66 of SEQ ID NO: 10, and a CDR3 consisting of an amino acid sequence from amino acid positions 99 to 110 of SEQ ID NO. 10, and a polynucleotide comprising a nucleotide sequence encoding a light chain variable region of an anti-TSPAN8 antibody comprising a CDR1 consisting of an amino acid sequence from amino acid positions 24 to 34 of SEQ ID NO: 12, a CDR2 consisting of an amino acid sequence from amino acid positions 50 to 56 of SEQ ID NO: 12, and a CDR3 consisting of an amino acid sequence from amino acid positions 89 to 96 of SEQ ID NO. 12.

In one aspect, the host cell for the anti-TSPAN8 antibody of the present invention is a host cell comprising polynucleotides selected from the following (a) and (b):
(a) a polynucleotide comprising a nucleotide sequence encoding a heavy chain variable region of an anti-TSPAN8 antibody consisting of an amino acid sequence from amino acid positions 1 to 121 of SEQ ID NO: 4, and a polynucleotide comprising a nucleotide sequence encoding a light chain variable region of an anti-TSPAN8 antibody consisting of an amino acid sequence from amino acid positions 1 to 107 of SEQ ID NO: 8; and
(b) a polynucleotide comprising a nucleotide sequence encoding a heavy chain variable region of an anti-TSPAN8 antibody consisting of an amino acid sequence from amino acid positions 1 to 121 of SEQ ID NO: 10, and a polynucleotide comprising a nucleotide sequence encoding a light chain variable region of an anti-TSPAN8 antibody consisting of an amino acid sequence from amino acid positions 1 to 107 of SEQ ID NO: 12.

In one aspect, the host cell for the anti-TSPAN8 antibody of the present invention is a host cell comprising polynucleotides selected from the following (a) and (b):
(a) a polynucleotide comprising a nucleotide sequence encoding a heavy chain of an anti-TSPAN8 antibody consisting of an amino acid sequence of SEQ ID NO: 4, and a polynucleotide comprising a nucleotide sequence encoding a light chain of an anti-TSPAN8 antibody consisting of an amino acid sequence of SEQ ID NO: 8; and
(b) a polynucleotide comprising a nucleotide sequence encoding a heavy chain of an anti-TSPAN8 antibody consisting of an amino acid sequence of SEQ ID NO: 10, and a polynucleotide comprising a nucleotide sequence encoding a light chain of an anti-TSPAN8 antibody consisting of an amino acid sequence of SEQ ID NO: 12.

The host cell described herein can be produced by those skilled in the art in accordance with the method described above in <Transformed Host Cell of Invention>.

The present invention also provides a method for producing an anti-TSPAN8 antibody or an antigen-binding fragment thereof comprising a step of culturing the host cell for the anti-TSPAN8 antibody of the present invention. This method can be performed by those skilled in the art in accordance with <Method for Producing Bispecific Antibody of Invention> described above.

<Pharmaceutical Use of Anti-TSPAN8 Antibody or the like of Invention>

The present invention also provides a pharmaceutical composition containing the anti-TSPAN8 antibody of the present invention or the antigen-binding fragment thereof, the fusion of the present invention, the complex of the present invention, and the cell on a surface of which the anti-TSPAN8 of the present invention or an antigen-binding fragment thereof is expressed (hereinafter, all of which will be together referred to as the "anti-TSPAN8 antibody and the like of the present invention"), and a pharmaceutically acceptable excipient. The pharmaceutical composition can be used for treating cancer. The present invention also provides a method for treating cancer comprising a step of administering, to a subject, a therapeutically effective amount of the anti-TSPAN8 antibody and the like of the present invention, and use of the anti-TSPAN8 antibody and the like of the present invention in production of a pharmaceutical composition for treating cancer such as the anti-TSPAN8 antibody and the like of the present invention to be used for treating cancer. The pharmaceutical use of the anti-TSPAN8 antibody and the like of the present invention can be performed by those skilled in the art in accordance with the description given in <Pharmaceutical Composition or the like of Bispecific Antibody of Invention> above. Examples of the cancer to be treated in the pharmaceutical use of the anti-TSPAN8 antibody and the like of the present invention include cancers described in <Pharmaceutical Composition or the like of Bispecific Antibody of Invention> above.

<Anti-CD3 Antibody of Invention>

The present invention also provides an anti-CD3 antibody or an antigen-binding fragment thereof as follows:

An anti-CD3 antibody or an antigen-binding fragment thereof comprising a heavy chain variable region comprising a CDR1 consisting of an amino acid sequence from amino acid positions 31 to 35 of SEQ ID NO: 14, a CDR2 consisting of an amino acid sequence from amino acid positions 50 to 68 of SEQ ID NO: 14, and a CDR3 consisting of an amino acid sequence from amino acid positions 101 to 114 of SEQ ID NO: 14, and a light chain variable region comprising a CDR1 consisting of an amino acid sequence from amino acid positions 168 to 181 of SEQ ID NO: 14, a CDR2 consisting of an amino acid sequence from amino acid positions 197 to 203 of SEQ ID NO: 14, and a CDR3 consisting of an amino acid sequence from amino acid positions 236 to 244 of SEQ ID NO: 14.

In one aspect, the anti-CD3 antibody of the present invention or an antigen-binding fragment thereof is an anti-CD3 antibody or an antigen-binding fragment thereof comprising a heavy chain variable region consisting of an amino acid sequence from amino acid positions 1 to 125 of SEQ ID NO: 14, and a light chain variable region consisting of an amino acid sequence from amino acid positions 146 to 254 of SEQ ID NO: 14.

In one aspect, an antigen-binding fragment of the anti-CD3 antibody of the present invention is scFv. In one aspect, an antigen-binding fragment of the anti-CD3 antibody of the present invention is anti-CD3 antibody scFv comprising a heavy chain variable region consisting of an amino acid sequence from amino acid positions 1 to 125 of SEQ ID NO: 14 and a light chain variable region consisting of an amino acid sequence from amino acid positions 146 to 254 of SEQ ID NO: 14. In one aspect, an antigen-binding fragment of the anti-CD3 antibody of the present invention is anti-CD3 antibody scFv consisting of an amino acid sequence from amino acid positions 1 to 254 of SEQ ID NO: 14.

The anti-CD3 antibody of the present invention or the antigen-binding fragment thereof can be produced by those skilled in the art referring to the description herein given in and the like. The anti-CD3 antibody of the present invention or an antigen-binding fragment thereof can be checked by employing a known binding activity measurement method. The anti-CD3 antibody of the present invention or an antigen-binding fragment thereof can be used in a bispecific antibody with an antibody to a tumor antigen for use in treating cancer.

Specific examples to be referred for gaining further understanding of the present invention will now be provided here, and it is noted these examples are merely illustrative but do not limit the present invention.

EXAMPLES

Example 1: Acquisition of Antibody that Selectively Binds to Antigen Expressed in Peritoneal Disseminated Cancer Cell Example 1-1: Acquisition of Patient-derived Peritoneal Disseminated Cancer Cell Peritoneal disseminated cancer cells were acquired from patients as follows. Peritoneal disseminated cancer cells were acquired from a patient in accordance with a method described in the literature by Fumiko Chiwaki and Hiroki Sasaki, "Establishment of Cell Lines of Peritoneal Disseminated Cancer (such as gastric, pancreatic or ovarian cancer) (Fukumaku Tenni Gan (I, Sui, Ranso Gan nado) Saiboukabu no Juritsu) (edited by Hiroki Sasaki, "Practical Guide for Cancer Research using Patient-derived Experimental Model", Yodosha Co., Ltd., 2019, p. 28-37). An ascites fluid collected from a patient was dispensed into PROTEOSAVE (R) SS 50 mL centrifuge tube (Sumitomo Bakelite Co., Ltd., MS-52550, hereinafter referred to as the "50 mL centrifuge tube") to be centrifuged 430×g for 3 minutes at room temperature. Supernatant was removed, a hemolytic buffer was added to the precipitate, and the resultant was hemolyzed for 10 to 20 minutes at room temperature. The hemolytic buffer was prepared by filtering 17 mM Tris-HCL (pH 7.65) containing 0.75% ammonium chloride through a filter having a pore size of 0.22 μm. After centrifugation, supernatant was removed, and 50 mL of Dulbecco's PBS(−) (Nissui Pharmaceutical Co., Ltd., 05913, hereinafter referred to as "PBS(−)") was added thereto to wash cells. Thereafter, the resultant was centrifuged 430×g for 3 minutes at room temperature to collect the cells. All the cells contained in the ascites fluid thus collected were suspended again in RPMI-1640 (L-glutamine-containing) medium (FUJIFILM Wako Pure Chemical Corporation, 189-02025) containing 10% FBS (Thermo Fisher Scientific, 10270-106) and ×1 Antibiotic-Antimycotic (Thermo Fisher Scientific, 15240062) (hereinafter, the medium with FBS or the like added will be referred to as the "RPMI-1640 medium"). Cells were seeded in a 100-mm collagen-coated dish (hereinafter referred to as "dish") (IWAKI & CO., LTD., 4020-010) at $5 \times 10^6$ to $1 \times 10^7$/10 mL and cultured in a 5% $CO_2$ incubator at 37° C.

Ascites cells include adhesive cells and floating cells. Adhesive cells include not only cancer cells but also cells other than cancer cells (fibroblasts, peritoneal mesothelial cells, and the like). Using the characteristic that cells other than cancer cells exfoliate in a shorter time than cancer cells, these cells were separated from all cells in ascites fluid. Specifically, a dish in which all the cells contained in the ascites fluid had been cultured was washed with PBS(−), and the resultant was treated with 2 mL of 0.05% trypsin-EDTA (Thermo Fisher Scientific, 15400054) for several minutes to peel the cells apart from the cancer cells. The cells apart from the cancer cells included in the thus peeled cells were continuously cultured in a new dish to be used in Example 1-5.

After removing the cells apart from the cancer cells, an operation in which a half of all cells were passaged to a new dish after the cancer cells had been grown to about 80% confluent in the dish area was repeated, and cells obtained after five or more passages were defined as adherent cancer cells. With respect to floating cells, 5 mL of a culture supernatant from the culture dish and 5 mL of the RPMI-1640 medium were seeded and passaged in a new 100 mm dish, and cells obtained after five or more passages were defined as floating cancer cells. When peritoneal disseminated cancer cells derived from one patient grew with both the adherent cancer cells and the floating cancer cells included therein, these cells were defined as mixed cancer cells.

Herein, the adherent cancer cells, the floating cancer cells, or the mixed cancer cells isolated from the ascites fluid collected from a patient as described above are collectively designated as the "peritoneal disseminated cancer cells". The thus obtained twelve cells (NSC-7C, NSC-9C, NCS-10C, NSC-14C, NSC-15CF, NSC-16C, NSC-20C, NSC-22C, NSC-24C, NSC-32C, NSC-34C and NSC-35C-1

(hereinafter, also referred to as the "twelve peritoneal disseminated cancer cells")) were used in the subsequent examinations.

Example 1-2: Production of Anti-Gastric Cancer Antigen Antibody Producing Hybridomas A mouse by "VelocImmune" (VelocImmune (R) antibody technology; Regeneron (U.S. Pat. No. 6,596,541), human monoclonal antibody development technology, was used to obtain an anti-gastric cancer antigen antibody that binds to a peritoneal disseminated cancer cell. Among the peritoneal disseminated cancer cells obtained in Example 1-1, every three cells out of the cells NSC-10C, NSC-35C-1, NSC-24C, NSC-7C, NSC-14C and NSC-34C were mixed and suspended in TiterMax (R) Gold ADJUVANT (MERCK, T2684) or PBS(-) to prepare a peritoneal disseminated cancer cell suspension. The suspension was used to immunize a VelocImmune mouse, and hybridomas were produced by a conventional method. A single colony of the hybridomas was isolated using an automatic picking device, and thus, monoclonal hybridoma cells (hereinafter referred to as the "clones") were obtained. The clones thus isolated were cultured in an 8% $CO_2$ incubator at 37° C., and supernatant was collected in a 96 well plate after culturing for 4 days and used in the following experiments.

Example 1-3: Selection of Anti-Gastric Cancer Antigen Antibody that Selectively Binds to Peritoneal Disseminated Cancer Cell 1. Check of Binding of Anti-Gastric Cancer Antigen Antibody to Peritoneal Disseminated Cancer Cell and EpCAM Expressing Cell Cell supernatant of the clones obtained in Example 1-2 contains antibodies (hereinafter referred to as the "antibodies contained in the clone supernatant").

First, bindings of the antibodies contained in the clone supernatant to each of the twelve Peritoneal disseminated cancer cells obtained in Example 1-1 were measured by flow cytometry, and a clone producing an antibody that strongly binds to a peritoneal disseminated cancer cell was selected. For the flow cytometry, BV421 Goat Anti-Mouse Ig (Becton, Dickinson and Company, 563846) was used. Then, in order to exclude clones providing antibodies that bind to EpCAM, that is, a cancer antigen, bindings of the antibodies contained in the clone supernatant to a human EpCAM-Myc-DDK expressed CHO-K1 cell were measured. The human EpCAM-Myc-DDK expressed CHO-K1 cell was produced by transfecting EPCAM (Myc-DDK-tagged)-Human epithelial cell adhesion molecule (EPCAM) (Origene, RC201989) into a CHO-K1 cell (ATCC, CCL-61). The bindings of the antibodies contained in the clone supernatant to the cell were measured by flow cytometry. For the flow cytometry, BV421 Goat Anti-Mouse Ig was used. In order to select clones that provide supernatant that does not exhibit binding activity on EpCAM expressing cells, clones that bind to the cells were excluded. As a positive control, CD326 (EpCAM) Monoclonal Antibody (1B7) (eBioscience, 14-9326) was used.

Through this experiment, clones providing antibodies that bind to ten out of the twelve peritoneal disseminated cancer cells but do not bind to human EpCAM were selected.

2. Check of Binding of Antibody to Human Peripheral Blood Mononuclear Cell

Besides, in order to select clones providing antibodies selectively bind to a peritoneal disseminated cancer cell, clones providing antibodies that bind to a human peripheral mononuclear cell were excluded.

Flow cytometry was used to measure the binding between the human peripheral blood mononuclear cell and the antibody provided by each clone. As the human peripheral blood-derived mononuclear cell, Human Mononuclear Cells from Peripheral Blood (hMNC-PB), pooled, ultra-pure (PromoCell, C-12908) was used. For the flow cytometry, PE Goat Anti-Mouse Ig (Multiple Adsorption) (Becton, Dickinson and Company, 550589, or less, "PE Goat Anti-Mouse Ig"), BV421 Mouse Anti-Human CD3 (Becton, Dickinson and Company, 562426), APC Mouse Anti-Human CD14 (Becton, Dickinson and Company, 555399), and BB515 Mouse Anti-Human CD19 (Becton, Dickinson and Company, 564456) were used.

3. Purification of Antibody from Hybridoma Supernatant

The clone selected in steps 1. and 2. of Example 1-3 was cultured in a CD hybridoma medium (Thermo Fisher Scientific, 11279023). Using MabSelectSuRe (GE Healthcare, 17-5438-02), an antibody was purified from the culture supernatant (hereinafter referred to as "purified antibody"). The antibody was purified according to a conventional method.

4. Binding of Purified Antibody to Cultured Human Peritoneal Mesothelial Cell

In order to select antibodies that selectively bind to the peritoneal disseminated cancer cell, antibodies that bind to the cultured human peritoneal mesothelial cell were excluded from the purified antibody obtained in step 3. of Example 1-3. Human Mesothelial Cells (Zenbio, IVIES-F, Lot. MESM012916B) (herein referred to as "cultured human peritoneal mesothelial cells") were used as cultured human peritoneal mesothelial cells and cultured in a Mesothelial Cell Growth Medium (Zenbio, MSO-1). Flow cytometry was used for measuring the binding between the purified antibody and the cultured human peritoneal mesothelial cell. For flow cytometry, PE Goat Anti-Mouse Ig was used. Antibodies that do not bind or weakly bind to the cultured human peritoneal mesothelial cell were selected, to obtain fourteen purified antibodies (hereinafter referred to as "fourteen purified antibodies").

Example 1-4: Identification of Antigen Molecule Candidate Recognized by Obtained Antibody With respect to the fourteen purified antibodies, antigen candidate molecules were identified. As an example of the identification method, a method for identifying an antigen candidate molecule of 16B11, 16B12 and 21F7 will be described in detail.

As control antibodies in this experiment, 5D3, 9A1, and 21A3 having different binding patterns to the peritoneal disseminated cancer cell from 16B11 were used.

A cell lysate of NSC-15CF cells was prepared. To the cell lysate, was added any one antibody of 16B11, 16B12, 21F7, and three control antibodies (5D3, 9A1, and 21A3). Dynabeads Protein G (Life Technologies Corp., 10003D) was further added thereto, followed by stirring and washing. A protein having bound to Dynabeads Protein G was digested with Trypsin/LysC (Promega, V5072), to obtain a peptide mixture. A solution containing the peptide mixture was subjected to LC-MS/MS measurement using Ultimate 3000 RS nano (Thermo Fisher Scientific) and Obitrap Fusion (Thermo Fisher Scientific). The thus obtained LC-MS/MS data was subjected to comparative quantitative analysis and peptide/protein identification using software of Progenesis QI for Proteomics (Waters) and Mascot (Matrix Science Corporation) to identify the binding protein. The data obtained from 16B11, 16B12 or 21F7 was compared with the data obtained from the control antibodies, and TSPAN8 was identified as an antigen candidate molecule of 16B11 and 21F7. An antigen candidate molecule of 16B12 could not be identified in this experiment.

A similar experiment was performed by a similar method on 5B7, 9F6, 12C12, 13A9, 15D1, 18C10, and 19E4, and TSPAN8 was identified as an antigen candidate molecule. As control antibodies, 24C7 was used in addition to 5D3, 9A1, and 21A3. Although an antigen candidate molecule of 16B12 could not be identified, this antibody exhibited a similar binding profile to 16B11 in Example 1-3, and hence subsequent examination was performed assuming that TSPAN8 was an antigen candidate.

For further specifying an antigen, an experiment of binding to a human TSPAN8-Myc-DDK expressed CHO-K1 cell was performed. The human TSPAN8-Myc-DDK expressed CHO-K1 cell was produced by transfecting TSPAN8 (Myc-DDK-tagged)-Human tetraspanin 8 (TSPAN8) (ORIGENE, RC202694) (SEQ ID NO: 2) into a CHO-K1 cell. As a result, it was confirmed that ten antibodies of 16B11, 16B12, 5B7, 9F6, 12C12, 13A9, 15D1, 18C10, 19E4 and 21F7 (referred to also as the "ten anti-TSPAN8 antibodies") bound to the human TSPAN8-Myc-DDK expressed CHO-K1 cell, and recognize TSPAN8 as an antigen.

Example 1-5: Check of Binding Activity of Anti-TSPAN8 Antibody to Various Cells 1. Check and Quantification of Binding Activity to Peritoneal Disseminated Cancer Cell Bindings of four anti-TSPAN8 antibodies to seven peritoneal disseminated cancer cells (KM-291-As, KM-555-As, KM-556-As, P-249-As, KM-568-As, KM-570-As and KM-577-As) isolated from the ascites fluids of gastric cancer patients were measured by flow cytometry.

KM-291-As was prepared from the patient's ascites fluids using the same method as in Example 1-1. Since the KM-291-As prepared contained many blood cells expressing CD45, the CD45 expressing cells were removed with a column in order to concentrate the cancer cells. Specifically, a cell suspension containing $5\times10^7$ cells was passed through Pre-Separation Columns (30 µm) (Miltenyi Biotec, 130-041-407) and Separation Columns (Miltenyi Biotec, 130-042-401) (hereinafter referred to as "Columns") using CD45 MicroBeads, human (Miltenyi Biotec, 130-045-801) according to a conventional method. The column eluate was collected in a 50 mL centrifuge tube, followed by centrifugation. 10 mL of buffer was added to the precipitate to suspend the cell again. From this cell suspension, $5\times10^6$ cells were dispensed into a 1.5 mL microtube (WATSON, 131-7155C), to obtain a precipitate by centrifugation. To the resultant precipitate, were added 950 µL of PBS (FCM buffer) containing 2% FBS and 100 g/mL Penicillin-Streptomycin (Thermo Fisher Scientific, 15140-122), to prepare a cell suspension. 50 µL of FcR Blocking Reagent was added thereto to perform a reaction in ice for 10 minutes. The thus obtained reaction solution was dispensed into seven 1.5 mL microtubes in an amount of 100 µL each, and cells were stained by the following method. To each of three microtubes out of seven, 5 µL of mouse IgG1-PE antibody (Miltenyi Biotec, 130-092-212) was added, and 2.5 µL of Alexa Fluor647-labeled control antibody was added to each of the microtubes to obtain Isotype controls. As the control antibody, any of mouse IgG2a Isotype control (Becton, Dickinson and Company, 558053), mouse IgG2b Isotype control (Becton, Dickinson and Company, 558713), and mouse IgG3 Isotype control (Becton, Dickinson and Company, 560803) was used. To each of the other four microtubes, 5 µL of CD326 (EpCAM)-PE (Miltenyi Biotec, 130-091-253) was added, 2.5 µL (0.25 g/tube) of 16B11, 16B12, 9F6 or 18C10 was added to each of the microtubes, and the cell was stained to obtain four evaluation antibody samples. In each of the microtubes, a reaction was performed in ice for 30 minutes after adding the antibody. 1 mL of FCM buffer was added thereto, followed by centrifugation, and 500 µL of FCM buffer was added to the precipitate obtained to suspend the cell again. To the resultant, 5 µL of 7-AAD (Becton, Dickinson and Company, 559925) was added, the whole amount was transferred to a 5 mL round bottom polystyrene tube equipped with a cell strainer cap (CORNING, 352235), and measurement was performed using FACSVerse flow cytometer (Becton, Dickinson and Company). For data acquisition, BD FACSuite software (Becton, Dickinson and Company) was used.

KM-555-As, KM-556-As, P-249-As, KM-568-As, KM-570-As, and KM-577-As were prepared in the same manner as in the preparation of KM-291-As. In the measurement of the binding to KM-555-As and KM-556-As, 16B11, 9F6 and 18C10 were used as evaluation antibody samples. In the measurement of the binding to P-249-As, 16B11 and a commercially available anti-TSPAN8 antibody TSPAN8 Antibody, anti-human, REAfinity (130-106-855, Miltenyi, herein referred to as "REA443") were used as evaluation antibody samples. In the measurement of the binding to KM-568-As, KM-570-As, KM-577-As, 16B11, 9F6, 18C10 and REA443 were used as evaluation antibody samples. In all the experiments, Isotype Control Antibody, mouse IgG1 (130-113-196, Miltenyi) was used as an isotype control. Further, for staining the cell, IgG2a-VioBlue antibody (Miltenyi Biotec, 130-113-277) and CD326(EpCAM)-VioBlue antibody (Miltenyi Biotec, 131-113-266) was used.

The analysis of the measurement results by flow cytometry of each peritoneal disseminated cancer cell was performed using BD FACSuite software. Specifically, data was plotted in FSC-A (lin)/SSC-A (log), the resultant cell population was gated, the resultant was expanded in FSC-W (lin)/FSC-A (lin) again, and only a singlet population was gated to create a subset for the analysis. In the analysis of the measurement results obtained from the KM-291-As cell, the subset was expanded in PE (log)/Alexa Fluor 647 (log). In the analysis of the measurement results obtained from KM-555-As, KM-556-As, P-249-As, KM-568-As, KM-570-As, and KM-577-As, data expanded in VioBlue (log)/Alexa Fluor 647 (log) was used. For each sample, data was obtained using a subset of $1\times10^4$ cells. The thus obtained fcs file was analyzed with FlowJo (Becton, Dickinson and Company) to create a histogram with Alexa Fluor 647. MFIs of Alexa Fluor 647 of groups positive for the evaluation antibodies were respectively calculated, and AMFI was calculated by subtracting the isotype MFI from the MFI of each antibody (Table 1).

Figures 1, 2:
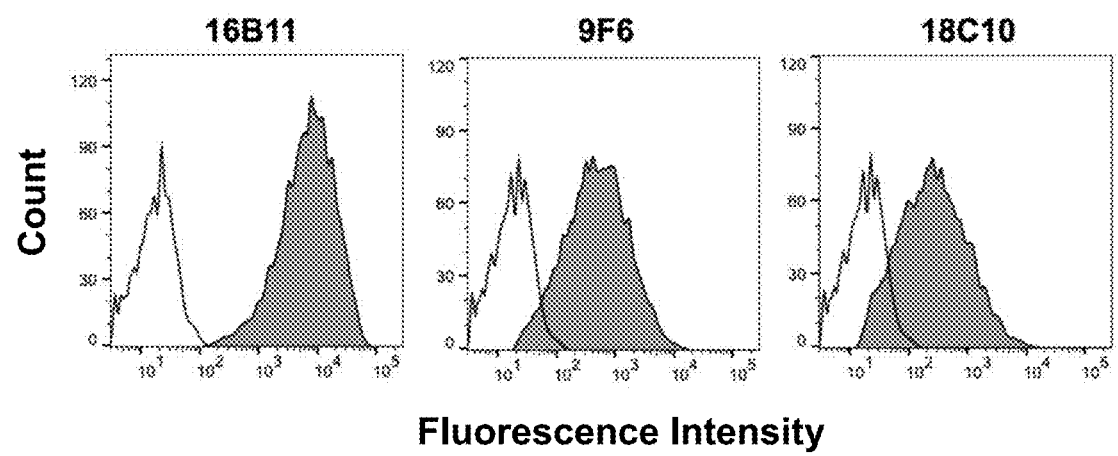
Figures 1, 2, 3:
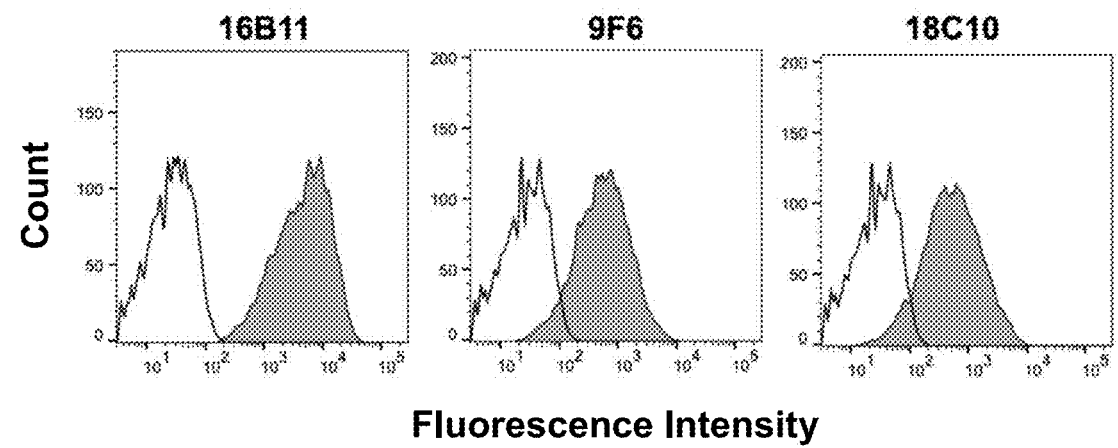
Figures 1, 2:
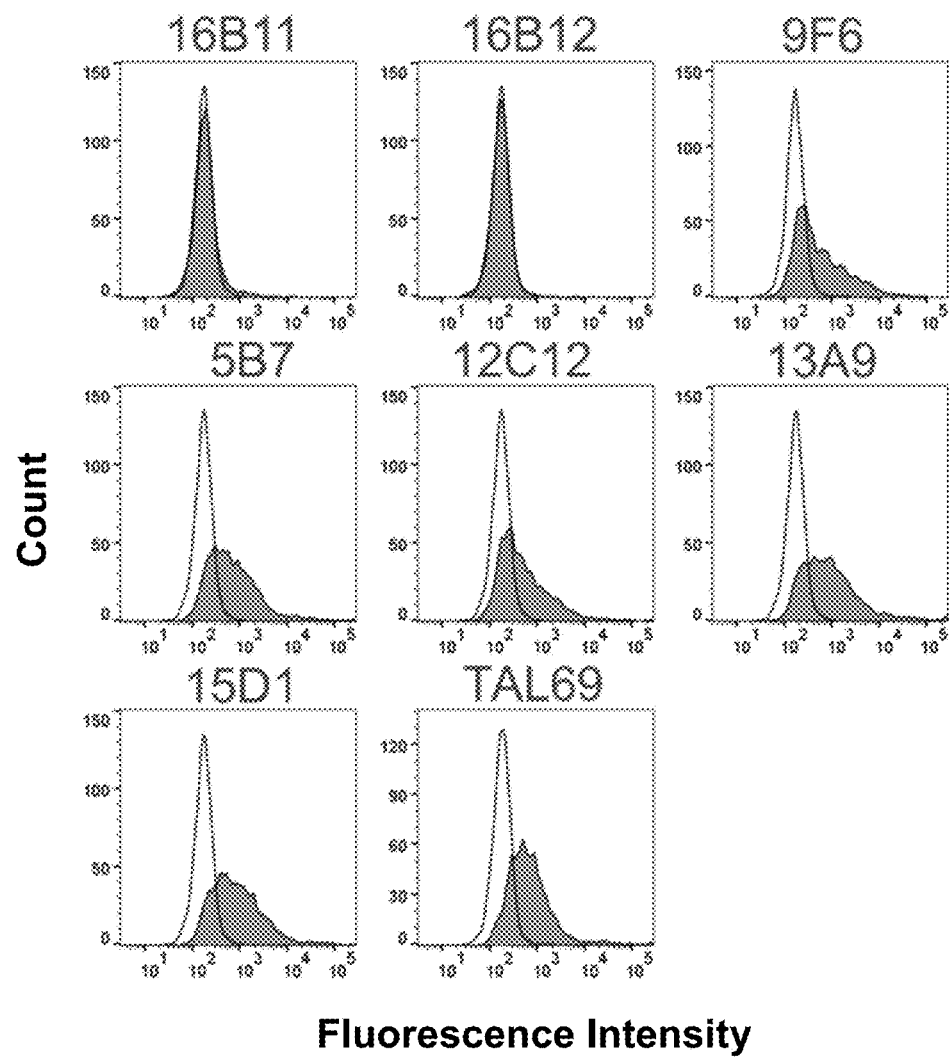
Figure 2:
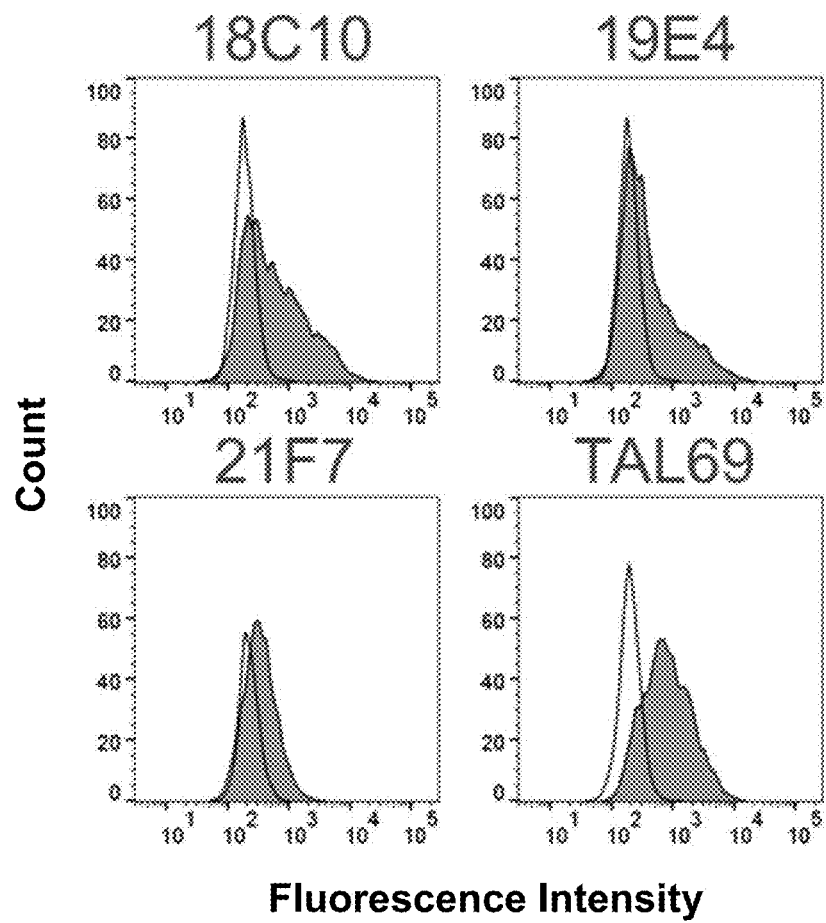
Figures 1, 3:
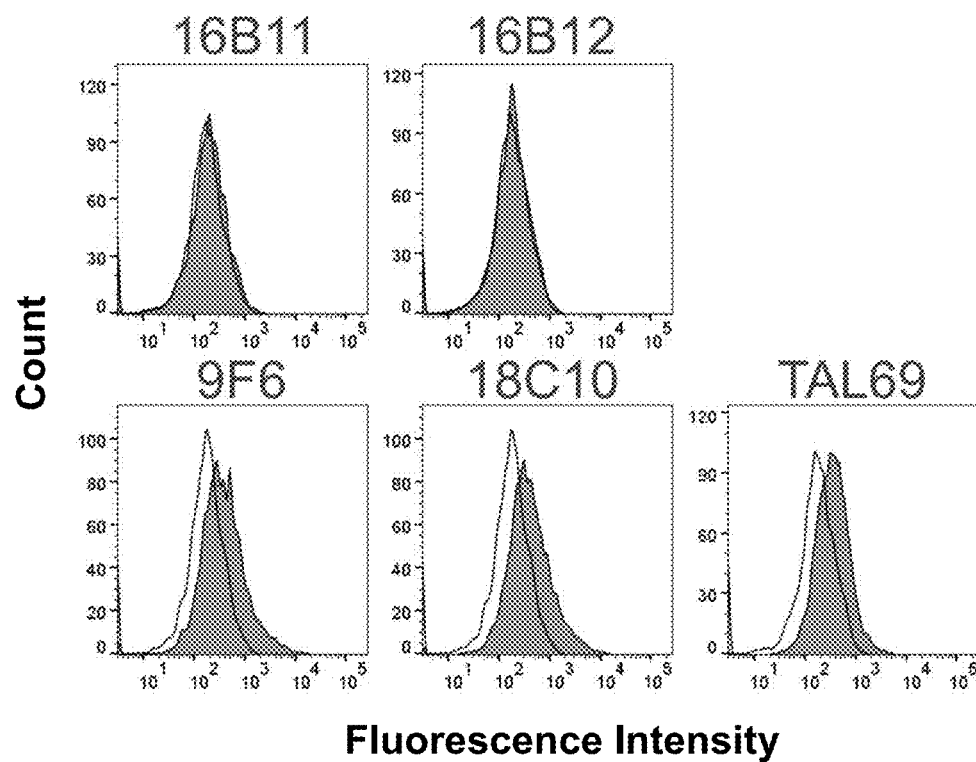
Figures 2, 3:
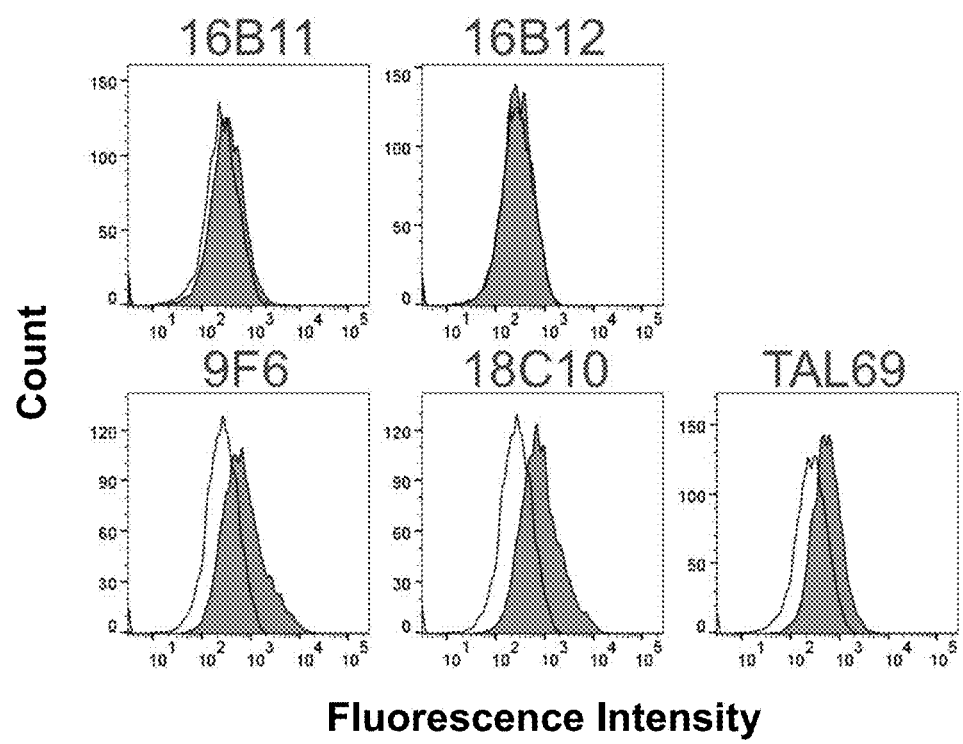

As examples of the histograms obtained, FIG. 1-1 to FIG. 1-3 respectively illustrate histograms showing the bindings of 16B11, 9F6, 18C10 in the binding measurement of 16B11 to KM-291-As and the binding measurement of 16B12 to KM-555-As and KM-556-As.

2. Check and Quantification of Binding Activity to Cultured Human Peritoneal Mesothelial Cell Binding activities of the ten of anti-TSPAN8 antibodies identified in Example 1-4 to a cultured human peritoneal mesothelial cell were measured. The cultured human peritoneal mesothelial cell is a normal cell.

Bindings of the ten anti-TSPAN8 antibodies obtained in Example 1-3 and a commercially available anti-TSPAN8 antibody, Purified anti-human TSPAN8 Antibody (BioLegend, 362702 Clone TAL69, herein referred to as "TAL69") to a cultured human peritoneal mesothelial cell were measured by flow cytometry. As a secondary antibody, PE Goat Anti-Mouse Ig was used. FIG. 2-1 and FIG. 2-2 show the histograms obtained. Further, the results of flow cytometry were analyzed with FlowJo, to calculate MFI for PE of each cell population. As negative control antibodies, three antibodies of Ultra-LEAF Purified Mouse IgG1, κ Isotype Ctrl Antibody (BioLegend, 401408), Purified NA/LE Mouse IgG2a, κ Isotype Control (Becton, Dickinson and Company, 554645) and Purified NA/LE Mouse IgG2b, κ Isotype Control (Becton, Dickinson and Company, 559530) were used for analysis. Table 1 shows the ΔMFI values of 16B11, 16B12, 9F6, 18C10 and TAL69. The ΔMFI value of each antibody was calculated by subtracting the MFI value of each negative control antibody from the MFI value of the antibody.

3. Check and Quantification of Binding Activity to Gastric Cancer with Peritoneal Disseminated Patient-derived Peritoneal Mesothelial Cell KM-501-As and KM-503-As, which were peritoneal mesothelial cells isolated from the ascites fluid of a human gastric cancer with peritoneal disseminated patient (herein, referred to as the "patient-derived peritoneal mesothelial cell"), was obtained as follows.

In the process of cell establishment of Example 1-1, a mesothelial cell was found to grow in a cobblestone manner over the dish. This mesothelial cell was collected using 0.05% trypsin-EDTA, and the resultant cell was suspended again in 10 mL of D-MEM (high glucose) (FUJIFILM Wako Pure Chemical Corporation, 044-29765) containing 10% FBS and ×1 Antibiotic-Antimycotic. $4 \times 10^5$ cells were dispensed into a 1.5 mL microtube, followed by centrifugation, supernatant was then removed, and 96 μL of FCM buffer was added thereto to suspend the cells. 4 μL of FcR Blocking Reagent was added thereto to perform a reaction in ice for 10 minutes. 50 μL of the resultant reaction solution was dispensed into another 1.5 mL microtube, and thus, two microtubes each holding $2 \times 10^5$ cells/50 μL were obtained. To one of the microtubes, 2 μL of CD45-APC antibody (Miltenyi Biotec, 130-091-230) and 0.5 μL of CD326 (EpCAM)-PE (Miltenyi Biotec, 130-113-264) were added. To the other microtube, 2 μL of mouse IgG2a-APC antibody (Miltenyi Biotec, 130-091-386) and 0.5 μL of mouse IgG1-PE antibody were added. In these microtubes, a reaction was performed in ice for 30 minutes. 1 mL of FCM buffer was added to each of the microtubes, followed by centrifugation, and supernatant was removed. 500 μL of FCM buffer was added to the precipitate to suspend the cells again, and analysis was performed using FACSVerse. A cell population was gated in FSC-A (lin) and SSC-A (log), and the resultant subset was expanded again in PE (log) and APC (log) to obtain data. The fcs files obtained were analyzed with FlowJo. As a result, this cell population was confirmed to be CD45-negative and EpCAM-negative normal cells. It is considered that the patient-derived peritoneal mesothelial cell is a normal cell derived from the caul or mesentery working as scaffold for engraftment and growth of a peritoneal disseminated cancer cell. KM-501-As and KM-503-As, that is, isolated patient-derived peritoneal mesothelial cells, were used in subsequent experiment.

The ten anti-TSPAN8 antibodies and TAL69 were bound to KM-501-As and KM-503-As in the same manner as in the binding measurement to the cultured human peritoneal mesothelial cell in step 2. of Example 1-5. FIG. 3-1 and FIG. 3-2 show the histograms of 16B11, 16B12, 9F6, 18C10 and TAL69 for KM-501-As and KM-503-As, and Table 1 shows the ΔMFI values.

4. Check and Quantification of Binding Activity to Cultured Human Umbilical Cord Vascular Endothelial Cell The bindings of the ten anti-TSPAN8 antibodies and TAL69 to the cultured human umbilical cord vascular endothelial cell were measured by flow cytometry. The cultured human umbilical cord vascular endothelial cell (PromoCell, C-12200) was cultured using Endothelial Cell Growth Medium 2 Kit (PromoCell, C-22111). As negative control antibodies, Ultra-LEAF Purified Mouse IgG1, κ Isotype Ctrl Antibody, Purified NA/LE Mouse IgG2a, κ Isotype Control, Ultra-LEAF Purified Mouse IgG2b, κ Isotype Ctrl Antibody (BioLegend, 400348), LEAF Purified Mouse IgG3, and κ Isotype Ctrl Antibody (BioLegend, 401310) were used. As a secondary antibody, PE Goat Anti-Mouse Ig was used.

Figure 4:
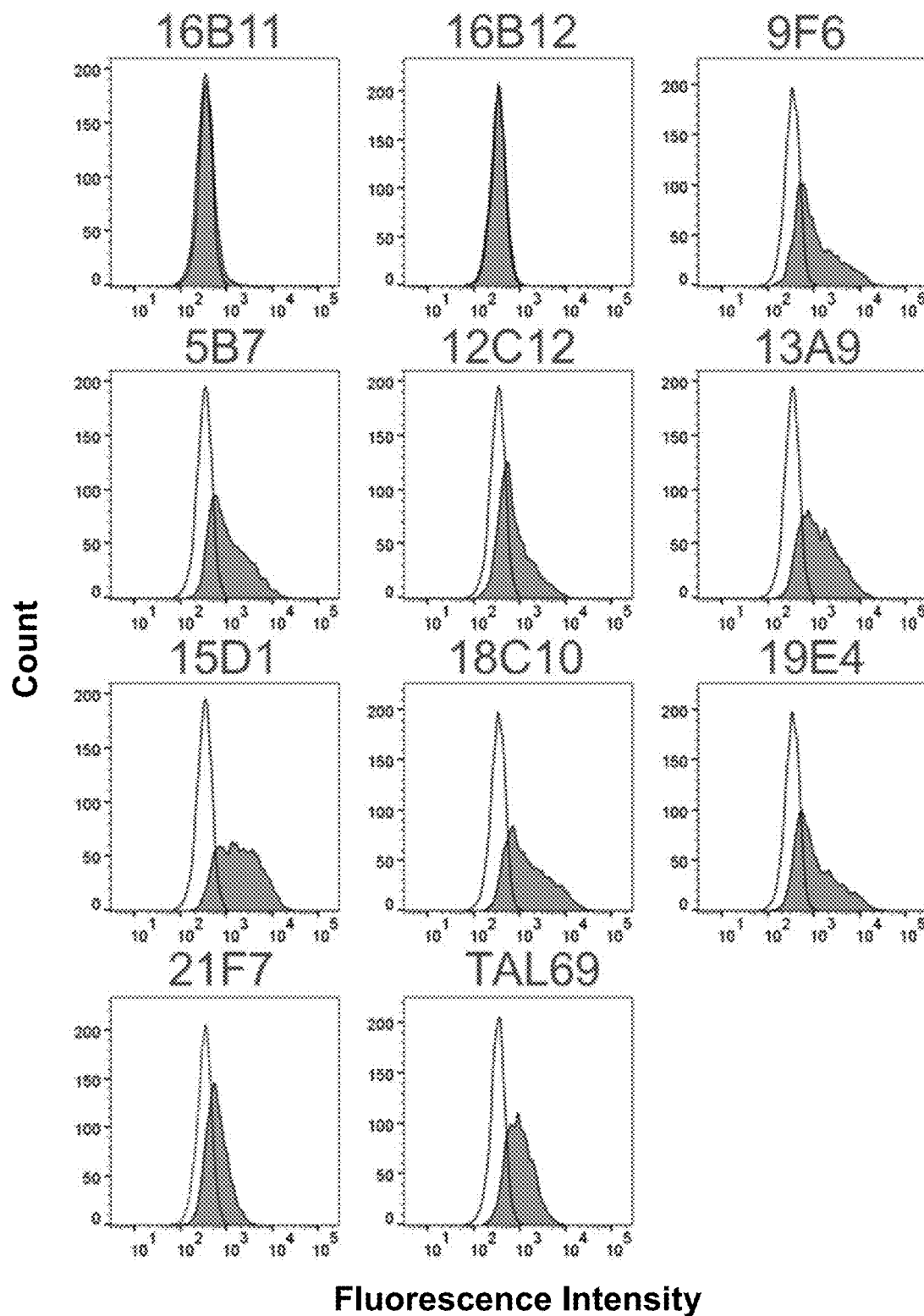
FIG. 4 illustrates results of measurement with flow cytometry of a binding of anti-TSPAN8 antibodies (16B11, 16B12, 9F6, 5B7, 12C12, 13A9, 15D1, 18C10, 19E4, 21F7, and TAL69) to a human umbilical cord vascular endothelial cell, donor 2. The abscissa of the drawing indicates fluorescence intensity, and the ordinate indicates the cell count. In the drawing, a white area indicates the binding of a negative control antibody, and a dark gray area indicates the binding of the anti-TSPAN8 antibody.

FIG. 4 shows the histograms of the bindings of the ten anti-TSPAN8 antibodies and TAL69. Table 1 shows the ΔMFI values for 16B11, 16B12, 9F6, 18C10 and TAL69. The ΔMFI value was calculated by subtracting the MFI value of each negative control antibody from the MFI value of each antibody.

It was demonstrated from the results of the histograms in FIG. 1 to FIG. 4 and the results in Table 1 that 16B11 and 16B12 exhibited a high binding to the peritoneal disseminated cancer cell but exhibited a low binding to a normal cell (cultured human peritoneal mesothelial cell, patient-derived peritoneal mesothelial cell, or cultured human umbilical cord vascular endothelial cell). Meanwhile, other anti-TSPAN8 antibodies exhibited a lower binding to a peritoneal disseminated cancer cell than 16B11 and 16B12 and a higher binding to a normal cell than 16B11 and 16B12. It was revealed from these results that the characteristics of 16B11 and 16B12 are significantly different from those of other anti-TSPAN8 antibodies (9F6, 18C10, TAL69, and the like).

TABLE 1

| Sample name | | 16B11 | 16B12 | 9F6 | 18C10 | Commercially Available Antibody (TAL69) | Commercially Available Antibody REA443 |
|---|---|---|---|---|---|---|---|
| Peritoneal Disseminated Cancer Cell | KM-291-As | 64032 | 37165 | 12096 | 11727 | n.t. (not tested) | n.t. |
| | KM-555-As | 10388 | n.t. | 920 | 447 | n.t. | n.t. |
| | KM-556-As | 6604 | n.t. | 820 | 846 | n.t. | n.t. |
| | P-249-As | 6735 | n.t. | n.t. | n.t. | n.t. | 87 |
| | KM-568-As | 29051 | n.t. | 2216 | 2634 | n.t. | 2796 |
| | KM-570-As | 13875 | n.t. | 274 | 326 | n.t. | 606 |
| | KM-577-As | 426 | n.t. | 6.6 | 8.8 | n.t. | 6 |

TABLE 1-continued

| Sample name | | 16B11 | 16B12 | 9F6 | 18C10 | Commercially Available Antibody (TAL69) | Commercially Available Antibody REA443 |
|---|---|---|---|---|---|---|---|
| Cultured Human Peritoneal Mesothelial Cell | Zenbio | 61 | 4 | 566 | n.t. | 616 | n.t. |
| | | n.t. | n.t. | n.t. | 370 | 583 | |
| Patient-derived Peritoneal Mesothelial Cell | KM-501-As | 23 | 5 | 206 | 230 | 181 | n.t. |
| | KM-503-As | 76 | 7 | 424 | 544 | 286 | n.t. |
| Cultured Human Umbilical Cord Vascular Endothelial Cell | Donor 1 | 0 | 2 | 11 | 3 | 3 | n.t. |
| | Donor 2 | 45 | 18 | 722 | 1117 | 633 | n.t. |
| | Donor 3 | −4 | −1 | 32 | 82 | 109 | n.t. |
| | Donor 4 | −5 | 3 | 19 | 58 | 92 | n.t. |
| | Donor 5 | −3 | −5 | 14 | 35 | 59 | n.t. |

Example 2: Sequence Determination of 16B11 and 16B12

A conventional method was employed to clone genes encoding heavy chains and light chains of 16B11 and 16B12 for sequence determination of these antibodies. Velocimmune technology is a technique for producing antibodies using transgenic mice in which the endogenous immunoglobulin heavy and light chain variable regions are replaced with the corresponding human variable regions. Therefore, the antibodies obtained using the velocimmune technique are antibodies having variable regions of the human antibody and constant regions of the mouse antibody (referred to also as chimeric antibodies). The amino acid sequence of the heavy chain variable region of 16B11 thus obtained is shown in SEQ ID NO: 34, and the amino acid sequence of the light chain variable region of the antibody is shown in SEQ ID NO: 36. The amino acid sequence of the heavy chain variable region of 16B12 thus obtained is shown in SEQ ID NO: 35, and the amino acid sequence of the light chain variable region of the antibody is shown in SEQ ID NO: 37.

Example 3: Production of Fully Human Anti-TSPAN8 Antibody

Example 3-1: Production of Expression Vector Used for Producing Fully Human Anti-TSPAN8 Antibody Fully human antibodies of 16B11 and 16B12 were produced by linking the amino acid sequence of the human variable region to the amino acid sequence of the human constant region identified in Example 2.

A polypeptide in which an amino acid sequence encoding a signal sequence shown in SEQ ID NO: 38 was linked to the N-terminal of the heavy chain variable region of each of 16B11 and 16B12, and an amino acid sequence of the human IgG1 constant region (a sequence from amino acid positions 122 to 451 of SEQ ID NO: 4 or 10) was linked to the C-terminal was designed. Besides, mutation for replacing arginine (R) at position 16 of a furin cleavage sequence consisting of an amino acid sequence corresponding to positions 16 to 19 in the heavy chain variable region of the polypeptide (J. Biol. Chem., 1992, Vol. 267, p. 16396-16402) with glycine (G) was introduced. A polynucleotide encoding the thus designed polypeptide was introduced into a pcDNA 3.4 TOPO (R) vector (Thermo Fisher Scientific). The thus produced heavy chain vectors were designated respectively as pcDNA3.4-16B11.1_HC and pcDNA3.4-16B12.1_HC.

Besides, a polypeptide in which an amino acid sequence encoding a signal sequence shown in SEQ ID NO: 39 was linked to the N-terminal of the light chain variable region of 16B11, an amino acid sequence encoding a signal sequence shown in SEQ ID NO: 40 was linked to the N-terminal of the light chain variable region of 16B12, and a constant region amino acid sequence of human κ chain (a sequence from amino acid positions 108 to 213 of SEQ ID NO: 8 or 12) was linked to the C-terminal of each of the both antibodies was designed. A polynucleotide encoding the thus designed polypeptide was introduced into a pcDNA 3.4 TOPO (R) vector. The thus produced light chain vectors were designated respectively as pcDNA3.4-16B11_LC and pcDNA3.4-16B12_LC.

Example 3-2: Production of Fully Human Anti-TSPAN8 Antibody

The vectors pcDNA3.4-16B11.1_HC and pcDNA3.4-16B11_LC were used for producing an antibody 16B11.1.

Specifically, into ExpiCHO-S cells (Thermo Fisher Scientific, A29127) having been cultured to a concentration of about 6.0×10⁶ cells/mL in ExpiCHOExpression Medium (Thermo Fisher Scientific, A2910001), the vectors pcDNA3.4-16B11.1_HC and pcDNA3.4-16B11_LC were transfected using a transfection reagent, ExpiFectamine-CHO Transfection Kit (Thermo Fisher Scientific, A29129), and the resultant was cultured for 12 days. Supernatant was purified with MabSelectSuRe to obtain a purified antibody of a fully human antibody. The thus obtained antibody is designated as 16B11.1. The nucleotide sequence of a heavy chain of 16B11.1 is shown in SEQ ID NO: 3, the amino acid sequence encoded thereby is shown in SEQ ID NO: 4, the nucleotide sequence of a light chain of the antibody is shown in SEQ ID NO: 7, and the amino acid sequence encoded thereby is shown in SEQ ID NO: 8.

16B12.1 can be produced by a similar method using the vectors pcDNA3.4-16B12.1_HC and pcDNA3.4-16B12_LC. The nucleotide sequence of a heavy chain of 16B12.1 is shown in SEQ ID NO: 9, the amino acid sequence encoded thereby is shown in SEQ ID NO: 10, the nucleotide sequence of a light chain of the antibody is shown in SEQ ID NO: 11, and the amino acid sequence encoded thereby is shown in SEQ ID NO: 12.

Example 4: Identification of Epitope Site on Antigen Side to Which Antibody Binds

Example 4-1: Epitope Mapping by Hydrogen/Deuterium Exchange Mass Spectrometry In order to identify the epitope of 16B11.1, hydrogen/deuterium exchange mass spectrometry (HDX-MS) was conducted. As a result, a human TSPAN8 region corresponding to amino acid positions 126 to 155 of SEQ ID NO: 2 was detected as a region in which the deuterium exchange degree decreases in the presence of 16B11.1. It was estimated from this result that the human TSPAN8 region corresponding to amino acid positions 126 to 155 of SEQ ID NO: 2 was the epitope of 16B11.1.

Example 4-2: Narrowing Down Important Epitopes by Introducing Human TSPAN8 Mutation In order to check whether or not the region estimated in Example 4-1 was the epitope of 16B11.1, a chimeric protein in which the region was replaced with a homologous region of mouse or rat TSPAN8 was produced, and the binding was evaluated. SEQ ID NO: 41 shows amino acid positions 126 to 155 of mouse TSPAN8 corresponding to amino acid positions 126 to 155 of human TSPAN8, and SEQ ID NO: 42 shows amino acid positions 126 to 155 of rat TSPAN8 corresponding thereto.

In order to produce a cell expressing a fusion protein of TSPAN8 and GFP, a human TSPAN8 sequence was cut out from TSPAN8 (Myc-DDK-tagged)-Human tetraspanin 8 (TSPAN8) (ORIGENE, RC202694) used in Example 1-4 using a restriction enzyme. Sub-cloning was performed on the cut-out human TSPAN8 sequence into pCMV6-AC-GFP vector (ORIGENE, PS100010) (hereinafter referred to as "human TSPAN8-GFP expressing vector"). Further, a vector in which a sequence corresponding to amino acid positions 126 to 155 of the human TSPAN8-GFP expressing vector shown in SEQ ID NO: 2 was replaced with mouse or rat TSPAN8 sequence of amino acid positions 126 to 155 was produced using In-Fusion(R) HD Cloning Kit (Takara Bio Inc., 639633). Each vector produced was introduced into the CHO-K1 cell, to produce a cell transiently expressing a human TSPAN8-GFP protein, a human mouse TSPAN8-GFP chimeric protein or a human rat TSPAN8-GFP chimeric protein. The cell produced will be referred to as a wild-type human TSPAN8 expressing CHO-K1 cell, a human mouse TSPAN8 chimeric protein expressing CHO-K1 cell or a human rat TSPAN8 chimeric protein expressing CHO-K1 cell. Further, a cell in which a pCMV6-AC-GFP vector was introduced into a CHO-K1 cell (referred to as a mock cell) was produced. The bindings of 16B11, 16B12 and TAL69 to GFP-positive cells in these cells were measured by flow cytometry. No decrease in binding of TAL69 was observed either to the human rat or human mouse TSPAN8 chimeric protein expressing CHO-K1 cell. 16B11 and 16B12 exhibited the same binding to the human rat TSPAN8 chimeric protein expressing CHO-K1 cell as the wild-type human TSPAN8 expressing CHO-K1 cell. Meanwhile, the binding to the human mouse TSPAN8 chimeric protein expressing CHO-K1 cell attenuated as compared with that to the wild-type human TSPAN8 expressing CHO-K1 cell (FIG. 5-1).

In order to specify the amino acid sequence contributing to the attenuation of the binding activity to the human mouse TSPAN8 chimeric protein expressing CHO-K1 cell, sequences of human, mouse, rat and cynomolgus monkey TSPAN8 proteins corresponding to 126 to 155 of the amino acid sequence of human TSPAN8 were compared (FIG. 5-2). SEQ ID NOs: 41, 42 and 43 respectively show sequences corresponding to 126 to 155 of amino acid sequences of mouse, rat and cynomolgus monkey TSPAN8. As a result, only the amino acid at position 131 had a different amino acid sequence in the mouse TSPAN8 protein. It was inferred from this information that threonine (T) at position 131 of the human TSPAN8 protein shown in SEQ ID NO: 2 was important for the binding of 16B11 or 16B12.

Further, in order to check whether or not the amino acid at position 131 of human TSPAN8 contributed to the binding of 16B11 or 16B12, a substitute of the amino acid was produced. Specifically, a vector containing a nucleotide sequence encoding a human TSPAN8-GFP fusion protein in which threonine (T) at position 131 of the amino acid sequence of human TSPAN8 in human TSPAN8-GFP of SEQ ID NO: 2 was replaced with alanine (A) or asparagine (N) (respectively referred to as "human TSPAN8(T131A)-GFP" or "human TSPAN8(T131N)-GFP") was produced, and such a vector was transfected into the CHO-K1 cell, to construct a cell transiently expressing human TSPAN8(T131A)-GFP or human TSPAN8(T131N)-GFP. The cell constructed will be referred to as a human TSPAN8(T131A) expressing CHO-K1 cell or a human TSPAN8(T131N) expressing CHO-K1 cell. The bindings of 16B11, 16B12 and TAL69 to GFP-positive cells in these cells were measured by flow cytometry (FIG. 5-3). As a result, the bindings of 16B11 and 16B12 to the human TSPAN8(T131A) expressing CHO-K1 cell and the human TSPAN8(T131N) expressing CHO-K1 cell attenuated as compared with the bindings to the wild-type human TSPAN8 expressing CHO-K1 cell. Meanwhile, TAL69 exhibited an equivalent binding activity to any of the cells. As a result, it turned out that threonine at position 131 was an essential amino acid for the bindings of 16B11 and 16B12 in the region of human TSPAN8, which was identified as an epitope, corresponding to amino acid positions 126 to 155 of SEQ ID NO: 2.

Table 2-1 shows the ΔMFI value calculated by subtracting the MFI of the binding to the mock cell from the MFI of the binding to each TSPAN8 expressing cell. Further, Table 2-2 shows the ΔMFI relative values of the bindings to the human mouse TSPAN8 chimeric protein expressing CHO-K1 cell, the human rat TSPAN8 chimeric protein expressing CHO-K1 cell and the human TSPAN8(T131A or T131N) expressing CHO-K1 cell when the ΔMFI of the binding to the wild-type human TSPAN8 expressing CHO-K1 cell shown in Table 2-1 is taken as 100.

TABLE 2-1

|  | 16B11 | 16B12 | TAL69 |
| --- | --- | --- | --- |
| Human TSPAN8 (Wild type) | 172723 | 26673 | 132771 |
| Human rat chimeric TSPAN8 | 160579 | 22352 | 96180 |
| Human mouse chimeric TSPAN8 | 5274 | 102 | 304830 |
| Human TSPAN8(T131A) | 23373 | 12189 | 184065 |
| Human TSPAN8(T131N) | 3457 | 2629 | 143332 |

TABLE 2-2

|  | 16B11 | 16B12 | TAL69 |
| --- | --- | --- | --- |
| Human TSPAN8 (Wild type) | 100 | 100 | 100 |
| Human rat chimeric TSPAN8 | 93 | 84 | 72 |

TABLE 2-2-continued

|  | 16B11 | 16B12 | TAL69 |
|---|---|---|---|
| Human mouse chimeric TSPAN8 | 3 | 0 | 230 |
| Human TSPAN8(T131A) | 14 | 46 | 139 |
| Human TSPAN8(T131N) | 2 | 10 | 108 |

Example 4-3: Binding Competition Experiment

Whether or not 16B11 or 16B12 competes with other anti-TSPAN8 antibodies (9F6, 18C10 or TAL69) in binding to TSPAN8 was examined.

Figures 1, 6:
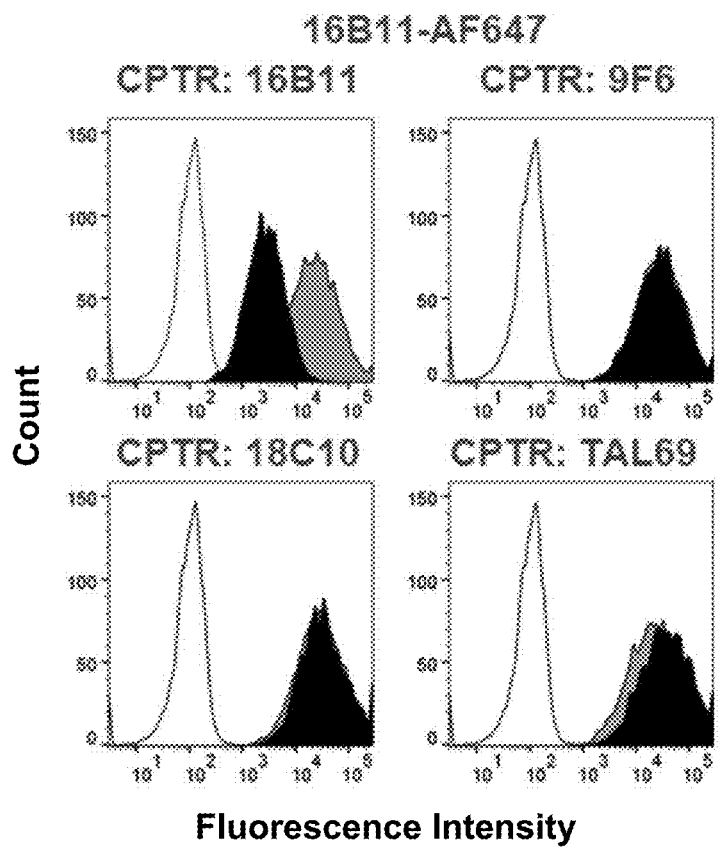
Figures 2, 6:
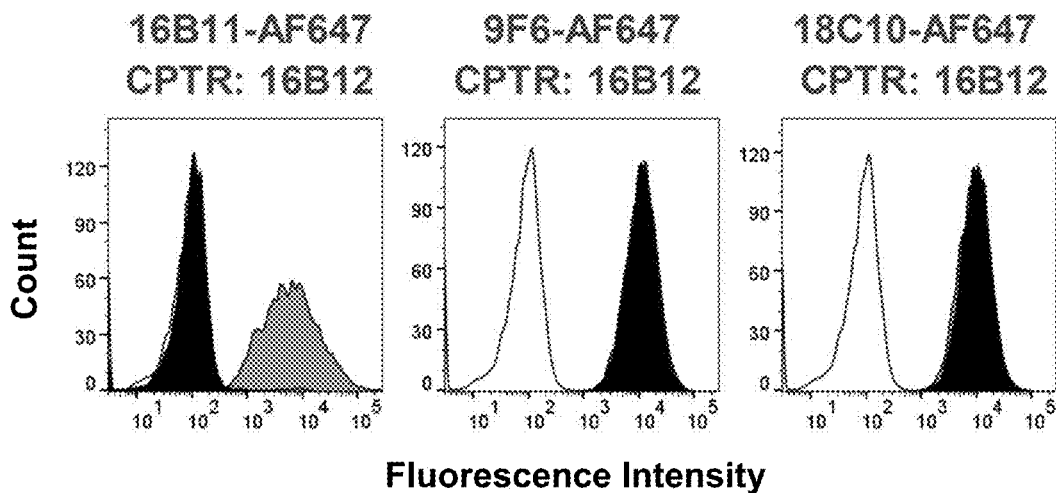
Figures 3, 6:
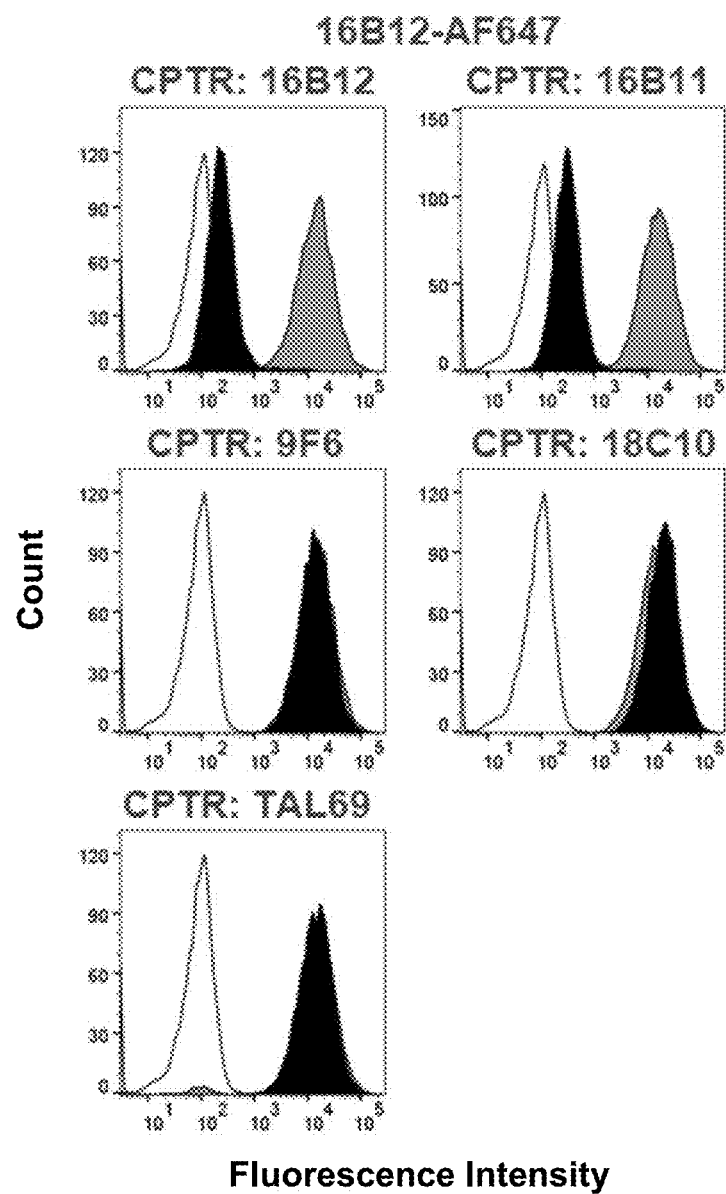

In order to examine competition of 16B11 with other anti-TSPAN8 antibodies (9F6, 18C10 or TAL69), changes in amount of 16B11 bound to the NSC-15CF cell were measured by flow cytometry (Experiment 1; FIG. 6-1). Specifically, Alexa Fluor647-labeled 16B11 at a final concentration of 1 µg/mL and another anti-TSPAN8 antibody (one antibody of 16B11, 9F6, 18C10 and TAL69) at a final concentration of 100 µg/mL were added to 2×10$^5$ of NSC-15CFs to give a final concentration of 100 µg/mL, and the amount of 16B11 bound to the NSC-15CFs was measured by flow cytometer. As negative control antibodies, Ultra-LEAF Purified Mouse IgG1, κ Isotype Ctrl Antibody, Ultra-LEAF Purified Mouse IgG2a, κ Isotype Ctrl Antibody (BioLegend, 400264), Ultra-LEAF Purified Mouse IgG2b, and κ Isotype Ctrl Antibody were used. As a result, the binding of 16B11 attenuated only when 16B11 itself was added.

In order to examine the competition of 16B12 with other anti-TSPAN8 antibodies (16B11, 9F6, 18C10 or TAL69), changes in amount of 16B11, 9F6 or 18C10 bound to the NSC-15CFs due to 16B12 were measured by flow cytometry (Experiment 2; FIG. 6-2). Specifically, Alexa Fluor647-labeled 16B11, 9F6 or 18C10 at a final concentration of 0.25 µg/mL and 16B12 at a final concentration of 100 µg/mL were added to 1×105NSC-15CFs, and the amount of 16B11, 9F6 or 18C10 bound to the NSC-15CF was measured by flow cytometer. As negative control antibodies, LEAF Purified Mouse IgG3 and κ Isotype Ctrl Antibody were used. As a result, the binding of 16B11 attenuated due to 16B12. There was no influence on the bindings of the other antibodies. Likewise, competition experiments using Alexa Fluor647-labeled 16B12 and other anti-TSPAN8 antibodies (16B11, 16B12, 9F6, 18C10 or TAL69) were conducted (Experiment 3; FIG. 6-3). As negative control antibodies, LEAF Purified Mouse IgG3, Isotype Ctrl Antibody, Ultra-LEAF Purified Mouse IgG2a, κ Isotype Ctrl Antibody, Ultra-LEAF Purified Mouse IgG2b, κ Isotype Ctrl Antibody and Ultra-LEAF Purified Mouse IgG1, and κ Isotype Ctrl Antibody were used. As a result, the binding of 16B12 attenuated only when 16B11 and 16B12 itself were added. Since the bindings of 16B11 and 16B12 competed with each other, it was inferred that 16B11 and 16B12 recognized similar epitopes. Table 3 shows relative values when competitive antibodies were added with respect to a value, calculated by subtracting the MFI of unstained cells from the MFI of the binding of each labeled antibody when the Isotype Control was added as the competitive antibody, taken as 100.

TABLE 3

| Experiment 1 | |
|---|---|
| Competitive antibody | % with respect to competition by isotype control |
| 16B11 | 12 |
| 9F6 | 98 |
| 18C10 | 119 |
| TAL69 | 180 |

| Experiment 2 | |
|---|---|
| Fluorescently labeled antibody | % with respect to competition by isotype control |
| 16B11 | 0 |
| 9F6 | 100 |
| 18C10 | 109 |

| Experiment 3 | |
|---|---|
| Competitive antibody | % with respect to competition by isotype control |
| 16B12 | 1 |
| 16B11 | 2 |
| 9F6 | 94 |
| 18C10 | 133 |
| TAL69 | 112 |

Example 5: Production of 60As6-Luc/GFP cell

A 60As6-Luc/GFP cell in which a luciferase protein and a green fluorescence protein (GFP) were expressed in a 60As6 cell as a cell line derived from ascites fluids of gastric cancer patients was produced by the following method.

Example 5-1: Production of Virus Solution Containing Luc/GFP

Lentivirus was produced using L293 T cells (Thermo Fisher Scientific, K4975-00) according to a conventional method.

For producing the lentivirus, MISSION(R) Lentiviral Packaging Mix (SIGMA, SHP001) and pCDH-CMV-GL3-EFla-GFP-T2A-puro modified vector (donated by Ryou-u Takahashi, Associate Professor, the Laboratory of Cellular and Molecular Biology, Graduate School of Biomedical and Health Sciences, Hiroshima University (PLoS One, 2015, Vol. 10, e0123407, and Front Biosci., 2008, Vol. 13, p. 1619-1633)) were used. Virus was filtered from the culture supernatant of cells containing the virus using a 45 µm Millex(R)-HV filter (Merck KGaA EMD Millipore Corporation, SLHVO33RS) to prepare a virus solution, and it was cryopreserved at −80° C.

Example 5-2: Infection of 60As6 Cell with Virus

The 60As6 cell (donated by Dr. Kazuyoshi Yanagihara, National Cancer Center Hospital) was infected with the virus according to a conventional method. As a medium, RPMI-1640 containing 10% FBS was used. The culture fluid was removed from the 60As6 cell plate 3 days after the infection to be replaced with RPMI-1640 (selection medium) containing 10% FBS and 2 g/mL of Puromaycin (Thermo Fisher Scientific, A-11138-02), and the culture was continued. Thereafter, the culture and the passage in the selection medium were repeated to remove uninfected cells, and it was checked that the virus had been completely removed. The thus established cell was designated as 60As6-Luc/GFP cell. This cell expressed luciferase and GFP. Besides, it was confirmed by flow cytometry that the 60As6-Luc/GFP cell endogenously expresses TSPAN8 at high level.

Example 6: Evaluation of ADCC Activity of Fully Human Antibody 16B11.1

The ADCC activity induced by a fully human antibody anti-TSPAN8 antibody 16B11.1 was measured. The ADCC activity can be measured by evaluating the action of an effector cell to damage a target cell. In this example, the cytotoxic activity was measured using Luciferase as an index, in which an NK cell is activated by 16B11.1 in a co-culture of the NK cell as the effector cell and the 60As6-Luc/GFP cell as the target cell, as a result of which the 60As6-Luc/GFP cell is damaged by the ADCC activity.

As the NK cell, a cell isolated from cryopreserved human PBMC (ePBMC(R), Characterized by Cryopreserved Human PBMC, Cellular Technology Limited, CTL-CP1) with NK Cell Isolation Kit, human (Miltenyi Biotec, 130-092-657) and cultured in an NK cell medium (NK MACS Medium, Miltenyi Biotec, 130-114-429) was used.

The 60As6-Luc/GFP cell and the NK cell suspended in a 5% FBS (Hyclone, SH30084.03)-containing RPMI-1640 (SIGMA, R8758-500 mL) medium were seeded in a round bottom 96 well plate (Sumitomo Bakelite, MS-9096U) respectively in amounts of $5\times10^3$ cells/25 μL/well and $5\times10^4$ cells/50 μL/well. Further, a solution obtained by diluting 16B11.1 or an in-house anti-KLH antibody (3G6) as a negative control antibody to give a final concentration of 1, 10, 100, 1000, or 10000 ng/mL was added in an amount of 25 μL/well, and the amount of luminescence of Luciferase 24 hours later was measured using a luciferase quantification kit (ONE-GloLuciferase Assay System, Promega Corp., E6120). Since the amount of luminescence of Luciferase indicates the viability of the 60As6-Luc/GFP cell, the cytotoxic activity by the ADCC activity can be measured by the decrease of the amount of luminescence of Luciferase.

Figure 7:
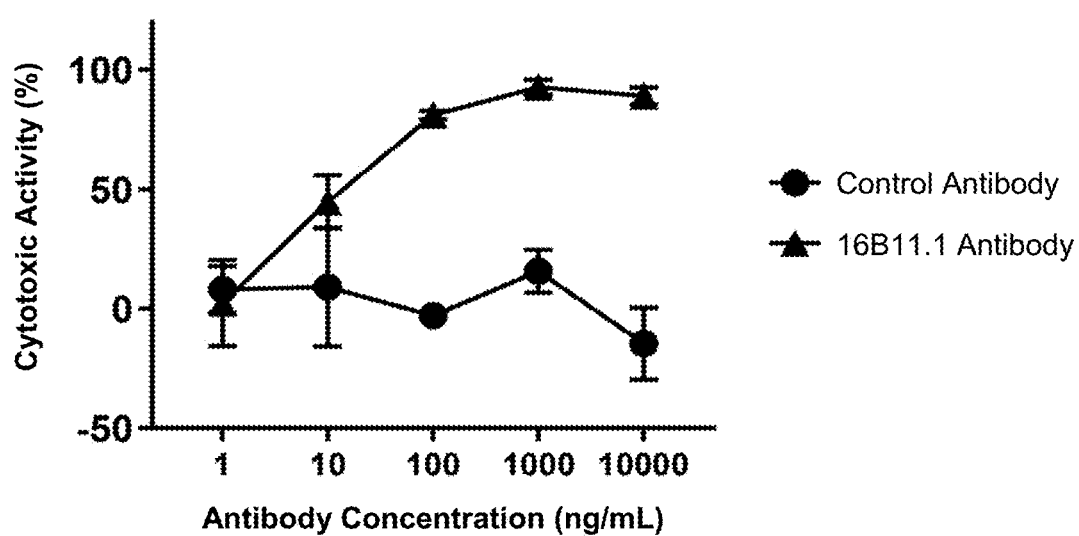
FIG. 7 illustrates cytotoxic activity of 16B11.1 in a co-culture system of 60As6-Luc/GFP cell and human NK cell. The abscissa indicates an antibody concentration, and the ordinate indicates cytotoxic activity calculated based on luciferase activity produced from the 60As6-Luc/GFP cell. ● and ▲ respectively indicate average values of cytotoxic activity at each concentration of a control antibody and 16B11.1. An error bar indicates a standard deviation.

The ordinate of FIG. 7 indicates relative values of the amount of luminescence of Luciferase of each sample when the amount of luminescence of Luciferase only in the medium is taken as 100%, and the amount of luminescence of Luciferase in the 60As6-Luc/GFP cell with no antibodies added is taken as 0%. The abscissa indicates a concentration of the antibody added to each well. As shown in FIG. 7, the target cell was damaged by the ADCC activity only when 16B11.1 was added.

Example 7: Production of Anti-TSPAN8/anti-CD3 Bispecific Antibody

Example 7-1: Production of Bispecific Antibody Vector of Anti-TSPAN8 Antibody

LALA mutation (L234A and L235A) in which amino acids corresponding to amino acid positions 238 and 239 (EU index: 234 and 235) of the heavy chain of 16B11.1 were respectively replaced from leucin (L) to alanine (A), knobs-into-holes mutation in which amino acids corresponding to amino acid positions 370, 372 and 411 (EU index: 366, 368 and 407) were respectively replaced from threonine (T) to serine (S), from L to A, and from tyrosine (Y) to valine (V), and mutation in which an amino acid corresponding to an amino acid position 301 (EU index: 297) was replaced from asparagine (N) to glycine (G) were introduced. The amino acid sequence of the heavy chain of 16B11.1 thus designed is shown in SEQ ID NO: 6. The thus produced vector is designated as pcDNA3.4-16B11.1_HC_H.

Example 7-2: Production of Bispecific Antibody Vector of Anti-human CD3 Antibody The sequence design of the humanized anti-CD3 antibody was performed based on sequences of a heavy chain variable region and a light chain variable region of a mouse anti-CD3 antibody described in Japanese Patent No. 5686953 in accordance with a method described in a literature (Front Biosci., 2008, Vol. 13, p. 1619-1633). Here, back mutation was introduced. Three-dimensional structure information (PDB Code: SFCS) was analyzed with Molecular Operating Environment MOE provided by MOLSIS Inc. to determine a position for introducing the back mutation in a frame work region. The humanized anti-CD3 antibody was designed in such a manner that a heavy chain variable region (corresponding to amino acid positions 1 to 125 of SEQ ID NO: 14), a linker (corresponding to amino acid positions 126 to 145 of SEQ ID NO: 14), a light chain variable region (corresponding to amino acid positions 146 to 254 of SEQ ID NO: 14), a hinge (corresponding to amino acid positions 255 to 269 of SEQ ID NO: 14), a CH2 domain (corresponding to amino acid positions 270 to 379 of SEQ ID NO: 14), and a CH3 domain (corresponding to amino acid positions 380 to 486 of SEQ ID NO: 14) were arranged in the stated order. Further, LALA mutation in which (1) amino acids at amino acid position 44 and an amino acid position 247 were replaced with cysteine (C), (2) an amino acid at amino acid position 259 (EU index: 220) was replaced from C to S, and (3) amino acids at amino acid positions 273 and 274 (EU index: 234 and 235) were replaced from L to A, Knobs-into-holes mutation in which (4) an amino acid at amino acid position 405 (EU index: 366) was replaced from T to tryptophan (W), and mutation in which (5) an amino acid at amino acid position 336 (EU index: 297) was replaced from N to G were introduced into SEQ ID NO: 14. For introducing these mutations, polynucleotides respectively encoding amino acid sequences including the respective mutation cites were synthesized to be inserted into a pcDNA 3.1(+) vector (Thermo Fisher Scientific, V79020). The thus produced vector is designated as pcDNA3.1-m7_scFV_K. A nucleotide sequence of the humanized anti-CD3 antibody thus produced is shown in SEQ ID NO: 13, and an amino acid sequence thereof is shown in SEQ ID NO: 14.

[Example 7-3: Production of Anti-TSPAN8/anti-CD3 Bispecific Antibody]

In order to produce a bispecific antibody including a Fab region of an anti-TSPAN8 antibody, a scFv region of an anti-CD3 antibody and a Fc region, the vectors pcDNA3.4-16B11.1_HC_H, pcDNA3.4-16B11 LC and pcDNA3.1-m7_scFV_K were transfected into the ExpiCHO—S(R) cell in the same manner as in Example 3. The thus obtained culture supernatant was purified with MabSelect SuRe, and further with gel filtration column HiLoad 26/600 Superdex (R) 200 pg (GE Healthcare, 28-9893-36), and thus, a purified antibody having a purity of 95% or more was obtained.

The thus obtained antibody was designated as the anti-TSPAN8(16B11)-anti-CD3 bispecific antibody.

Example 8: Evaluation of Binding Activity of Anti-TSPAN8/anti-CD3 Bispecific Antibody Binding activities of the anti-TSPAN8(16B11)-anti-CD3 bispecific antibody to TSPAN8 and CD3 were each evaluated by ELISA using LEL protein of TSPAN8 or CD3 complex protein.

Figures 1, 8:
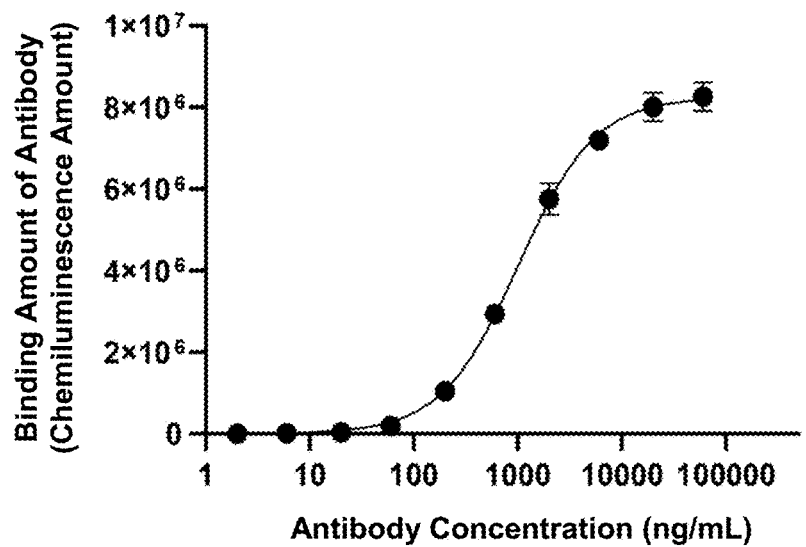
FIG. 8 illustrates binding activity of anti-TSPAN8 (16B11)-anti-CD3 bispecific antibody to LEL region peptide of TSPAN8 and CD3εδ complex protein. The abscissa indicates an antibody concentration, and the ordinate indicates a binding amount of the antibody.
Figures 2, 8:
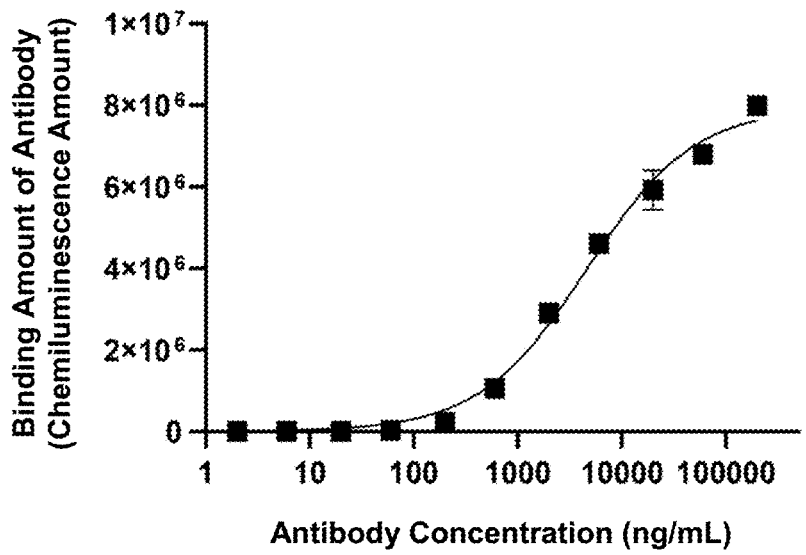

Specifically, 1 μg/mL of TSPAN8 Protein, Human, Recombinant (SinoBiological, 15683-H07H) or Human CellExp CD3 epsilon & CD3 delta Heterodimer, Human Recombinant (BioVision, P1183-10) diluted with PBS was added to a 384-Well White Plates, MaxiSorp (Nunc, 460372) at 30 μL/well. After standing still at 4° C. overnight, supernatant was removed, and Blocking One (Nacalai Tesque, 03953-95) was added thereto at 120 μL/well. After standing still at room temperature for 1 hour, supernatant was removed, and the resultant was washed with TBST buffer (Thermo Fisher Scientific, 28360) twice. The anti-TSPAN8(16B11)-anti-CD3 bispecific antibody diluted with TBST containing 10% Blocking One was added thereto at 30 μL/well, followed by standing still at room temperature for 1 hour. The resultant antibody solution was removed, washed with TBST buffer twice, Goat Anti-Human Kappa, Mouse ads-HRP (Southern Biotech, 2061-05) diluted by 5000 times with TBST containing 10% Blocking One was added thereto in an amount of 30 μL/well, and the resultant was stand still at room temperature for 30 minutes. The resultant antibody solution was removed, washed with TBST buffer four times, and BM Chemiluminescence ELISA Substrate (POD) (Roche, 11582950001) was added thereto in an amount of 30 μL/well. A reaction was performed at room temperature for 15 minutes, and then chemiluminescence was measured with ARVO X3 (Perkin Elmer). As a result, EC50 values for TSPAN8 and CD3 were calculated respectively as 1.0 μg/mL (8.1 nM) and 4.6 μg/mL (36 nM) (FIG. 8).

Figure 9:
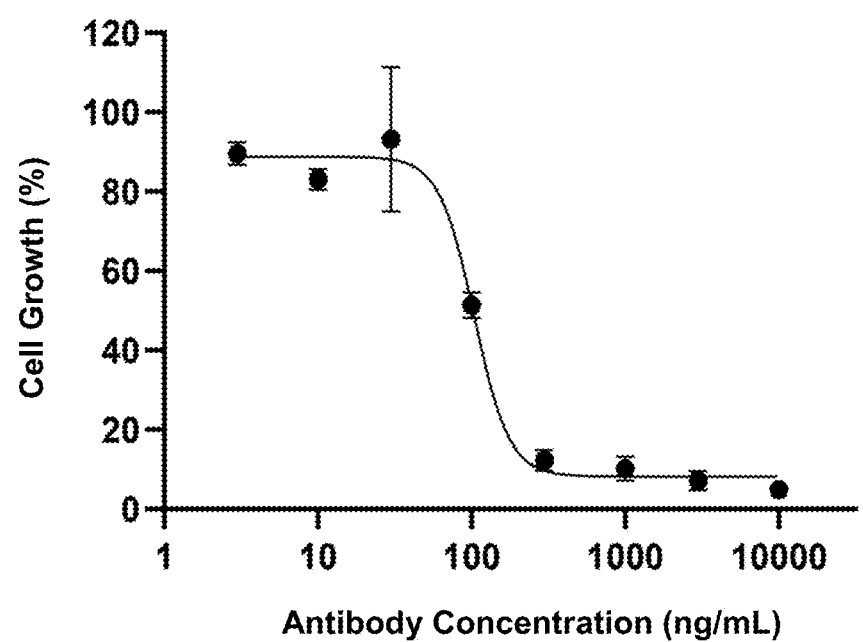
FIG. 9 illustrates cytotoxic activity of the anti-TSPAN8 (16B11)-anti-CD3 bispecific antibody in a co-culture system of 60As6-Luc/GFP cell and human peripheral blood mononuclear cell. The abscissa indicates an antibody concentration, and the ordinate indicates cell growth (%) of 60As6-Luc/GFP cell obtained 3 days after adding the antibody in a fluorescence area when the growth with no antibody added is 100%. ● indicates the average value of cell growth at each concentration of the anti-TSPAN8(16B11)-anti-CD3 bispecific antibody. An error bar indicates a standard deviation.

Example 9: Evaluation of RTCC Activity of Anti-TSPAN8/anti-CD3 Bispecific Antibody A medium prepared by adding, to 500 mL of RPMI-1640 (Thermo Fisher Scientific, 11875-119), 50 mL of FBS, 5 mL of MEM Non-essential Amino Acid (Merck, M7145), 5 mL of sodium pyruvate (Merck, S8636), 5 mL of GlutaMAX I (Thermo Fisher Scientific, 35050-061), 5 mL of penicillin streptomycin (Thermo Fisher Scientific, 15070-063), and 5 mL of HEPES (Thermo Fisher Scientific, 15630-080) was used as a culture medium (hereinafter referred to as "culture medium" in this example). A cell suspension prepared by culturing the 60As6-Luc/GFP cell produced in Example 4 in the culture medium to give $2\times10^5$ cells/mL was seeded in a flat bottom 96 well plate (IWAKI, 3860-096) in an amount of 50 μL for each and cultured in a 5% $CO_2$ incubator at 37° C. 3 hours later, a cryopreserved human peripheral blood mononuclear cell (LP. CR. MNC 10M; All Cells LCC, 4W-270) prepared in the culture medium to give $1\times10^6$ cells/mL was seeded in the 96 well plate under cultivation in an amount of 100 μL. The anti-TSPAN8(16B11)-anti-CD3 bispecific antibody prepared to give a final concentration of 0, 3, 30, 100, 300, 1000, 3000, or 10000 ng/mL was added thereto each in an amount of 50 μL, and a fluorescence (GFP) area in each well was measured 3 days later with IncuCyte(R) ZOOM (Sartorius) under cultivation at 37° C. in 5% $CO_2$. FIG. 9 shows a cell growth curve using the fluorescence area as an index of the cell growth. The ordinate of FIG. 9 indicates relative values of the fluorescence area of the 60As6-Luc/GFP cell when the fluorescence area of a well with only the medium is taken as 0%, and the fluorescence area of a well with no antibody solutions added is taken as 100%. As a result, the anti-TSPAN8(16B11)-anti-CD3 bispecific antibody exhibited a cell growth inhibitory effect in vitro against the 60As6-Luc/GFP cell which was a gastric cancer cell expressing TSPAN8.

Example 10: Evaluation of Drug Effect of Anti-TSPAN8/anti-CD3 Bispecific Antibody using Ascites Cell of Patient When the anti-TSPAN8-anti-CD3 bispecific antibody binds to a cancer cell and an immune cell contained in an ascites cell of a patient, the immune cell is activated, and the cancer cell is damaged. The cytotoxic activity against a cancer cell and the immune cell-activating action of the anti-TSPAN8(16B11)-anti-CD3 bispecific antibody were evaluated by the following method.

Figures 1, 10:
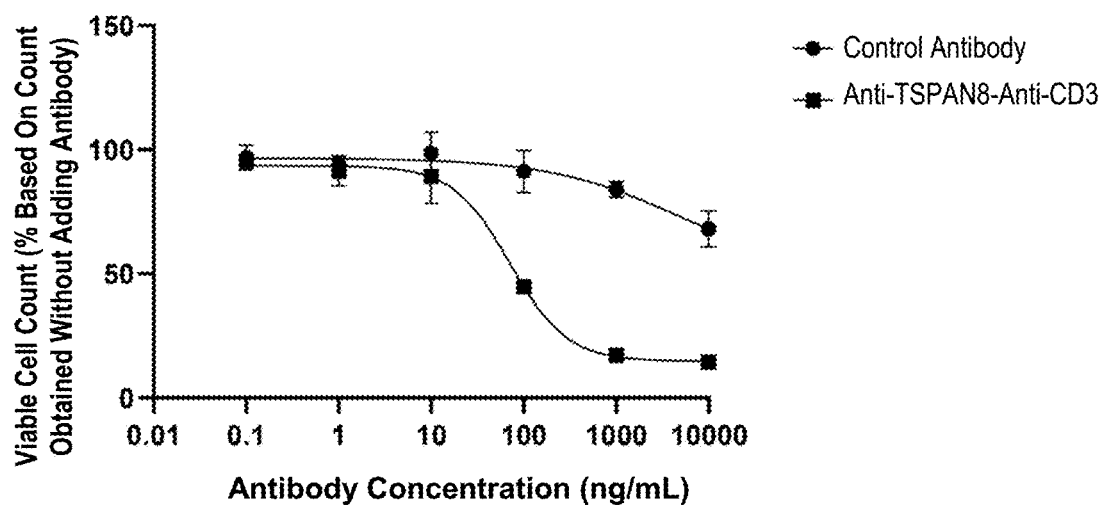
Figures 2, 10:
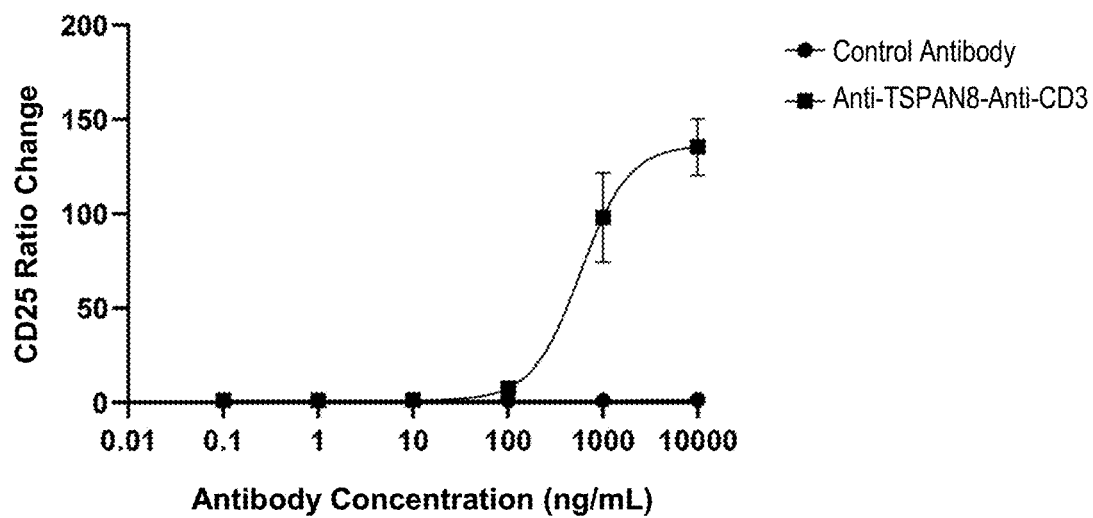
Figures 3, 10:
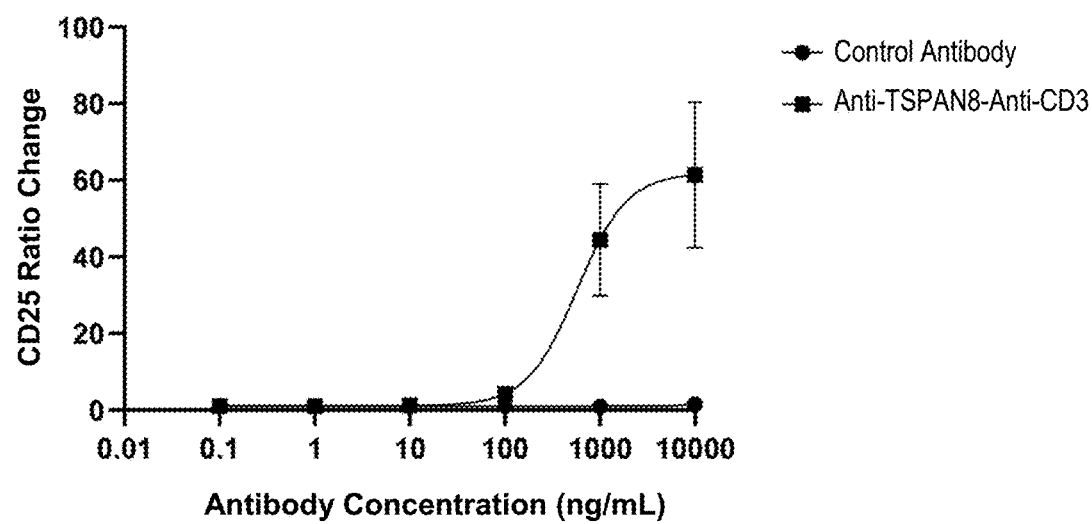

As an ascites cell of a patient, a cell obtained by subjecting the ascites fluid of a patient to the same treatment as in Example 1-1 until the hemolyzation and cryopreserving the resultant cell was used. The thawed cell was prepared in the same culture medium as in Example 9 to give $2\times10^6$ cells/mL, and the cell solution was seeded in a flat bottom 96 well plate at 100 μL/well. As test antibodies, an anti-TSPAN8(16B11)-anti-CD3 bispecific antibody and control antibodies (an anti-KLH antibody with the Fab of 16B11.1 replaced with the Fab of an anti-KLH (keyhole limpet hemocyanin) antibody and a bispecific antibody of an anti-CD3 antibody) were used. Each test antibody was diluted from 10 μg/mL to 0.1 ng/mL at a 10-fold common ratio. The test antibody was added to the 96 well plate with the cell seeded, followed by cultivation at 37° C. in a 5% $CO_2$ incubator. For the cultivation, a culture medium was used. The cell was collected 3 days later and seeded in a V-bottom microplate. In collecting, cells adhering to the plate were dissociated with Accutase (Innovative Cell Technologies, AT-104) and added to the V-bottom microplate. After centrifugation at 720×g for 2 minutes, supernatant was removed, and a solution prepared by adding a 40/1 amount of Human BD Fc Block (Beckton, Dickinson and Company, 564220) to staining buffer (10% FBS-containing PBS, 0.09% NaN3, 2 mM EDTA) was added at 20 μL/well. To each of the wells, FITC Mouse Anti-Human CD4 (Beckton, Dickinson and Company, 550628) diluted with staining buffer, APC-H7 Mouse anti-Human CD8 (Beckton, Dickinson and Company, 560179), APC Mouse Anti-Human CD45 (Beckton, Dickinson and Company, 555485), PE Mouse Anti-Human CD25 (Beckton, Dickinson and Company, 555432), and Brilliant Violet 421 anti-human CD326 (EpCAM) Antibody (BioLegend, 324200) were added in an amount of 10 μL/well, and the resultant was stand still at 4° C. for 50 minutes. After washing the cell once with staining buffer, the cell was suspended again in staining buffer containing 1/200 amount of 7-AAD solution, and the bindings of various antibodies to the ascites cell were measured by flow cytometry using CytoFLEX S (Beckman Coulter). The data was analyzed with FlowJo. A 7-AAD-negative cell fraction as an index of living cells was expanded with CD45 as an index of an immune cell and EpCAM as an index of a cancer cell. A CD45-negative EpCAM-positive cancer cell was expanded in Fsc (lin) and Ssc (lin), and the number of cells excluding a fragmented fraction were defined as a viable cell count of cancer cells. Further, expression of an activation marker CD25 on a CD4- or CD8-positive cell in a CD45-positive fraction was measured, and the MFI of anti-CD25-PE fluorescence intensity was calculated. FIG. 10-1 shows changes in viable cell count of cancer cells. The ordinate indicates relative values of the number of cancer cells when the number of cancer cells with no antibody solutions added is taken as 100%. FIGS. 10-2 and 10-3 each show changes in CD25 expression level on CD4-positive T cells and CD8-positive T cells due to the test antibodies. The ordinate indicates calculated relative values of the MFI of anti-CD25-PE fluorescence intensity.

As a result, it was observed that the viable cell count of cancer cells contained in the ascites fluid was reduced by adding the anti-TSPAN8(16B11)-anti-CD3 bispecific antibody as shown in FIG. 10-1, and that CD4-positive T cells and CD8-positive T cells in the ascites fluid were activated as shown in FIGS. 10-2 and 10-3. These results suggest that the anti-TSPAN8(16B11)-anti-CD3 bispecific antibody activates CD4-positive T cells and CD8-positive T cells in ascites fluids and kills cancer cells in ascites fluids.

Example 11: Evaluation of in vivo Anti-tumor Properties of Anti-TSPAN8/anti-CD3 Bispecific Antibody The in vivo anti-tumor actions by the anti-TSPAN8 (16B11)-anti-CD3 bispecific antibody were evaluated using a gastric cancer peritoneal dissemination model.

Example 11-1: Production of Expanded pan T cell

An anti-CD3 antibody (BioLegend, 317315) dissolved in PBS at 3 g/mL was added to a 24 well plate (IWAKI, 3820-024) in an amount of 250 µL for each, followed by standing still at 4° C. On the next day, the plate was washed with a culture medium twice, the culture medium was added thereto, followed by standing still at room temperature until the cell seeding described below. From HPBMC, human peripheral blood mononuclear cells, Cryopreserved (LONZA, CC-2702), pan T cells (including both CD4T cells and CD8T cells) were isolated. For the isolation, PanT Cell Isolation Kit, human (Miltenyi Biotec, 130-096-535) was used, and the experiment was performed in accordance with the protocol attached to the kit. After removing the culture medium from the 24 well plate, pan T cells prepared at $3\times10^6$ cells/mL was seeded in an amount of 500 µL for each. Besides, a culture medium containing 20 ng/mL of human IL-2 (PeproTech, 200-2) and 2 g/mL of anti-CD28 antibody (BioLegend, 302923) was added thereto in an amount of 500 µL for each, followed by cultivation in a 5% $CO_2$ incubator at 37° C. The cells were passaged into a new plate (IWAKI & CO., LTD.,3810-006) 3 days, 5 days and 7 days after the start of the cultivation, and IL-2 was added thereto to give a final concentration of 10 ng/mL. 7 days and 10 days after the start of the cultivation, the cells were collected and used in Example 10-2. The cells isolated and grown here were designated as Expanded pan T cells.

Example 11-2: Confirmation of Medical Effect in Gastric Cancer Peritoneal Dissemination Model The 60As6-Luc/GFP cell was transplanted at $1\times10^6$ cells/1 mL/PBS into the abdominal cavity of 7-week old C.B17/Icr-scid/scidJcl female mice (CLEA Japan, Inc.) grouped by seven mice in each group. 6 days after the transplantation, the mice were grouped using the amount of luminescence of the substrate Luciferin by Luciferase introduced into the 60As6-Luc/GFP cell as an index so that each group was even. The amount of luminescence of Luciferin was used as an index indicating the tumor volume.

Figures 1, 11:
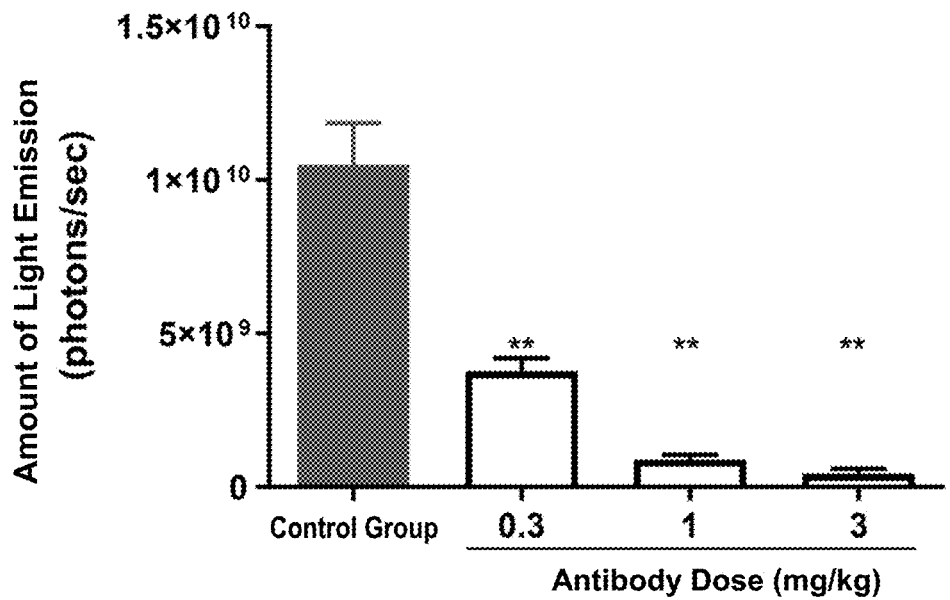
Figures 2, 11:
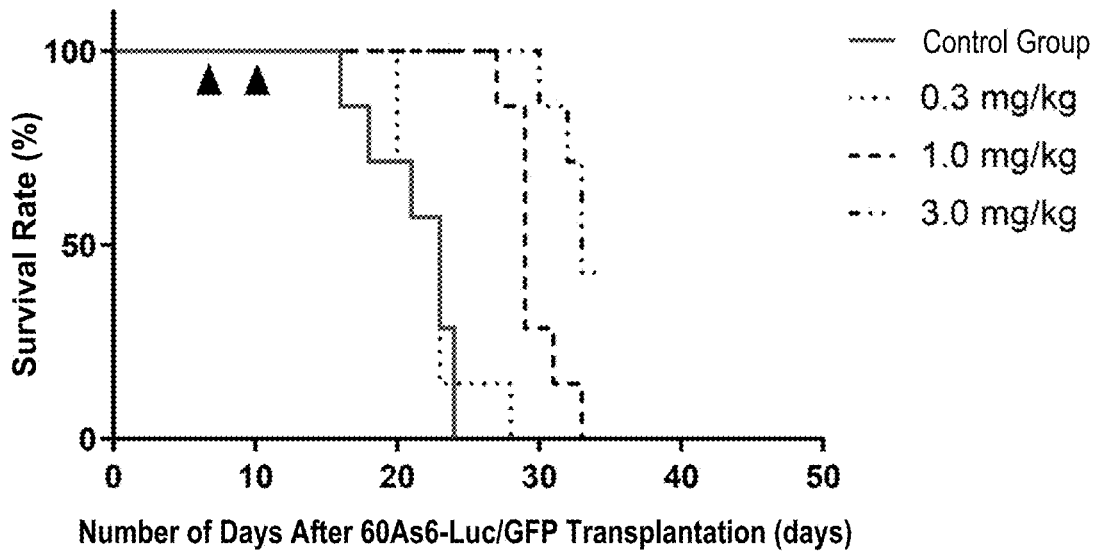

Specifically, a solution obtained by dissolving 3 mg of Luciferin (VivoGlo Luciferin, In Vivo Grade, Promega, P1043) in 0.5 mL of PBS was intraperitoneally administered to each mouse, and the amount of light emission was measured 10 minutes after the administration with IVIS Lumina II (Perkin Elmer). Next, a solution obtained by suspending 1×10' expanded pan T cells in 0.5 mL of PBS and a solution obtained by suspending 0, 0.3, 1.0, or 3.0 mg/kg of the anti-TSPAN8(16B11)-anti-CD3 bispecific antibody in 0.2 mL of PBS were intraperitoneally administered 7 days and 10 days after the transplantation of the 60As6-Luc/GFP cell. The amount of luminescence of Luciferin was measured 14 days after the transplantation of the gastric cancer cell, to evaluate the increase or decrease in tumor volume. Besides, survival of the peritoneal dissemination mouse model was observed until 34 days after the transplantation of the 60As6-Luc/GFP cell. As shown in FIG. 11-1, a significant action of tumor volume reduction was exhibited in the anti-TSPAN8(16B11)-anti-CD3 bispecific antibody administration group, and as shown in FIG. 11-2, a significant effect of lifetime elongation was exhibited in groups administered with 1.0 or 3.0 mg/kg of the antibody. Table 4 shows mean survival times and test results. A significance probability, p-value, shown in the table was obtained by comparing a lifetime of a control group (group administered with a solvent) with a lifetime of the anti-TSPAN8(16B11)-anti-CD3 bispecific antibody administration group by the log-rank test. In the table, ** indicates a group having a p-value smaller than a significance level of 0.01/3 corrected by the Bonferroni method.

TABLE 4

| Treatment | | Median survival | Significant difference | P value |
|---|---|---|---|---|
| Control group | PBS | 23 | — | — |
| Anti-TSPAN8(16B11)- | 0.3 mg/kg | 23 | ns | |
| anti-CD3 | 1.0 mg/kg | 29 | ** | 0.0006 |
| bispecific antibody | 3.0 mg/kg | 33 | ** | 0.0006 |

Log-rank (Mantel-Cox) test (Bonferroni correction)

Figure 12:
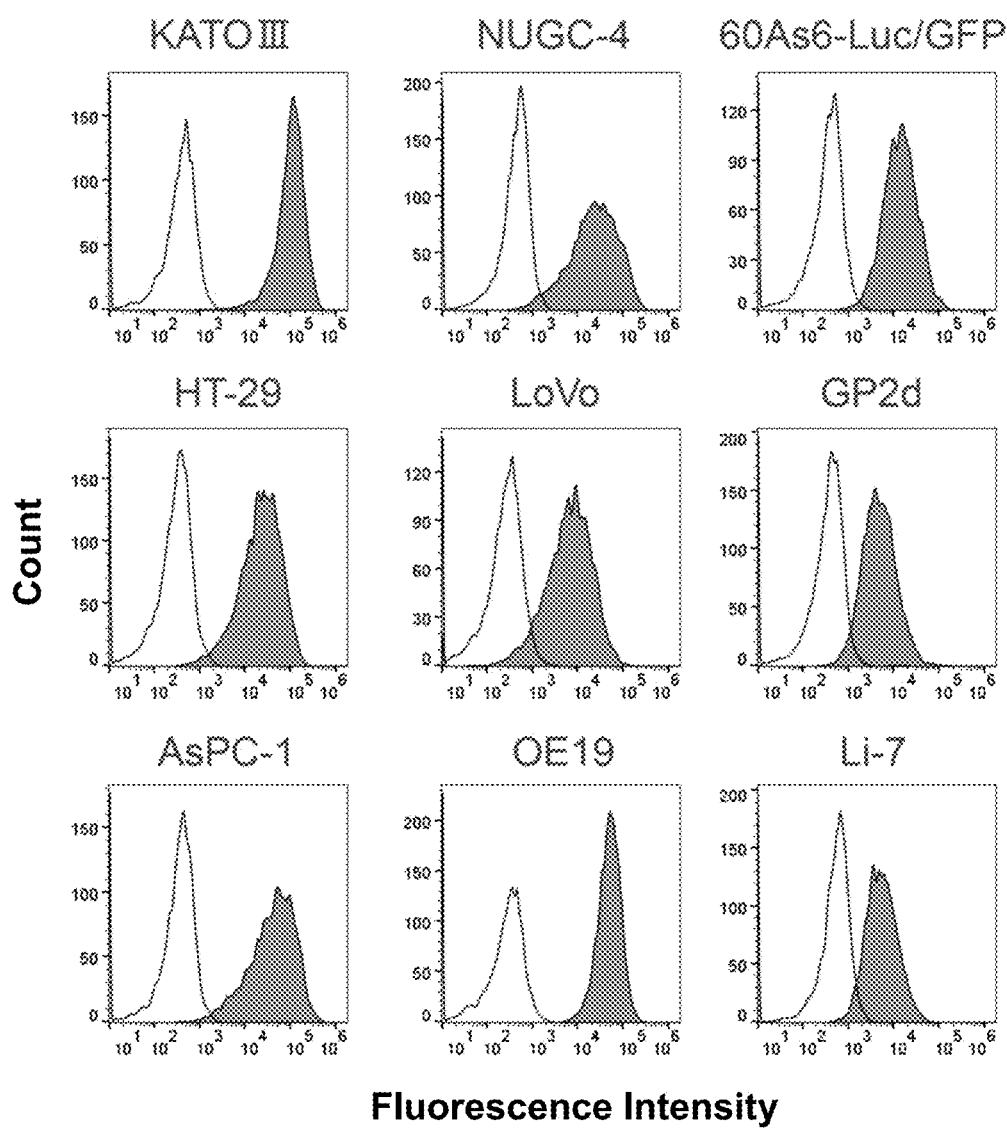
FIG. 12 illustrates results of measurement with flow cytometry of a binding of 16B11 to various cancer cell lines. The abscissa of the drawing indicates fluorescence intensity, and the ordinate indicates the cell count. In the drawing, a white area indicates the binding of a negative control antibody, and a dark gray area indicates the binding of 16B11.

Example 12: Action of Anti-TSPAN8-Anti-CD3 Bispecific Antibody on Various Cancer Cell Lines Example 12-1: Check of Binding Activity of Anti-TSPAN8 Antibody to Various Cancer Cell Lines The bindings of Alexa Fluor647 labeled 16B11 to gastric carcinoma cell lines (KATOIII cell: Japanese Collection of Research Bioresources (JCRB), JCRB0611, NUGC-4 cell: RIKEN BioResource Research Center(BRC), RCB1939, and 60As6-Luc/GFP cell), colon carcinoma cell lines (HT-29 cell: ATCC, HTB-38, LoVo cell: ATCC, CCL-229, and GP2d cell: The European Collection of Authenticated Cell Cultures (ECACC), 95090714), a pancreatic carcinoma cell line (AsPC-1 cell: ATCC, CRL-1682), an esophageal carcinoma cell line (0E19 cell: ECACC, 96071721), and a liver cancer cell line (Li-7 cell: RIKEN BRC, RCB1941) were measured by flow cytometry. As a negative control antibody, an in-house anti-KLH antibody (173A1) labeled with Alexa Fluor647 was used. FIG. 12 shows the histograms of the bindings of 16B11 and the negative control antibody to various carcinoma cell lines.

Figures 1, 13:
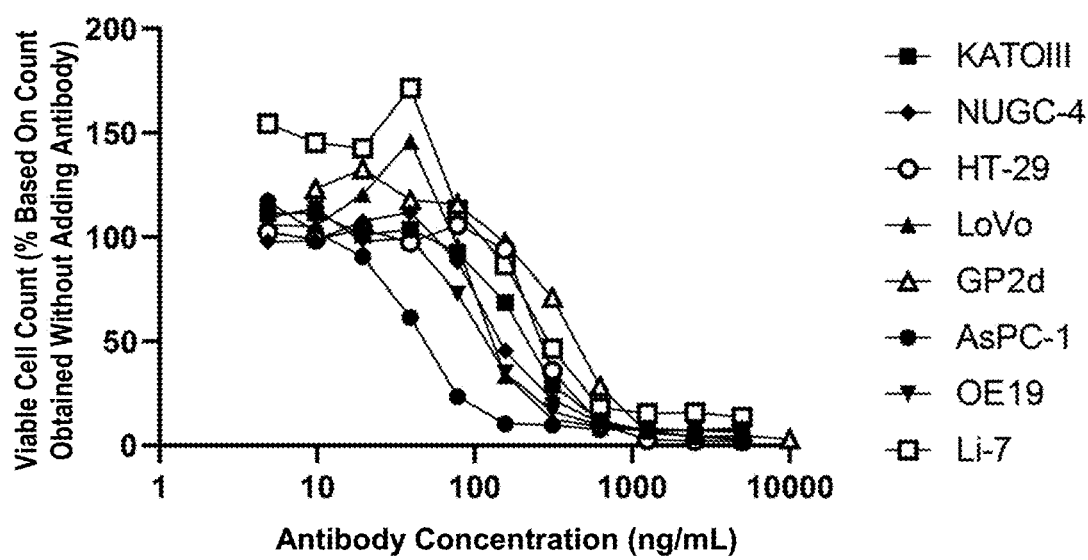
Figures 2, 13:
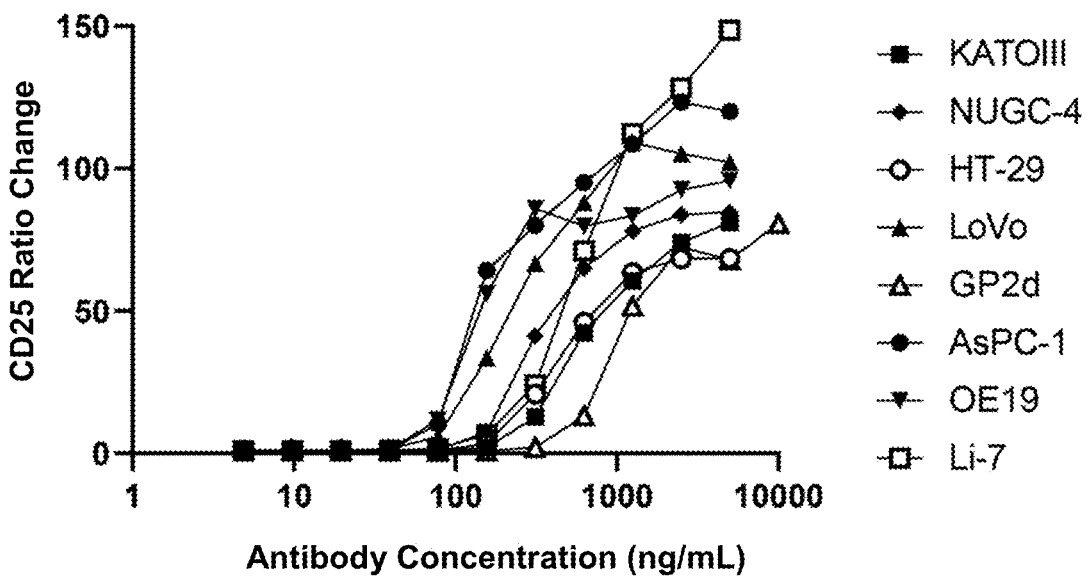
Figures 3, 13:
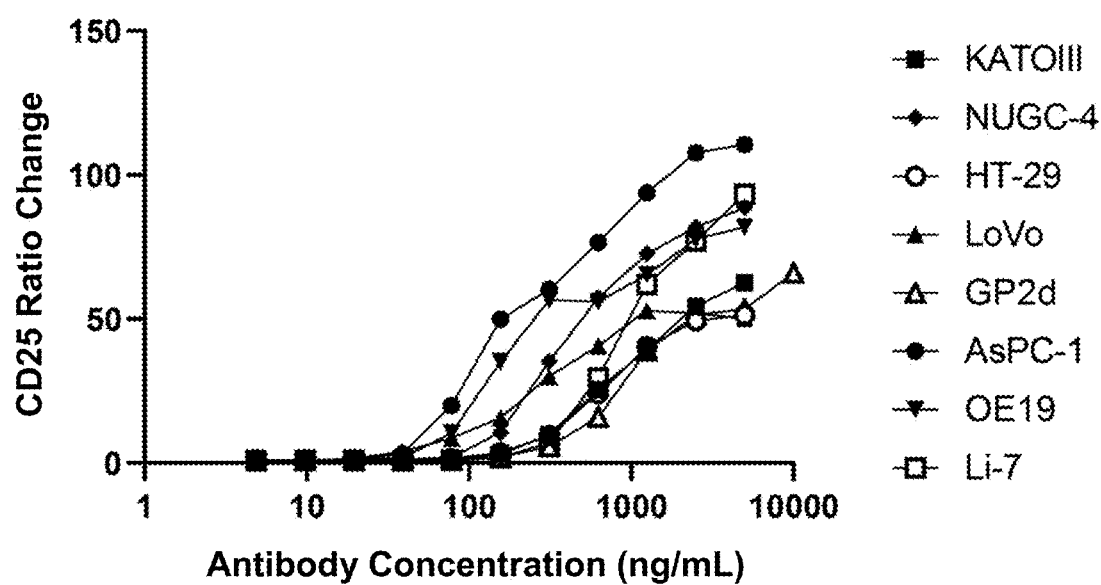

Example 12-2: Evaluation of RTCC Activity of Anti-TSPAN8/anti-CD3 Bispecific Antibody on Various Carcinoma Cell Lines The KATOIII cell, the NUGC-4 cell, the HT-29 cell, the LoVo cell, the GP2d cell, the AsPC-1 cell, the 0E19 cell, and the Li-7 cell were prepared in a culture medium to give $2 \times 10^5$ cells/mL and seeded in a flat bottom 96 well plate (IWAKI & CO., LTD., 3860-096) in an amount of 50 μL for each, followed by cultivation in a 5% $CO_2$ incubator at 37° C. A cryopreserved human peripheral blood mononuclear cell (Lonza Group AG, CC-2702) prepared in the culture medium to give $1 \times 10^6$ cells/mL was seeded in the 96 well plate under the cultivation in an amount of 100 μL for each. The anti-TSPAN8(16B11)-anti-CD3 bispecific antibody was diluted with a culture medium at a double common ratio with a maximum concentration of 40 μg/mL or 20 μg/mL. The anti-TSPAN8(16B11)-anti-CD3 bispecific antibody diluted was added in an amount of 50 μL (with a maximum final concentration of 10 μg/mL or 5 μg/mL). The resultant in the 96 well plate with each carcinoma cell line, the cryopreserved human peripheral blood mononuclear cell and the antibody added was cultured in a 5% $CO_2$ incubator at 37° C. The cells were collected 3 days later and seeded in a V-bottom microplate. In collecting, cells adhering to the culture plate were dissociated with Accutase (Innovative Cell Technologies, AT-104) and added to the V-bottom microplate. After centrifugation at 720×g for 2 minutes, supernatant was removed, and a liquid obtained by adding a 1/40 amount of Human BD Fc Block to staining buffer was added at 20 μL/well. APC Mouse Anti-Human CD4 (Becton, Dickinson and Company, 555349), APC-H7 Mouse anti-Human CD8, Brilliant Violet 421 Mouse Anti-Human CD45 (Becton, Dickinson and Company, 563879), and PE Mouse Anti-Human CD25 diluted with staining buffer each were added to a well at 10 μL/well, followed by standing at 4° C. for 1 hour. After washing once with staining buffer, a 1/200 amount of 7-AAD solution was added thereto. The resultant was suspended again in the staining buffer, and the bindings of various antibodies were measured by flow cytometry using CytoFLEX S. The data was analyzed with FlowJo. The number of CD45-negative cells in the 7-AAD-negative cell fraction as an index of living cells was taken as the viable cell count of carcinoma cells. Those with no antibody solutions added were taken as 100%. Besides, fold changes in expression of an activation marker CD25 in CD4-or CD8-positive cells of a CD45-positive fraction when the MFI of anti-CD25-PE fluorescence intensity with no antibody solutions added was taken as 1 were calculated for each. As a result, the viable cell count of TSPAN8-expressing carcinoma cells was reduced due to the addition of the anti-TSPAN8(16B11)-anti-CD3 bispecific antibody, as shown in FIG. 13-1. Further, activations of CD4-positive T cells and CD8-positive T cells were observed, as shown respectively in FIG. 13-2 and FIG. 13-3.

Figures 1, 14:
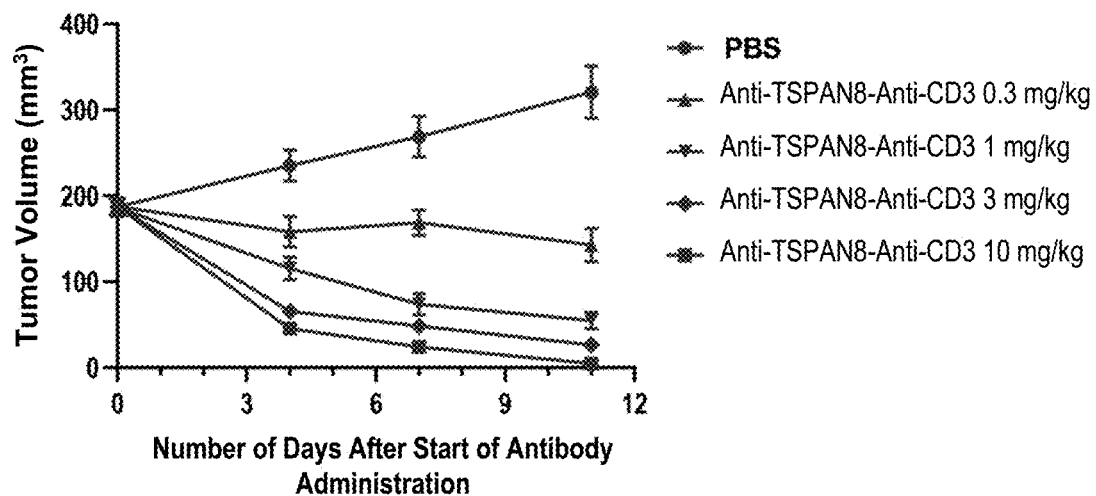
FIG. 14 illustrates an anti-tumor effect of the anti-TSPAN8(16B11)-anti-CD3 bispecific antibody in a human PBMC-transferred HT-29 cell subcutaneous cancer-bearing model.
Figures 2, 14:
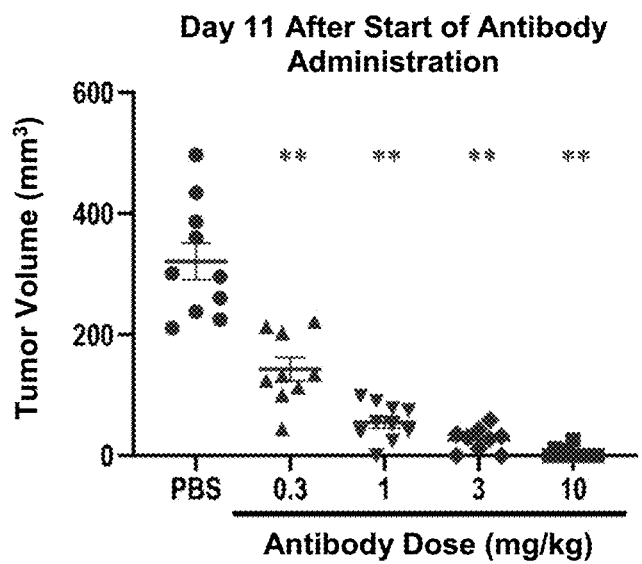

Example 12-3: Confirmation of Medical Effect in Human PBMC-Engrafted HT-29 Cell Subcutaneous Tumor-Bearing Model Normal human PBMC (Precision for Medicine, 33000-10M) was suspended in PBS to give $1.25 \times 10^7$ cells/mL, and the cells were injected into the tail vein of 6 week-old NOD/Shi-scid, IL-2RγKO(NOG) female mice (In-Vivo Science Inc.) at $2.5 \times 10^6$ cells/200 μL. 10 days after the transfer of human PBMC, HT-29 cells were suspended in PBS to give $5 \times 10^7$ cells/mL, and were inoculated subcutaneously in the mice at $5 \times 10^6$ cells/100 μL. 10 days after the inoculation of the HT-29 cells, the tumor volume was measured using a slide caliper, and the mice were allocated with similar mean tumor volumes between (n=10). Administration of the anti-TSPAN8(16B11)-anti-CD3 bispecific antibody was started from the same day. The first day of administration was defined as day 0. PBS or 0.3, 1, 3, or 10 mg/kg of the anti-TSPAN8(16B11)-anti-CD3 bispecific antibody was intravenously administered to the mice on day 0, 4, and 7. The tumor volume was measured on day 0, 4, 7, and 11 (FIG. 14-1). The tumor volume [mm³] was calculated by the following formula.

$$(\text{Length of tumor major axis [mm]}) \times (\text{Length of tumor minor axis [mm]})^2 \times 0.5$$

As shown in FIG. 14-2, the anti-TSPAN8(16B11)-anti-CD3 bispecific antibody significantly suppressed the growth of the HT-29 tumor at 0.3, 1, 3, and 10 mg/kg.

INDUSTRIAL APPLICABILITY

The anti-TSPAN8 antibody of the present invention and the fusion of the anti-TSPAN8 antibody such as an anti-TSPAN8-anti-CD3 bispecific antibody are expected to be useful for treating cancer. Besides, the polynucleotide, the expression vector, the transformed host cell, and the method for producing an antibody of the present invention are useful for producing the anti-TSPAN8 antibody and the fusion thereof Sequence Listing Free Text In number heading <223> of the following sequence listing, "Artificial Sequence" is described. Specifically, SEQ ID NO: 2 represents the amino acid sequence of human TSPAN8-Myc-DDK, and the nucleotide sequence represented by SEQ ID NO: 1 is a nucleotide sequence encoding the amino acid sequence of human TSPAN8 represented by SEQ ID NO: 2. SEQ ID NO: 4, 6, or 10 is the amino acid sequence of the heavy chain of the anti-TSPAN8 antibody, and the nucleotide sequence represented by SEQ ID NO: 3, 5, or 9 is a nucleotide sequence encoding the amino acid sequence of the heavy chain of the anti-TSPAN8 antibody represented by SEQ ID NO: 4, 6, or 10. The sequence of SEQ ID NO: 8 or 12 is the amino acid sequence of the light chain of the anti-TSPAN8 antibody, and the nucleotide sequence represented by SEQ ID NO: 7 or 11 is a nucleotide sequence encoding the amino acid sequence of the light chain of the anti-TSPAN8 antibody represented by SEQ ID NO: 8 or 12. SEQ ID NO: 14 is an amino acid sequence of a polypeptide in which the anti-CD3-scFv region and the second Fc polypeptide are linked together, and the nucleotide sequence represented by SEQ ID NO: 13 is a nucleotide sequence encoding the amino acid sequence of the polypeptide, represented by SEQ ID NO: 14, in which the anti-CD3-scFv region and the second Fc polypeptide are linked together. SEQ ID NOs: 15 to 23 represent the amino acid sequences of the various linkers described in the detailed description of the present invention. SEQ ID NOs: 24 to 37 are amino acid sequences of CDRs and variable regions of 16B11 and 16B12. SEQ ID NOs: 38 to 40 are amino acid sequences of signal sequences. SEQ ID NOs: 41 to 43 are respectively the amino acid sequences of the region at amino acid positions 126 to 155 of mouse, rat or cynomolgus monkey TSPAN8.

Sequence Listing

The invention claimed is:

1. A bispecific antibody that binds to TSPAN8 and CD3, comprising:
   (a) a Fab region of an anti-TSPAN8 antibody consisting of: a heavy chain fragment comprising a heavy chain variable region of the anti-TSPAN8 antibody; and a light chain comprising a light chain variable region of the anti-TSPAN8 antibody;
   (b) an anti-CD3-scFv region comprising a heavy chain variable region and a light chain variable region of an anti-CD3 antibody; and
   (c) a Fc region consisting of a first Fc polypeptide linked to the heavy chain fragment of the Fab region (a) and a second Fc polypeptide linked to the anti-CD3-scFv region (b),
   wherein
   the heavy chain variable region of the anti-TSPAN8 antibody comprises a CDR1 consisting amino acids 31 to 35 of SEQ ID NO: 6, a CDR2 consisting of amino acids 50 to 66 of SEQ ID NO: 6, and a CDR3 consisting of amino acids 99 to 110 of SEQ ID NO: 6, and the light chain variable region of the anti-TSPAN8 antibody comprises a CDR1 consisting of amino acids 24 to 34 of SEQ ID NO: 8, a CDR2 consisting of amino acids 50 to 56 of SEQ ID NO: 8, and a CDR3 consisting of amino acids 89 to 96 of SEQ ID NO: 8; or
   the heavy chain variable region of the anti-TSPAN8 antibody comprises a CDR1 consisting of amino acids 31 to 35 of SEQ ID NO: 10, a CDR2 consisting of amino acids 50 to 66 of SEQ ID NO: 10, and a CDR3 consisting of amino acids 99 to 110 of SEQ ID NO: 10, and the light chain variable region of the anti-TSPAN8 antibody comprises a CDR1 consisting of amino acids 24 to 34 of SEQ ID NO: 12, a CDR2 consisting of amino acids 50 to 56 of SEQ ID NO: 12, and a CDR3 consisting of amino acids 89 to 96 of SEQ ID NO: 12.

2. The bispecific antibody according to claim 1, wherein the heavy chain variable region of the anti-TSPAN8 antibody comprises a CDR1 consisting amino acids 31 to 35 of SEQ ID NO: 6, a CDR2 consisting of amino acids 50 to 66 of SEQ ID NO: 6, and a CDR3 consisting of amino acids 99 to 110 of SEQ ID NO: 6, and the light chain variable region of the anti-TSPAN8 antibody comprises a CDR1 consisting of amino acids 24 to 34 of SEQ ID NO: 8, a CDR2 consisting of amino acids 50 to 56 of SEQ ID NO: 8, and a CDR3 consisting of amino acids 89 to 96 of SEQ ID NO: 8.

3. The bispecific antibody according to claim 1, wherein the heavy chain variable region of the anti-TSPAN8 antibody comprises a CDR1 consisting of amino acids 31 to 35 of SEQ ID NO: 10, a CDR2 consisting of amino acids 50 to 66 of SEQ ID NO: 10, and a CDR3 consisting of amino acids 99 to 110 of SEQ ID NO: 10, and the light chain variable region of the anti-TSPAN8 antibody comprises a CDR1 consisting of amino acids 24 to 34 of SEQ ID NO: 12, a CDR2 consisting of amino acids 50 to 56 of SEQ ID NO: 12, and a CDR3 consisting of amino acids 89 to 96 of SEQ ID NO: 12.

4. The bispecific antibody according to claim 1, wherein the heavy chain variable region of the anti-TSPAN8 antibody consists of amino acids 1 to 121 of SEQ ID NO: 6, and the light chain variable region of the anti-TSPAN8 antibody consists of amino acids 1 to 107 of SEQ ID NO: 8.

5. The bispecific antibody according to claim 1, wherein the heavy chain variable region of the anti-TSPAN8 antibody consists of amino acids 1 to 121 of SEQ ID NO: 10, and the light chain variable region of the anti-TSPAN8 antibody consists of amino acids 1 to 107 of SEQ ID NO: 12.

6. The bispecific antibody according to claim 1, wherein the Fab region of the anti-TSPAN8 antibody consists of a heavy chain fragment consisting of amino acids 1 to 219 of SEQ ID NO: 6 and a light chain consisting of an amino acid sequence of SEQ ID NO: 8.

7. The bispecific antibody according to claim 1, wherein the Fab region of the anti-TSPAN8 antibody consists of a heavy chain fragment consisting of an amino acid sequence from amino acid positions 1 to 219 of SEQ ID NO: 10 and a light chain consisting of an amino acid sequence of SEQ ID NO: 12.

8. The bispecific antibody according to claim 1, wherein the heavy chain variable region of the anti-CD3 antibody comprises a CDR1 consisting of amino acids 31 to 35 of SEQ ID NO: 14, a CDR2 consisting of amino acids 50 to 68 of SEQ ID NO: 14, and a CDR3 consisting of amino acids 101 to 114 of SEQ ID NO: 14, and the light chain variable region of the anti-CD3 antibody comprises a CDR1 consisting of amino acids 168 to 181 of SEQ ID NO: 14, a CDR2 consisting of amino acids 197 to 203 of SEQ ID NO: 14, and a CDR3 consisting of amino acids 236 to 244 of SEQ ID NO: 14.

9. The bispecific antibody according to claim 2, wherein the heavy chain variable region of the anti-CD3 antibody comprises a CDR1 consisting of amino acids 31 to 35 of SEQ ID NO: 14, a CDR2 consisting of amino acids 50 to 68 of SEQ ID NO: 14, and a CDR3 consisting of amino acids 101 to 114 of SEQ ID NO: 14, and the light chain variable region of the anti-CD3 antibody comprises a CDR1 consisting of amino acids 168 to 181 of SEQ ID NO: 14, a CDR2 consisting of amino acids 197 to 203 of SEQ ID NO: 14, and a CDR3 consisting of amino acids 236 to 244 of SEQ ID NO: 14.

10. The bispecific antibody according to claim 3, wherein the heavy chain variable region of the anti-CD3 antibody comprises a CDR1 consisting of amino acids 31 to 35 of SEQ ID NO: 14, a CDR2 consisting of amino acids 50 to 68 of SEQ ID NO: 14, and a CDR3 consisting of amino acids 101 to 114 of SEQ ID NO: 14, and the light chain variable region of the anti-CD3 antibody comprises a CDR1 consisting of amino acids 168 to 181 of SEQ ID NO: 14, a CDR2 consisting of amino acids 197 to 203 of SEQ ID NO: 14, and a CDR3 consisting of amino acids 236 to 244 of SEQ ID NO: 14.

11. The bispecific antibody according to claim 1, wherein the heavy chain variable region of the anti-CD3 antibody consists of amino acids 1 to 125 of SEQ ID NO: 14, and the light chain variable region of the anti-CD3 antibody consists of amino acids 146 to 254 of SEQ ID NO: 14.

12. The bispecific antibody according to claim 4, wherein the heavy chain variable region of the anti-CD3 antibody consists of amino acids 1 to 125 of SEQ ID NO: 14, and the light chain variable region of the anti-CD3 antibody consists of amino acids 146 to 254 of SEQ ID NO: 14.

13. The bispecific antibody according to claim 5, wherein the heavy chain variable region of the anti-CD3 antibody consists of amino acids 1 to 125 of SEQ ID NO: 14, and the light chain variable region of the anti-CD3 antibody consists of amino acids 146 to 254 of SEQ ID NO: 14.

14. The bispecific antibody according to claim 1, wherein the anti-CD3-scFv region consists of amino acids 1 to 254 of SEQ ID NO: 14.

15. The bispecific antibody according to claim 1, wherein the Fc region comprises a LALA mutation, a N297G mutation, and a knobs-into-holes mutation, wherein the knobs-into-holes mutation is T366W mutation in one Fc polypeptide included in the Fc region, and T366S, L368A and Y407V mutation in another Fc polypeptide included in the Fc region, wherein positions of mutation are amino acid positions in human Igyl constant region according to EU index.

16. The bispecific antibody according to claim 1, wherein the first Fc polypeptide consists of amino acids 235 to 451 of SEQ ID NO: 6 and the second Fc polypeptide consists of amino acids 270 to 486 of SEQ ID NO: 14.

17. The bispecific antibody according to claim 1, wherein the heavy chain fragment of the anti-TSPAN8 antibody and the first Fc polypeptide are linked through a hinge region, and the anti-CD3-scFv region and the second Fc polypeptide are linked through a hinge region.

18. The bispecific antibody according to claim 1 further comprising a post-translational modification selected from pyroglutamylation at a N-terminal of the heavy chain variable region of the anti-TSPAN8 antibody or the anti-CD3-scFv, a lysine deletion at a C-terminal of a heavy chain variable region of the anti-TSPAN8 antibody or the anti-CD3-scFv, or a combination thereof.

19. A bispecific antibody that binds to TSPAN8 and CD3, comprising:
(a) a Fab region of an anti-TSPAN8 antibody consisting of: a heavy chain fragment comprising a heavy chain variable region of the anti-TSPAN8 antibody; and a light chain comprising a light chain variable region of the anti-TSPAN8 antibody;
(b) an anti-CD3-scFv region comprising a heavy chain variable region and a light chain variable region of an anti-CD3 antibody; and
(c) a Fc region consisting of a first Fc polypeptide linked to the heavy chain fragment of the Fab region (a) and a second Fc polypeptide linked to the anti-CD3-scFv region (b),
wherein the bispecific antibody comprises: a heavy chain of the anti-TSPAN8 antibody consisting of an amino acid sequence of SEQ ID NO: 6 in which the heavy chain fragment of the anti-TSPAN8 antibody is linked to the first Fc polypeptide; a light chain of the anti-TSPAN8 antibody consisting of an amino acid sequence of SEQ ID NO: 8; and a polypeptide consisting of an amino acid sequence of SEQ ID NO: 14 in which the anti-CD3-scFv region is linked to the second Fc polypeptide.

20. A method of treating cancer, comprising administering to a subject with cancer a bispecific antibody according to claim 1.

* * * * *

SEQUENCE LISTING

<160> NUMBER OF SEQ ID NOS: 43

<210> SEQ ID NO 1
<211> LENGTH: 807
<212> TYPE: DNA
<213> ORGANISM: Artificial Sequence
<220> FEATURE:
<223> OTHER INFORMATION: human TSPAN8-Myc-DDK
<220> FEATURE:
<221> NAME/KEY: CDS
<222> LOCATION: (1)..(807)

<400> SEQUENCE: 1

```
atg gca ggt gtg agt gcc tgt ata aaa tat tct atg ttt acc ttc aac      48
Met Ala Gly Val Ser Ala Cys Ile Lys Tyr Ser Met Phe Thr Phe Asn
1               5                   10                  15 ttc ttg ttc tgg cta tgt ggt atc ttg atc cta gca tta gca ata tgg      96
Phe Leu Phe Trp Leu Cys Gly Ile Leu Ile Leu Ala Leu Ala Ile Trp
                20                  25                  30 gta cga ata agc aat gac tct caa gca att ttt ggt tct gaa gat gta     144
Val Arg Ile Ser Asn Asp Ser Gln Ala Ile Phe Gly Ser Glu Asp Val
            35                  40                  45 ggc tct agc tcc tac gtt gct gtg gac ata ttg att gct gta ggt gcc     192
Gly Ser Ser Ser Tyr Val Ala Val Asp Ile Leu Ile Ala Val Gly Ala
        50                  55                  60 atc atc atg att ctg ggc ttc ctg gca tgc tgc ggt gct ata aaa gaa     240
Ile Ile Met Ile Leu Gly Phe Leu Ala Cys Cys Gly Ala Ile Lys Glu
65                  70                  75                  80 agt cgc tgc atg ctt ctg ttg ttt ttc ata ggc ttg ctt ctg atc ctg     288
Ser Arg Cys Met Leu Leu Leu Phe Phe Ile Gly Leu Leu Leu Ile Leu
                85                  90                  95 ctc ctg cag gtg gcg aca ggt atc cta gga gct gtt ttc aaa tct aag     336
Leu Leu Gln Val Ala Thr Gly Ile Leu Gly Ala Val Phe Lys Ser Lys
            100                 105                 110 tct gat cgc att gtg aat gaa act ctc tat gaa aac aca aag ctt ttg     384
Ser Asp Arg Ile Val Asn Glu Thr Leu Tyr Glu Asn Thr Lys Leu Leu
        115                 120                 125 agc gcc aca ggg gaa agt gaa aaa caa ttc cag gaa gcc ata att gtg     432
Ser Ala Thr Gly Glu Ser Glu Lys Gln Phe Gln Glu Ala Ile Ile Val
    130                 135                 140 ttt caa gaa gag ttt aaa tgc tgc ggt ttg gtc aat gga gct gct gat     480
Phe Gln Glu Glu Phe Lys Cys Cys Gly Leu Val Asn Gly Ala Ala Asp
145                 150                 155                 160 tgg gga aat aat ttt caa cac tat cct gaa tta tgt gcc tgt cta gat     528
Trp Gly Asn Asn Phe Gln His Tyr Pro Glu Leu Cys Ala Cys Leu Asp
                165                 170                 175 aag cag aga cca tgc caa agc tat aat gga aaa caa gtt tac aaa gag     576
Lys Gln Arg Pro Cys Gln Ser Tyr Asn Gly Lys Gln Val Tyr Lys Glu
            180                 185                 190 acc tgt att tct ttc ata aaa gac ttc ttg gca aaa aat ttg att ata     624
Thr Cys Ile Ser Phe Ile Lys Asp Phe Leu Ala Lys Asn Leu Ile Ile
        195                 200                 205 gtt att gga ata gca ttt gga ctg gca gtt att gag ata ctg ggt ttg     672
Val Ile Gly Ile Ala Phe Gly Leu Ala Val Ile Glu Ile Leu Gly Leu
    210                 215                 220 gtg ttt tct atg gtc ctg tat tgc cag atc ggg aac aaa acg cgt acg     720
Val Phe Ser Met Val Leu Tyr Cys Gln Ile Gly Asn Lys Thr Arg Thr
225                 230                 235                 240 cgg ccg ctc gag cag aaa ctc atc tca gaa gag gat ctg gca gca aat     768
Arg Pro Leu Glu Gln Lys Leu Ile Ser Glu Glu Asp Leu Ala Ala Asn
```

```
            245                 250                 255
gat atc ctg gat tac aag gat gac gac gat aag gtt taa               807
Asp Ile Leu Asp Tyr Lys Asp Asp Asp Asp Lys Val
            260                 265
```

<210> SEQ ID NO 2
<211> LENGTH: 268
<212> TYPE: PRT
<213> ORGANISM: Artificial Sequence
<220> FEATURE:
<223> OTHER INFORMATION: Synthetic Construct

<400> SEQUENCE: 2

```
Met Ala Gly Val Ser Ala Cys Ile Lys Tyr Ser Met Phe Thr Phe Asn
1               5                   10                  15

Phe Leu Phe Trp Leu Cys Gly Ile Leu Ile Leu Ala Leu Ala Ile Trp
            20                  25                  30

Val Arg Ile Ser Asn Asp Ser Gln Ala Ile Phe Gly Ser Glu Asp Val
            35                  40                  45

Gly Ser Ser Tyr Val Ala Val Asp Ile Leu Ile Ala Val Gly Ala
    50                  55                  60

Ile Ile Met Ile Leu Gly Phe Leu Ala Cys Cys Gly Ala Ile Lys Glu
65                  70                  75                  80

Ser Arg Cys Met Leu Leu Leu Phe Phe Ile Gly Leu Leu Ile Leu
                85                  90                  95

Leu Leu Gln Val Ala Thr Gly Ile Leu Gly Ala Val Phe Lys Ser Lys
            100                 105                 110

Ser Asp Arg Ile Val Asn Glu Thr Leu Tyr Glu Asn Thr Lys Leu Leu
            115                 120                 125

Ser Ala Thr Gly Glu Ser Glu Lys Gln Phe Gln Glu Ala Ile Ile Val
            130                 135                 140

Phe Gln Glu Glu Phe Lys Cys Cys Gly Leu Val Asn Gly Ala Ala Asp
145                 150                 155                 160

Trp Gly Asn Asn Phe Gln His Tyr Pro Glu Leu Cys Ala Cys Leu Asp
                165                 170                 175

Lys Gln Arg Pro Cys Gln Ser Tyr Asn Gly Lys Gln Val Tyr Lys Glu
            180                 185                 190

Thr Cys Ile Ser Phe Ile Lys Asp Phe Leu Ala Lys Asn Leu Ile Ile
            195                 200                 205

Val Ile Gly Ile Ala Phe Gly Leu Ala Val Ile Glu Ile Leu Gly Leu
            210                 215                 220

Val Phe Ser Met Val Leu Tyr Cys Gln Ile Gly Asn Lys Thr Arg Thr
225                 230                 235                 240

Arg Pro Leu Glu Gln Lys Leu Ile Ser Glu Glu Asp Leu Ala Ala Asn
                245                 250                 255

Asp Ile Leu Asp Tyr Lys Asp Asp Asp Asp Lys Val
            260                 265
```

<210> SEQ ID NO 3
<211> LENGTH: 1356
<212> TYPE: DNA
<213> ORGANISM: Artificial Sequence
<220> FEATURE:
<223> OTHER INFORMATION: 16B11.1_HC
<220> FEATURE:
<221> NAME/KEY: CDS
<222> LOCATION: (1)..(1356)

<400> SEQUENCE: 3

| | | |
|---|---|---|
| cag gtt cag ctg gtt gaa tct ggc ggc gga gtt gtt cag cct ggc gga<br>Gln Val Gln Leu Val Glu Ser Gly Gly Gly Val Val Gln Pro Gly Gly<br>1               5                   10                  15 | | 48 |
| tct ctg aga ctg tct tgt gcc gcc tcc ggc ttc acc ttc tcc tct tac<br>Ser Leu Arg Leu Ser Cys Ala Ala Ser Gly Phe Thr Phe Ser Ser Tyr<br>            20                  25                  30 | | 96 |
| gga atg cac tgg gtc cga cag gcc cct ggc aaa gga ttg gaa tgg gtc<br>Gly Met His Trp Val Arg Gln Ala Pro Gly Lys Gly Leu Glu Trp Val<br>        35                  40                  45 | | 144 |
| gcc gtg att tgg tac gac ggc cgg aac aag tac tac gcc gac tcc gtg<br>Ala Val Ile Trp Tyr Asp Gly Arg Asn Lys Tyr Tyr Ala Asp Ser Val<br>    50                  55                  60 | | 192 |
| aag ggc aga ttc acc atc tct cgg gac aac tcc aag aac acc ctg tac<br>Lys Gly Arg Phe Thr Ile Ser Arg Asp Asn Ser Lys Asn Thr Leu Tyr<br>65                  70                  75                  80 | | 240 |
| ctg cag atg aac tcc ctg aga gcc gag gac acc gcc gtg tac tac tgc<br>Leu Gln Met Asn Ser Leu Arg Ala Glu Asp Thr Ala Val Tyr Tyr Cys<br>            85                  90                  95 | | 288 |
| acc aga gat cac tcc ggc tcc ggc agc tac tac atc gat tat tgg ggc<br>Thr Arg Asp His Ser Gly Ser Gly Ser Tyr Tyr Ile Asp Tyr Trp Gly<br>        100                 105                 110 | | 336 |
| cag ggc acc ctg gtc acc gtg tcc tct gct tct acc aag gga ccc agc<br>Gln Gly Thr Leu Val Thr Val Ser Ser Ala Ser Thr Lys Gly Pro Ser<br>    115                 120                 125 | | 384 |
| gtg ttc cct ctg gct cct tcc agc aag tct acc tct ggc gga aca gct<br>Val Phe Pro Leu Ala Pro Ser Ser Lys Ser Thr Ser Gly Gly Thr Ala<br>130                 135                 140 | | 432 |
| gct ctg ggc tgc ctg gtc aag gac tac ttt cct gag cct gtg acc gtg<br>Ala Leu Gly Cys Leu Val Lys Asp Tyr Phe Pro Glu Pro Val Thr Val<br>145                 150                 155                 160 | | 480 |
| tct tgg aac tct ggc gct ctg aca tct ggc gtg cac acc ttt cca gct<br>Ser Trp Asn Ser Gly Ala Leu Thr Ser Gly Val His Thr Phe Pro Ala<br>            165                 170                 175 | | 528 |
| gtg ctg cag tcc tcc ggc ctg tac tct ctg tct gtc gtg acc gtg<br>Val Leu Gln Ser Ser Gly Leu Tyr Ser Leu Ser Ser Val Val Thr Val<br>        180                 185                 190 | | 576 |
| cct tcc agc tct ctg gga acc cag acc tac atc tgc aat gtg aac cac<br>Pro Ser Ser Ser Leu Gly Thr Gln Thr Tyr Ile Cys Asn Val Asn His<br>    195                 200                 205 | | 624 |
| aag cct tcc aac acc aag gtg gac aag aag gtg gaa ccc aag tcc tgc<br>Lys Pro Ser Asn Thr Lys Val Asp Lys Lys Val Glu Pro Lys Ser Cys<br>210                 215                 220 | | 672 |
| gac aag acc cac acc tgt cct cca tgt cct gct cca gaa ctg ctc ggc<br>Asp Lys Thr His Thr Cys Pro Pro Cys Pro Ala Pro Glu Leu Leu Gly<br>225                 230                 235                 240 | | 720 |
| ggt ccc tcc gtt ttc ctg ttt cca cct aag cct aag gac acc ctg atg<br>Gly Pro Ser Val Phe Leu Phe Pro Pro Lys Pro Lys Asp Thr Leu Met<br>            245                 250                 255 | | 768 |
| atc tct cgg acc cct gaa gtg aca tgc gtg gtg gtg gat gtg tcc cac<br>Ile Ser Arg Thr Pro Glu Val Thr Cys Val Val Val Asp Val Ser His<br>        260                 265                 270 | | 816 |
| gag gat ccc gaa gtg aag ttc aat tgg tac gtg gac ggc gtg gaa gtg<br>Glu Asp Pro Glu Val Lys Phe Asn Trp Tyr Val Asp Gly Val Glu Val<br>    275                 280                 285 | | 864 |
| cac aac gcc aag acc aag cct aga gag gaa cag tac aac tcc acc tac<br>His Asn Ala Lys Thr Lys Pro Arg Glu Glu Gln Tyr Asn Ser Thr Tyr<br>290                 295                 300 | | 912 |
| aga gtg gtg tcc gtg ctg acc gtg ctg cac cag gat tgg ctg aac ggc<br>Arg Val Val Ser Val Leu Thr Val Leu His Gln Asp Trp Leu Asn Gly | | 960 |

```
                305                 310                 315                 320
aaa gag tac aag tgc aag gtg tcc aac aag gcc ctg cct gct cct atc        1008
Lys Glu Tyr Lys Cys Lys Val Ser Asn Lys Ala Leu Pro Ala Pro Ile
                325                 330                 335 gaa aag acc atc tcc aag gct aag ggc cag cct cgg gaa cct cag gtt        1056
Glu Lys Thr Ile Ser Lys Ala Lys Gly Gln Pro Arg Glu Pro Gln Val
            340                 345                 350 tac aca ctg cct cca tct cgg gac gag ctg acc aag aat cag gtg tcc        1104
Tyr Thr Leu Pro Pro Ser Arg Asp Glu Leu Thr Lys Asn Gln Val Ser
        355                 360                 365 ctg acc tgc ctc gtg aag ggc ttc tac cct tct gat atc gcc gtg gaa        1152
Leu Thr Cys Leu Val Lys Gly Phe Tyr Pro Ser Asp Ile Ala Val Glu
    370                 375                 380 tgg gag tcc aac ggc cag cct gag aac aac tac aag aca acc cct cct        1200
Trp Glu Ser Asn Gly Gln Pro Glu Asn Asn Tyr Lys Thr Thr Pro Pro
385                 390                 395                 400 gtg ctg gac tcc gac ggc tca ttc ttc ctg tac tcc aag ctg aca gtg        1248
Val Leu Asp Ser Asp Gly Ser Phe Phe Leu Tyr Ser Lys Leu Thr Val
                405                 410                 415 gat aag tcc cgg tgg cag cag ggc aac gtg ttc tct tgt tct gtg atg        1296
Asp Lys Ser Arg Trp Gln Gln Gly Asn Val Phe Ser Cys Ser Val Met
            420                 425                 430 cac gag gcc ctg cac aac cac tac acc cag aag agt ctg tct ctg tcc        1344
His Glu Ala Leu His Asn His Tyr Thr Gln Lys Ser Leu Ser Leu Ser
        435                 440                 445 cct ggc aag tga                                                        1356
Pro Gly Lys
    450

<210> SEQ ID NO 4
<211> LENGTH: 451
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp His Ser Gly Ser Gly Ser Tyr Tyr Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                      165                 170                 175
Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 5
<211> LENGTH: 1356
<212> TYPE: DNA
<213> ORGANISM: Artificial Sequence
<220> FEATURE:
<223> OTHER INFORMATION: 16B11.1_HC_H
<220> FEATURE:
<221> NAME/KEY: CDS
<222> LOCATION: (1)..(1356)

<400> SEQUENCE: 5 cag gtt cag ctg gtt gaa tct ggc ggc gga gtt gtt cag cct ggc gga      48
Gln Val Gln Leu Val Glu Ser Gly Gly Gly Val Val Gln Pro Gly Gly
1               5                  10                  15 tct ctg aga ctg tct tgt gcc gcc tcc ggc ttc acc ttc tcc tct tac      96
Ser Leu Arg Leu Ser Cys Ala Ala Ser Gly Phe Thr Phe Ser Ser Tyr
            20                  25                  30 gga atg cac tgg gtc cga cag gcc cct ggc aaa gga ttg gaa tgg gtc     144
Gly Met His Trp Val Arg Gln Ala Pro Gly Lys Gly Leu Glu Trp Val
```

-continued

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |

```
gcc gtg att tgg tac gac ggc cgg aac aag tac tac gcc gac tcc gtg      192
Ala Val Ile Trp Tyr Asp Gly Arg Asn Lys Tyr Tyr Ala Asp Ser Val
 50              55                  60 aag ggc aga ttc acc atc tct cgg gac aac tcc aag aac acc ctg tac      240
Lys Gly Arg Phe Thr Ile Ser Arg Asp Asn Ser Lys Asn Thr Leu Tyr
 65              70                  75                  80 ctg cag atg aac tcc ctg aga gcc gag gac acc gcc gtg tac tac tgc      288
Leu Gln Met Asn Ser Leu Arg Ala Glu Asp Thr Ala Val Tyr Tyr Cys
                 85                  90                  95 acc aga gat cac tcc ggc tcc ggc agc tac tac atc gat tat tgg ggc      336
Thr Arg Asp His Ser Gly Ser Gly Ser Tyr Tyr Ile Asp Tyr Trp Gly
                100                 105                 110 cag ggc acc ctg gtc acc gtg tcc tct gct tct acc aag gga ccc agc      384
Gln Gly Thr Leu Val Thr Val Ser Ser Ala Ser Thr Lys Gly Pro Ser
            115                 120                 125 gtg ttc cct ctg gct cct tcc agc aag tct acc tct ggc gga aca gct      432
Val Phe Pro Leu Ala Pro Ser Ser Lys Ser Thr Ser Gly Gly Thr Ala
130                 135                 140 gct ctg ggc tgc ctg gtc aag gac tac ttt cct gag cct gtg acc gtg      480
Ala Leu Gly Cys Leu Val Lys Asp Tyr Phe Pro Glu Pro Val Thr Val
145                 150                 155                 160 tct tgg aac tct ggc gct ctg aca tct ggc gtg cac acc ttt cca gct      528
Ser Trp Asn Ser Gly Ala Leu Thr Ser Gly Val His Thr Phe Pro Ala
                165                 170                 175 gtg ctg cag tcc tcc ggc ctg tac tct ctg tcc tct gtc gtg acc gtg      576
Val Leu Gln Ser Ser Gly Leu Tyr Ser Leu Ser Ser Val Val Thr Val
                180                 185                 190 cct tcc agc tct ctg gga acc cag acc tac atc tgc aat gtg aac cac      624
Pro Ser Ser Ser Leu Gly Thr Gln Thr Tyr Ile Cys Asn Val Asn His
            195                 200                 205 aag cct tcc aac acc aag gtg gac aag aag gtg gaa ccc aag tcc tgc      672
Lys Pro Ser Asn Thr Lys Val Asp Lys Lys Val Glu Pro Lys Ser Cys
210                 215                 220 gac aag acc cac acc tgt cct cca tgt cct gct cca gaa gct gct ggc      720
Asp Lys Thr His Thr Cys Pro Pro Cys Pro Ala Pro Glu Ala Ala Gly
225                 230                 235                 240 ggc cct tcc gtg ttt ctg ttc cct cca aag cct aag gac acc ctg atg      768
Gly Pro Ser Val Phe Leu Phe Pro Pro Lys Pro Lys Asp Thr Leu Met
                245                 250                 255 atc tct cgg acc cct gaa gtg acc tgc gtg gtg gtg gat gtg tct cac      816
Ile Ser Arg Thr Pro Glu Val Thr Cys Val Val Val Asp Val Ser His
                260                 265                 270 gag gat ccc gaa gtg aag ttc aat tgg tac gtg gac ggc gtg gaa gtg      864
Glu Asp Pro Glu Val Lys Phe Asn Trp Tyr Val Asp Gly Val Glu Val
            275                 280                 285 cac aac gcc aag acc aag cct aga gag gaa cag tac ggc tcc acc tac      912
His Asn Ala Lys Thr Lys Pro Arg Glu Glu Gln Tyr Gly Ser Thr Tyr
290                 295                 300 aga gtg gtg tcc gtg ctg acc gtg ctg cac cag gat tgg ctg aac ggc      960
Arg Val Val Ser Val Leu Thr Val Leu His Gln Asp Trp Leu Asn Gly
305                 310                 315                 320 aaa gag tac aag tgc aag gtg tcc aac aag gcc ctg cct gct cct atc     1008
Lys Glu Tyr Lys Cys Lys Val Ser Asn Lys Ala Leu Pro Ala Pro Ile
                325                 330                 335 gaa aag acc atc tcc aag gcc aag ggc cag cct agg gaa ccc cag gtt     1056
Glu Lys Thr Ile Ser Lys Ala Lys Gly Gln Pro Arg Glu Pro Gln Val
            340                 345                 350 tac acc ttg cct cca tct cgg gac gag ctg acc aag aac cag gtg tcc     1104
```

```
Tyr Thr Leu Pro Pro Ser Arg Asp Glu Leu Thr Lys Asn Gln Val Ser
            355                 360                 365 ctg tct tgc gct gtg aag ggc ttc tac ccc tcc gat atc gcc gtg gaa     1152
Leu Ser Cys Ala Val Lys Gly Phe Tyr Pro Ser Asp Ile Ala Val Glu
370                 375                 380 tgg gag tct aat ggc cag cct gag aac aac tac aag aca acc cct cct     1200
Trp Glu Ser Asn Gly Gln Pro Glu Asn Asn Tyr Lys Thr Thr Pro Pro
385                 390                 395                 400 gtg ctg gac tcc gac ggc tca ttc ttc ctg gtg tcc aag ctg aca gtg     1248
Val Leu Asp Ser Asp Gly Ser Phe Phe Leu Val Ser Lys Leu Thr Val
                405                 410                 415 gac aag tcc aga tgg cag cag ggc aac gtg ttc tcc tgc agc gtg atg     1296
Asp Lys Ser Arg Trp Gln Gln Gly Asn Val Phe Ser Cys Ser Val Met
            420                 425                 430 cac gag gcc ctg cac aat cac tac acc cag aag tct ctg tct ctg agc     1344
His Glu Ala Leu His Asn His Tyr Thr Gln Lys Ser Leu Ser Leu Ser
            435                 440                 445 ccc ggc aaa tga                                                     1356
Pro Gly Lys
    450
```

```
<210> SEQ ID NO 6
<211> LENGTH: 451
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp His Ser Gly Ser Gly Ser Tyr Tyr Ile Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

-continued

```
Asp Lys Thr His Thr Cys Pro Pro Cys Pro Ala Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Gly Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
435                 440                 445

Pro Gly Lys
    450

<210> SEQ ID NO 7
<211> LENGTH: 642
<212> TYPE: DNA
<213> ORGANISM: Artificial Sequence
<220> FEATURE:
<223> OTHER INFORMATION: 16B11.1_LC
<220> FEATURE:
<221> NAME/KEY: CDS
<222> LOCATION: (1)..(642)

<400> SEQUENCE: 7 gag att gcc atg aca cag tct ccc gcc aca ctg tct gtt agc cct ggc    48
Glu Ile Ala Met Thr Gln Ser Pro Ala Thr Leu Ser Val Ser Pro Gly
1               5                   10                  15 gag aga gct acc ctg tcc tgt aga gcc tct cag tcc gtg tcc tct aac    96
Glu Arg Ala Thr Leu Ser Cys Arg Ala Ser Gln Ser Val Ser Ser Asn
            20                  25                  30 ctg gcc tgg tat cag cag aag cct gga cag gct ccc cgg ctg ttg atc   144
Leu Ala Trp Tyr Gln Gln Lys Pro Gly Gln Ala Pro Arg Leu Leu Ile
        35                  40                  45 tat ggc gct tct acc aga gct acc ggc ctg cct gct aga ttc tcc ggc   192
Tyr Gly Ala Ser Thr Arg Ala Thr Gly Leu Pro Ala Arg Phe Ser Gly
    50                  55                  60 tct gga tct ggc acc gag ttt acc ctg acc atc tcc agc ctg cag tcc   240
Ser Gly Ser Gly Thr Glu Phe Thr Leu Thr Ile Ser Ser Leu Gln Ser
65                  70                  75                  80 gag gat ttc gcc gtg tac tac tgc cag cag tac aac aac ttc tgg acc   288
```

```
                Glu Asp Phe Ala Val Tyr Tyr Cys Gln Gln Tyr Asn Asn Phe Trp Thr
                                    85                  90                  95 ttc ggc cag ggc acc aag gtg gaa atc aag aga acc gtg gcc gct cct            336
Phe Gly Gln Gly Thr Lys Val Glu Ile Lys Arg Thr Val Ala Ala Pro
            100                 105                 110 tcc gtg ttc atc ttc cca cct tcc gac gag cag ctg aag tcc ggc aca            384
Ser Val Phe Ile Phe Pro Pro Ser Asp Glu Gln Leu Lys Ser Gly Thr
115                 120                 125 gct tct gtc gtg tgc ctg ctg aac aac ttt tac cct cgg gaa gcc aag            432
Ala Ser Val Val Cys Leu Leu Asn Asn Phe Tyr Pro Arg Glu Ala Lys
    130                 135                 140 gtg cag tgg aag gtg gac aat gcc ctg cag agc ggc aac tcc caa gag            480
Val Gln Trp Lys Val Asp Asn Ala Leu Gln Ser Gly Asn Ser Gln Glu
145                 150                 155                 160 tct gtg acc gag cag gac tcc aag gac agc acc tac agc ctg tcc tcc            528
Ser Val Thr Glu Gln Asp Ser Lys Asp Ser Thr Tyr Ser Leu Ser Ser
                165                 170                 175 aca ctg acc ctg tcc aag gcc gac tac gag aag cac aag gtg tac gcc            576
Thr Leu Thr Leu Ser Lys Ala Asp Tyr Glu Lys His Lys Val Tyr Ala
            180                 185                 190 tgc gaa gtg acc cat cag ggc ctg tct agc cct gtg acc aag tct ttc            624
Cys Glu Val Thr His Gln Gly Leu Ser Ser Pro Val Thr Lys Ser Phe
        195                 200                 205 aac cgg ggc gag tgc tga                                                    642
Asn Arg Gly Glu Cys
    210

<210> SEQ ID NO 8
<211> LENGTH: 213
<212> TYPE: PRT
<213> ORGANISM: Artificial Sequence
<220> FEATURE:
<223> OTHER INFORMATION: Synthetic Construct

<400> SEQUENCE: 8

Glu Ile Ala Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Phe Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
```

<210> SEQ ID NO 9
<211> LENGTH: 1356
<212> TYPE: DNA
<213> ORGANISM: Artificial Sequence
<220> FEATURE:
<223> OTHER INFORMATION: 16B12.1_HC
<220> FEATURE:
<221> NAME/KEY: CDS
<222> LOCATION: (1)..(1356)

<400> SEQUENCE: 9

```
cag gtt cag ctg gtt gaa tct ggc ggc gga gtt gtt cag cct ggc gga        48
Gln Val Gln Leu Val Glu Ser Gly Gly Gly Val Val Gln Pro Gly Gly
 1               5                  10                  15 tct ctg aga ctg tct tgt gcc gcc tcc ggc ttc atc ttc tcc agc tac        96
Ser Leu Arg Leu Ser Cys Ala Ala Ser Gly Phe Ile Phe Ser Ser Tyr
             20                  25                  30 gga atg cac tgg gtc cga cag gcc cct ggc aaa gga ttg gaa tgg gtc       144
Gly Met His Trp Val Arg Gln Ala Pro Gly Lys Gly Leu Glu Trp Val
         35                  40                  45 gcc gtg att tgg tac gac ggc tcc aac aag tac tac gcc gac tcc gtg       192
Ala Val Ile Trp Tyr Asp Gly Ser Asn Lys Tyr Tyr Ala Asp Ser Val
     50                  55                  60 aag ggc aga ttc acc atc tct cgg gac aac tcc aag aac acc ctg tac       240
Lys Gly Arg Phe Thr Ile Ser Arg Asp Asn Ser Lys Asn Thr Leu Tyr
 65                  70                  75                  80 ctg cag atg aac tcc ctg aga gcc gag gac acc gcc atg tac tac tgc       288
Leu Gln Met Asn Ser Leu Arg Ala Glu Asp Thr Ala Met Tyr Tyr Cys
                 85                  90                  95 gcc aga gat cac tac ggc tcc ggc acc tac tac atc gac tat tgg ggc       336
Ala Arg Asp His Tyr Gly Ser Gly Thr Tyr Tyr Ile Asp Tyr Trp Gly
            100                 105                 110 cag ggc acc ctg gtc aca gtg tcc tct gct tct acc aag gga ccc agc       384
Gln Gly Thr Leu Val Thr Val Ser Ser Ala Ser Thr Lys Gly Pro Ser
        115                 120                 125 gtg ttc cct ctg gct cct tcc agc aag tct acc tct ggc gga aca gct       432
Val Phe Pro Leu Ala Pro Ser Ser Lys Ser Thr Ser Gly Gly Thr Ala
    130                 135                 140 gct ctg ggc tgc ctg gtc aag gac tac ttt cct gag cct gtg acc gtg       480
Ala Leu Gly Cys Leu Val Lys Asp Tyr Phe Pro Glu Pro Val Thr Val
145                 150                 155                 160 tcc tgg aac tct ggc gct ctg aca tct ggc gtg cac acc ttt cca gct       528
Ser Trp Asn Ser Gly Ala Leu Thr Ser Gly Val His Thr Phe Pro Ala
                165                 170                 175 gtg ctg cag tcc tcc ggc ctg tac tct ctg tcc tct gtc gtg acc gtg       576
Val Leu Gln Ser Ser Gly Leu Tyr Ser Leu Ser Ser Val Val Thr Val
            180                 185                 190 cct tcc agc tct ctg gga acc cag acc tac atc tgc aat gtg aac cac       624
Pro Ser Ser Ser Leu Gly Thr Gln Thr Tyr Ile Cys Asn Val Asn His
        195                 200                 205 aag cct tcc aac acc aag gtg gac aag aag gtg gaa ccc aag tcc tgc       672
Lys Pro Ser Asn Thr Lys Val Asp Lys Lys Val Glu Pro Lys Ser Cys
    210                 215                 220 gac aag acc cac acc tgt cct cca tgt cct gct cca gaa ctg ctc ggc       720
Asp Lys Thr His Thr Cys Pro Pro Cys Pro Ala Pro Glu Leu Leu Gly
```

```
                225                 230                 235                 240
ggt ccc tcc gtt ttc ctg ttt cca cct aag cct aag gac acc ctg atg           768
Gly Pro Ser Val Phe Leu Phe Pro Pro Lys Pro Lys Asp Thr Leu Met
                245                 250                 255 atc tct cgg acc cct gaa gtg aca tgc gtg gtg gtg gat gtg tcc cac           816
Ile Ser Arg Thr Pro Glu Val Thr Cys Val Val Val Asp Val Ser His
            260                 265                 270 gag gat ccc gaa gtg aag ttc aat tgg tac gtg gac ggc gtg gaa gtg           864
Glu Asp Pro Glu Val Lys Phe Asn Trp Tyr Val Asp Gly Val Glu Val
        275                 280                 285 cac aac gcc aag acc aag cct aga gag gaa cag tac aac tcc acc tac           912
His Asn Ala Lys Thr Lys Pro Arg Glu Glu Gln Tyr Asn Ser Thr Tyr
    290                 295                 300 aga gtg gtg tcc gtg ctg acc gtg ctg cac cag gat tgg ctg aac ggc           960
Arg Val Val Ser Val Leu Thr Val Leu His Gln Asp Trp Leu Asn Gly
305                 310                 315                 320 aaa gag tac aag tgc aag gtg tcc aac aag gcc ctg cct gct cct atc          1008
Lys Glu Tyr Lys Cys Lys Val Ser Asn Lys Ala Leu Pro Ala Pro Ile
                325                 330                 335 gaa aag acc atc tcc aag gct aag ggc cag cct cgg gaa cct cag gtt          1056
Glu Lys Thr Ile Ser Lys Ala Lys Gly Gln Pro Arg Glu Pro Gln Val
            340                 345                 350 tac aca ctg cct cca tct cgg gac gag ctg acc aag aat cag gtg tcc          1104
Tyr Thr Leu Pro Pro Ser Arg Asp Glu Leu Thr Lys Asn Gln Val Ser
        355                 360                 365 ctg acc tgc ctc gtg aag ggc ttc tac cct tct gat atc gcc gtg gaa          1152
Leu Thr Cys Leu Val Lys Gly Phe Tyr Pro Ser Asp Ile Ala Val Glu
    370                 375                 380 tgg gag tcc aac ggc cag cct gag aac aac tac aag aca acc cct cct          1200
Trp Glu Ser Asn Gly Gln Pro Glu Asn Asn Tyr Lys Thr Thr Pro Pro
385                 390                 395                 400 gtg ctg gac tcc gac ggc tca ttc ttc ctg tac tcc aag ctg aca gtg          1248
Val Leu Asp Ser Asp Gly Ser Phe Phe Leu Tyr Ser Lys Leu Thr Val
                405                 410                 415 gat aag tcc cgg tgg cag cag ggc aac gtg ttc tct tgt tct gtg atg          1296
Asp Lys Ser Arg Trp Gln Gln Gly Asn Val Phe Ser Cys Ser Val Met
            420                 425                 430 cac gag gcc ctg cac aac cac tac acc cag aag agt ctg tct ctg tcc          1344
His Glu Ala Leu His Asn His Tyr Thr Gln Lys Ser Leu Ser Leu Ser
        435                 440                 445 cct ggc aag tga                                                          1356
Pro Gly Lys
    450

<210> SEQ ID NO 10
<211> LENGTH: 451
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
            85                  90                  95

Ala Arg Asp His Tyr Gly Ser Gly Thr Tyr Tyr Ile Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450

<210> SEQ ID NO 11
<211> LENGTH: 642

```
<212> TYPE: DNA
<213> ORGANISM: Artificial Sequence
<220> FEATURE:
<223> OTHER INFORMATION: 16B12.1_LC
<220> FEATURE:
<221> NAME/KEY: CDS
<222> LOCATION: (1)..(642)

<400> SEQUENCE: 11 gag att gtg atg acc cag tct cct gcc aca ctg tcc gtg tct cca ggc        48
Glu Ile Val Met Thr Gln Ser Pro Ala Thr Leu Ser Val Ser Pro Gly
1               5                   10                  15 gag aga gct acc ctg tct tgc aga gct tct cag acc gtg tcc tcc aac        96
Glu Arg Ala Thr Leu Ser Cys Arg Ala Ser Gln Thr Val Ser Ser Asn
            20                  25                  30 ctg gcc tgg tat cag cag aag cct gga cag gct ccc cgg ctg ttg atc       144
Leu Ala Trp Tyr Gln Gln Lys Pro Gly Gln Ala Pro Arg Leu Leu Ile
        35                  40                  45 tat ggc gct tct acc aga gcc acc ggc ttt ccc gct aga ttc tcc ggc       192
Tyr Gly Ala Ser Thr Arg Ala Thr Gly Phe Pro Ala Arg Phe Ser Gly
    50                  55                  60 tct ggc tct ggc aca gag ttt acc ctg acc atc tcc agc ctg cag tcc       240
Ser Gly Ser Gly Thr Glu Phe Thr Leu Thr Ile Ser Ser Leu Gln Ser
65                  70                  75                  80 gag gat ttc gcc gtg tac tac tgc cag cag tac aac aac tgg tgg acc       288
Glu Asp Phe Ala Val Tyr Tyr Cys Gln Gln Tyr Asn Asn Trp Trp Thr
                85                  90                  95 ttc ggc cag ggc acc aag gtg gaa atc aag aga acc gtg gcc gct cct       336
Phe Gly Gln Gly Thr Lys Val Glu Ile Lys Arg Thr Val Ala Ala Pro
            100                 105                 110 tcc gtg ttc atc ttc cca cct tcc gac gag cag ctg aag tct ggc acc       384
Ser Val Phe Ile Phe Pro Pro Ser Asp Glu Gln Leu Lys Ser Gly Thr
        115                 120                 125 gct tct gtc gtg tgc ctg ctg aac aac ttc tac cct cgg gaa gcc aag       432
Ala Ser Val Val Cys Leu Leu Asn Asn Phe Tyr Pro Arg Glu Ala Lys
    130                 135                 140 gtg cag tgg aag gtg gac aat gcc ctg cag agc ggc aac tcc caa gag       480
Val Gln Trp Lys Val Asp Asn Ala Leu Gln Ser Gly Asn Ser Gln Glu
145                 150                 155                 160 tct gtg acc gag cag gac tcc aag gac agc acc tac agc ctg tcc tcc       528
Ser Val Thr Glu Gln Asp Ser Lys Asp Ser Thr Tyr Ser Leu Ser Ser
                165                 170                 175 aca ctg acc ctg tcc aag gcc gac tac gag aag cac aag gtg tac gcc       576
Thr Leu Thr Leu Ser Lys Ala Asp Tyr Glu Lys His Lys Val Tyr Ala
            180                 185                 190 tgc gaa gtg acc cat cag ggc ctg tct agc cct gtg acc aag tct ttc       624
Cys Glu Val Thr His Gln Gly Leu Ser Ser Pro Val Thr Lys Ser Phe
        195                 200                 205 aac cgg ggc gag tgt tga                                                642
Asn Arg Gly Glu Cys
    210

<210> SEQ ID NO 12
<211> LENGTH: 213
<212> TYPE: PRT
<213> ORGANISM: Artificial Sequence
<220> FEATURE:
<223> OTHER INFORMATION: Synthetic Construct

<400> SEQUENCE: 12

Glu Ile Val Met Thr Gln Ser Pro Ala Thr Leu Ser Val Ser Pro Gly
1               5                   10                  15
```

```
Glu Arg Ala Thr Leu Ser Cys Arg Ala Ser Gln Thr Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Phe Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 13
<211> LENGTH: 1461
<212> TYPE: DNA
<213> ORGANISM: Artificial Sequence
<220> FEATURE:
<223> OTHER INFORMATION: anti-CD3-scFv
<220> FEATURE:
<221> NAME/KEY: CDS
<222> LOCATION: (1)..(1461)

<400> SEQUENCE: 13 gaa gta cag ctg gtg gag tct ggc gga ggt ctt atc cag ccc gga ggt      48
Glu Val Gln Leu Val Glu Ser Gly Gly Gly Leu Ile Gln Pro Gly Gly
1               5                   10                  15 tct ctg cgc ctg agc tgt gca gct tcc ggt ttc acc ttc aac acc tat      96
Ser Leu Arg Leu Ser Cys Ala Ala Ser Gly Phe Thr Phe Asn Thr Tyr
            20                  25                  30 gcc atg aat tgg gta cgc cag gct cca gga aaa tgt ctg gag tgg gtg     144
Ala Met Asn Trp Val Arg Gln Ala Pro Gly Lys Cys Leu Glu Trp Val
        35                  40                  45 gct cgg att cga agc aaa tac aac aat tat gca acc tac tat gcc gac     192
Ala Arg Ile Arg Ser Lys Tyr Asn Asn Tyr Ala Thr Tyr Tyr Ala Asp
    50                  55                  60 agt gtc aag gac cgc ttc acc ata agt cgg gat gac tcc aag agc act     240
Ser Val Lys Asp Arg Phe Thr Ile Ser Arg Asp Asp Ser Lys Ser Thr
65                  70                  75                  80 ctg tat ctg cag atg aac aac ttg agg gcc gag gat acc gcc gtt tac     288
Leu Tyr Leu Gln Met Asn Asn Leu Arg Ala Glu Asp Thr Ala Val Tyr
                85                  90                  95 tat tgc gta agg cat ggc aac ttc ggt aat tcc tac gtg tcc tgg ttt     336
Tyr Cys Val Arg His Gly Asn Phe Gly Asn Ser Tyr Val Ser Trp Phe
            100                 105                 110
```

| | | |
|---|---|---|
| gcc tat tgg ggc caa ggg acg ctg gtt aca gtg tca agt gga aag ccc<br>Ala Tyr Trp Gly Gln Gly Thr Leu Val Thr Val Ser Ser Gly Lys Pro<br>115 120 125 | | 384 |
| ggg tct ggc aaa cct ggg agt ggc aag ccc ggg agt ggg aaa cca gga<br>Gly Ser Gly Lys Pro Gly Ser Gly Lys Pro Gly Ser Gly Lys Pro Gly<br>130 135 140 | | 432 |
| tcc cag gct gtt gtc act caa gaa ccc agt ctc act gtt tct cca ggc<br>Ser Gln Ala Val Val Thr Gln Glu Pro Ser Leu Thr Val Ser Pro Gly<br>145 150 155 160 | | 480 |
| ggt aca gtc aca ctc aca tgt cgt agc agc act ggg gct gtg acc acc<br>Gly Thr Val Thr Leu Thr Cys Arg Ser Ser Thr Gly Ala Val Thr Thr<br>165 170 175 | | 528 |
| agc aac tat gca aac tgg gtc cag cag aaa ccc ggt caa gct ccc aga<br>Ser Asn Tyr Ala Asn Trp Val Gln Gln Lys Pro Gly Gln Ala Pro Arg<br>180 185 190 | | 576 |
| gga ttg att ggc ggt acc aat aag cgg gcc cct ggg act cct gct cga<br>Gly Leu Ile Gly Gly Thr Asn Lys Arg Ala Pro Gly Thr Pro Ala Arg<br>195 200 205 | | 624 |
| ttt tct ggc tcc ttg ctt gga gat aaa gcc gca ctg act ttg agc ggc<br>Phe Ser Gly Ser Leu Leu Gly Asp Lys Ala Ala Leu Thr Leu Ser Gly<br>210 215 220 | | 672 |
| gct caa cca gag gac gaa gca gag tac tat tgt gct ctg tgg tac tcc<br>Ala Gln Pro Glu Asp Glu Ala Glu Tyr Tyr Cys Ala Leu Trp Tyr Ser<br>225 230 235 240 | | 720 |
| aac ctc tgg gtg ttt ggc tgt ggc acc aag gta aca gtg ctg gaa cct<br>Asn Leu Trp Val Phe Gly Cys Gly Thr Lys Val Thr Val Leu Glu Pro<br>245 250 255 | | 768 |
| aag tca agc gac aaa aca cac acc tgt cct ccc tgt cca gca cca gag<br>Lys Ser Ser Asp Lys Thr His Thr Cys Pro Pro Cys Pro Ala Pro Glu<br>260 265 270 | | 816 |
| gca gct ggt ggc cca tct gtc ttt ctg ttc cca cca aag ccc aag gac<br>Ala Ala Gly Gly Pro Ser Val Phe Leu Phe Pro Pro Lys Pro Lys Asp<br>275 280 285 | | 864 |
| act ctg atg atc tca cga aca ccc gaa gtg act tgc gta gtg gtg gac<br>Thr Leu Met Ile Ser Arg Thr Pro Glu Val Thr Cys Val Val Val Asp<br>290 295 300 | | 912 |
| gtt tct cat gag gat cca gag gtc aag ttc aac tgg tac gtg gat gga<br>Val Ser His Glu Asp Pro Glu Val Lys Phe Asn Trp Tyr Val Asp Gly<br>305 310 315 320 | | 960 |
| gtg gaa gtg cac aat gcc aaa aca aag ccc cgt gag gag cag tac ggc<br>Val Glu Val His Asn Ala Lys Thr Lys Pro Arg Glu Glu Gln Tyr Gly<br>325 330 335 | | 1008 |
| tcc acg tac agg gtt gtc tcc gtt ttg acc gtc ctg cat cag gat tgg<br>Ser Thr Tyr Arg Val Val Ser Val Leu Thr Val Leu His Gln Asp Trp<br>340 345 350 | | 1056 |
| ctt aac gga aaa gag tat aag tgc aag gta tcc aat aag gcc ctt ccc<br>Leu Asn Gly Lys Glu Tyr Lys Cys Lys Val Ser Asn Lys Ala Leu Pro<br>355 360 365 | | 1104 |
| gcc cct atc gag aaa act atc agc aag gcc aaa gga cag ccc aga gag<br>Ala Pro Ile Glu Lys Thr Ile Ser Lys Ala Lys Gly Gln Pro Arg Glu<br>370 375 380 | | 1152 |
| ccc cag gtg tac act ttg cct cct tct agg gat gaa ctc acc aag aat<br>Pro Gln Val Tyr Thr Leu Pro Pro Ser Arg Asp Glu Leu Thr Lys Asn<br>385 390 395 400 | | 1200 |
| cag gtt agc ctg tgg tgc ctg gtg aag ggg ttt tac cca tcc gat att<br>Gln Val Ser Leu Trp Cys Leu Val Lys Gly Phe Tyr Pro Ser Asp Ile<br>405 410 415 | | 1248 |
| gcc gtg gag tgg gaa agc aat ggc caa ccc gag aac aac tat aag aca<br>Ala Val Glu Trp Glu Ser Asn Gly Gln Pro Glu Asn Asn Tyr Lys Thr | | 1296 |

```
                    420                 425                 430
act cct cct gtg ctg gac tca gat gga agt ttc ttc ctg tac agc aag     1344
Thr Pro Pro Val Leu Asp Ser Asp Gly Ser Phe Phe Leu Tyr Ser Lys
        435                 440                 445 ctc aca gtg gac aag agc aga tgg cag cag ggc aat gtg ttt tct tgc     1392
Leu Thr Val Asp Lys Ser Arg Trp Gln Gln Gly Asn Val Phe Ser Cys
450                 455                 460 tct gtc atg cac gaa gcc ctg cac aat cac tac acc cag aaa tcc ctt     1440
Ser Val Met His Glu Ala Leu His Asn His Tyr Thr Gln Lys Ser Leu
465                 470                 475                 480 agt ctg tca cct ggg aag tga                                         1461
Ser Leu Ser Pro Gly Lys
                485

<210> SEQ ID NO 14
<211> LENGTH: 486
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Asn Leu Arg Ala Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Arg Ser Ser Thr Gly Ala Val Thr Thr
            165                 170                 175

Ser Asn Tyr Ala Asn Trp Val Gln Gln Lys Pro Gly Gln Ala Pro Arg
        180                 185                 190

Gly Leu Ile Gly Gly Thr Asn Lys Arg Ala Pro Gly Thr Pro Ala Arg
    195                 200                 205

Phe Ser Gly Ser Leu Leu Gly Asp Lys Ala Ala Leu Thr Leu Ser Gly
        210                 215                 220

Ala Gln Pro Glu Asp Glu Ala Glu Tyr Tyr Cys Ala Leu Trp Tyr Ser
225                 230                 235                 240

Asn Leu Trp Val Phe Gly Cys Gly Thr Lys Val Thr Val Leu Glu Pro
            245                 250                 255

Lys Ser Ser Asp Lys Thr His Thr Cys Pro Pro Cys Pro Ala Pro Glu
        260                 265                 270
```

```
Ala Ala Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Gly
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Trp Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 15
<211> LENGTH: 4
<212> TYPE: PRT
<213> ORGANISM: Artificial Sequence
<220> FEATURE:
<223> OTHER INFORMATION: GGGS linker
<220> FEATURE:
<221> NAME/KEY: PEPTIDE
<222> LOCATION: (1)..(4)

<400> SEQUENCE: 15

Gly Gly Gly Ser
1

<210> SEQ ID NO 16
<211> LENGTH: 4
<212> TYPE: PRT
<213> ORGANISM: Artificial Sequence
<220> FEATURE:
<223> OTHER INFORMATION: SGGG linker
<220> FEATURE:
<221> NAME/KEY: PEPTIDE
<222> LOCATION: (1)..(4)

<400> SEQUENCE: 16

Ser Gly Gly Gly
1

<210> SEQ ID NO 17
<211> LENGTH: 5
<212> TYPE: PRT
<213> ORGANISM: Artificial Sequence
```

```
<220> FEATURE:
<223> OTHER INFORMATION: GGGGS linker
<220> FEATURE:
<221> NAME/KEY: PEPTIDE
<222> LOCATION: (1)..(5)

<400> SEQUENCE: 17

Gly Gly Gly Gly Ser
1               5

<210> SEQ ID NO 18
<211> LENGTH: 5
<212> TYPE: PRT
<213> ORGANISM: Artificial Sequence
<220> FEATURE:
<223> OTHER INFORMATION: SGGGG linker
<220> FEATURE:
<221> NAME/KEY: PEPTIDE
<222> LOCATION: (1)..(5)

<400> SEQUENCE: 18

Ser Gly Gly Gly Gly
1               5

<210> SEQ ID NO 19
<211> LENGTH: 6
<212> TYPE: PRT
<213> ORGANISM: Artificial Sequence
<220> FEATURE:
<223> OTHER INFORMATION: GGGGGS linker
<220> FEATURE:
<221> NAME/KEY: PEPTIDE
<222> LOCATION: (1)..(6)

<400> SEQUENCE: 19

Gly Gly Gly Gly Gly Ser
1               5

<210> SEQ ID NO 20
<211> LENGTH: 6
<212> TYPE: PRT
<213> ORGANISM: Artificial Sequence
<220> FEATURE:
<223> OTHER INFORMATION: SGGGGG linker
<220> FEATURE:
<221> NAME/KEY: PEPTIDE
<222> LOCATION: (1)..(6)

<400> SEQUENCE: 20

Ser Gly Gly Gly Gly Gly
1               5

<210> SEQ ID NO 21
<211> LENGTH: 7
<212> TYPE: PRT
<213> ORGANISM: Artificial Sequence
<220> FEATURE:
<223> OTHER INFORMATION: GGGGGGS linker
<220> FEATURE:
<221> NAME/KEY: PEPTIDE
<222> LOCATION: (1)..(7)

<400> SEQUENCE: 21

Gly Gly Gly Gly Gly Gly Ser
1               5

<210> SEQ ID NO 22
<211> LENGTH: 7
<212> TYPE: PRT
```

```
<213> ORGANISM: Artificial Sequence
<220> FEATURE:
<223> OTHER INFORMATION: SGGGGGG linker
<220> FEATURE:
<221> NAME/KEY: PEPTIDE
<222> LOCATION: (1)..(7)

<400> SEQUENCE: 22

Ser Gly Gly Gly Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: GKPGS linker
<220> FEATURE:
<221> NAME/KEY: PEPTIDE
<222> LOCATION: (1)..(5)

<400> SEQUENCE: 23

Gly Lys Pro Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: 16B11&16B12_HCDR1
<220> FEATURE:
<221> NAME/KEY: BINDING
<222> LOCATION: (1)..(5)

<400> SEQUENCE: 24

Ser Tyr Gly Met His
1               5

<210> SEQ ID NO 25
<211> LENGTH: 17
<212> TYPE: PRT
<213> ORGANISM: Artificial Sequence
<220> FEATURE:
<223> OTHER INFORMATION: 16B11_HCDR2
<220> FEATURE:
<221> NAME/KEY: BINDING
<222> LOCATION: (1)..(16)

<400> SEQUENCE: 25

Val Ile Trp Tyr Asp Gly Arg Asn Lys Tyr Tyr Ala Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: 16B12_HCDR2
<220> FEATURE:
<221> NAME/KEY: BINDING
<222> LOCATION: (1)..(16)

<400> SEQUENCE: 26

Val Ile Trp Tyr Asp Gly Ser Asn Lys Tyr Tyr Ala Asp Ser Val Lys
1               5                   10                  15

Gly
```

```
<210> SEQ ID NO 27
<211> LENGTH: 12
<212> TYPE: PRT
<213> ORGANISM: Artificial Sequence
<220> FEATURE:
<223> OTHER INFORMATION: 16B11_HCDR3
<220> FEATURE:
<221> NAME/KEY: BINDING
<222> LOCATION: (1)..(12)

<400> SEQUENCE: 27

Asp His Ser Gly Ser Gly Ser Tyr Tyr Ile Asp Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: 16B12_HCDR3
<220> FEATURE:
<221> NAME/KEY: BINDING
<222> LOCATION: (1)..(12)

<400> SEQUENCE: 28

Asp His Tyr Gly Ser Gly Thr Tyr Tyr Ile Asp Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: 16B11_LCDR1
<220> FEATURE:
<221> NAME/KEY: BINDING
<222> LOCATION: (1)..(9)

<400> SEQUENCE: 29

Arg Ala Ser Gln Ser Val Ser Ser Asn Leu Ala
1               5                   10

<210> SEQ ID NO 30
<211> LENGTH: 11
<212> TYPE: PRT
<213> ORGANISM: Artificial Sequence
<220> FEATURE:
<223> OTHER INFORMATION: 16B12_LCDR1
<220> FEATURE:
<221> NAME/KEY: BINDING
<222> LOCATION: (1)..(9)

<400> SEQUENCE: 30

Arg Ala Ser Gln Thr Val Ser Ser Asn Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: 16B11&16B12_LCDR2
<220> FEATURE:
<221> NAME/KEY: BINDING
<222> LOCATION: (1)..(5)

<400> SEQUENCE: 31

Gly Ala Ser Thr Arg Ala Thr
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: 16B11_LCDR3
<220> FEATURE:
<221> NAME/KEY: BINDING
<222> LOCATION: (1)..(8)

<400> SEQUENCE: 32

Gln Gln Tyr Asn Asn Phe Trp Thr
1               5

<210> SEQ ID NO 33
<211> LENGTH: 8
<212> TYPE: PRT
<213> ORGANISM: Artificial Sequence
<220> FEATURE:
<223> OTHER INFORMATION: 16B12_LCDR3
<220> FEATURE:
<221> NAME/KEY: BINDING
<222> LOCATION: (1)..(8)

<400> SEQUENCE: 33

Gln Gln Tyr Asn Asn Trp Trp Thr
1               5

<210> SEQ ID NO 34
<211> LENGTH: 121
<212> TYPE: PRT
<213> ORGANISM: Artificial Sequence
<220> FEATURE:
<223> OTHER INFORMATION: 16B11_VH
<220> FEATURE:
<221> NAME/KEY: BINDING
<222> LOCATION: (1)..(114)

<400> SEQUENCE: 34

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Arg Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp His Ser Gly Ser Gly Ser Tyr Tyr Ile Asp Tyr Trp Gly
                100                 105                 110

Gln Gly Thr Leu Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: 16B12_VH
<220> FEATURE:
```

<221> NAME/KEY: BINDING
<222> LOCATION: (1)..(113)

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp His Tyr Gly Ser Gly Thr Tyr Tyr Ile Asp Tyr Trp Gly
            100                 105                 110

Gln Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: 16B11_VL
<220> FEATURE:
<221> NAME/KEY: BINDING
<222> LOCATION: (1)..(97)

<400> SEQUENCE: 36

Glu Ile Ala Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Phe Trp Thr
                85                  90                  95

Phe Gly Gln Gly Thr Lys Val Glu Ile Lys Arg
            100                 105

<210> SEQ ID NO 37
<211> LENGTH: 107
<212> TYPE: PRT
<213> ORGANISM: Artificial Sequence
<220> FEATURE:
<223> OTHER INFORMATION: 16B12_VL
<220> FEATURE:
<221> NAME/KEY: BINDING
<222> LOCATION: (1)..(98)

<400> SEQUENCE: 37

Glu Ile Val Met Thr Gln Ser Pro Ala Thr Leu Ser Val Ser Pro Gly
1               5                   10                  15

-continued

```
Glu Arg Ala Thr Leu Ser Cys Arg Ala Ser Gln Thr Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Phe Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys Arg
            100                 105
```

<210> SEQ ID NO 38
<211> LENGTH: 19
<212> TYPE: PRT
<213> ORGANISM: Artificial Sequence
<220> FEATURE:
<223> OTHER INFORMATION: signal sequence
<220> FEATURE:
<221> NAME/KEY: PEPTIDE
<222> LOCATION: (1)..(19)

<400> SEQUENCE: 38

```
Met Glu Trp Ser Trp Val Phe Leu Phe Phe Leu Ser Val Thr Thr Gly
1               5                   10                  15

Val His Ser
```

<210> SEQ ID NO 39
<211> LENGTH: 19
<212> TYPE: PRT
<213> ORGANISM: Artificial Sequence
<220> FEATURE:
<223> OTHER INFORMATION: signal sequence
<220> FEATURE:
<221> NAME/KEY: PEPTIDE
<222> LOCATION: (1)..(19)

<400> SEQUENCE: 39

```
Met Gly Trp Ser Cys Ile Ile Leu Phe Leu Val Ala Thr Ala Thr Gly
1               5                   10                  15

Val His Ser
```

<210> SEQ ID NO 40
<211> LENGTH: 19
<212> TYPE: PRT
<213> ORGANISM: Artificial Sequence
<220> FEATURE:
<223> OTHER INFORMATION: signal sequence
<220> FEATURE:
<221> NAME/KEY: PEPTIDE
<222> LOCATION: (1)..(19)

<400> SEQUENCE: 40

```
Met Glu Trp Ser Trp Val Phe Leu Phe Phe Leu Ser Val Thr Thr Gly
1               5                   10                  15

Val His Ser
```

<210> SEQ ID NO 41
<211> LENGTH: 30
<212> TYPE: PRT
<213> ORGANISM: Artificial Sequence
<220> FEATURE:
<223> OTHER INFORMATION: mouseTSPAN8 126-155

```
<400> SEQUENCE: 41

Lys Leu Leu Ser Asp Asn Thr Asp Glu Ala Lys Asp Phe Gln Lys Ala
1               5                   10                  15

Met Ile Val Phe Gln Ser Glu Phe Lys Cys Cys Gly Leu Glu
                20                  25                  30

<210> SEQ ID NO 42
<211> LENGTH: 30
<212> TYPE: PRT
<213> ORGANISM: Artificial Sequence
<220> FEATURE:
<223> OTHER INFORMATION: ratTSPAN8 126-155

<400> SEQUENCE: 42

Lys Leu Leu Ser Glu Thr Ser Asn Glu Ala Lys Glu Val Gln Lys Ala
1               5                   10                  15

Met Ile Ala Phe Gln Ser Glu Phe Lys Cys Cys Gly Leu Arg
                20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Macaca fascicula TSPAN8 126-155

<400> SEQUENCE: 43

Lys Leu Leu Ser Thr Thr Gly Glu Ser Ala Lys Gln Phe Gln Gln Ala
1               5                   10                  15

Met Ala Glu Phe Gln Lys Glu Phe Lys Cys Cys Gly Leu Val
                20                  25                  30
```